United States Patent
Lerner et al.

(10) Patent No.: US 10,426,815 B2
(45) Date of Patent: Oct. 1, 2019

(54) PREVENTION AND TREATMENT OF ITCH WITH AN MRGPR ANTAGONIST

(71) Applicant: THE GENERAL HOSPITAL CORPORATION, Boston, MA (US)

(72) Inventors: Ethan A. Lerner, Chestnut Hill, MA (US); Ehsan Azimi, Boston, MA (US); Vemuri B. Reddy, Ashland, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/543,514

(22) PCT Filed: Jan. 20, 2016

(86) PCT No.: PCT/US2016/014138
§ 371 (c)(1),
(2) Date: Jul. 13, 2017

(87) PCT Pub. No.: WO2016/118632
PCT Pub. Date: Jul. 28, 2016

(65) Prior Publication Data
US 2018/0000886 A1    Jan. 4, 2018

Related U.S. Application Data

(60) Provisional application No. 62/105,420, filed on Jan. 20, 2015.

(51) Int. Cl.
| | | |
|---|---|---|
| A61K 38/00 | (2006.01) | |
| A61K 38/06 | (2006.01) | |
| A61K 9/00 | (2006.01) | |
| A61K 9/70 | (2006.01) | |
| A61K 45/06 | (2006.01) | |
| A61K 31/573 | (2006.01) | |
| A61Q 19/00 | (2006.01) | |

(52) U.S. Cl.
CPC ............ *A61K 38/06* (2013.01); *A61K 9/0014* (2013.01); *A61K 9/7038* (2013.01); *A61K 31/573* (2013.01); *A61K 45/06* (2013.01); *A61Q 19/00* (2013.01)

(58) Field of Classification Search
None
See application file for complete search history.

(56) References Cited

U.S. PATENT DOCUMENTS

| | | |
|---|---|---|
| 5,008,242 A | 4/1991 | Lezdey et al. |
| 5,114,917 A | 5/1992 | Lezdey et al. |
| 5,164,372 A | 11/1992 | Matsuo et al. |
| 5,290,762 A | 3/1994 | Lezdey et al. |
| 5,521,183 A | 5/1996 | Woodward et al. |
| 6,277,846 B1 | 8/2001 | Woodward et al. |
| 6,583,155 B2 | 6/2003 | Butler et al. |
| 6,723,354 B1 | 4/2004 | Ruseler-van Embden et al. |
| 6,936,606 B2 | 8/2005 | Bekkali et al. |
| 7,312,211 B2 | 12/2007 | Bekkali et al. |
| 7,514,438 B2 | 4/2009 | Hulme et al. |
| 8,852,569 B2 | 10/2014 | Lerner et al. |
| 2002/0035108 A1 | 3/2002 | Gu et al. |
| 2002/0055497 A1 | 5/2002 | Butler et al. |
| 2003/0069240 A1 | 4/2003 | Breitenbucher et al. |
| 2005/0215618 A1 | 9/2005 | Serebruany |
| 2006/0216290 A1 | 9/2006 | Golz et al. |
| 2006/0276402 A1 | 12/2006 | Schmaier et al. |
| 2007/0117785 A1 | 5/2007 | Butler et al. |
| 2008/0213252 A1 | 9/2008 | Lerner et al. |
| 2008/0214451 A1 | 9/2008 | Kuliopulos et al. |
| 2012/0073001 A1* | 3/2012 | Dong ............... A61K 31/46 800/3 |
| 2014/0303231 A1 | 10/2014 | Dong et al. |

FOREIGN PATENT DOCUMENTS

| | | |
|---|---|---|
| WO | 2000/069485 A1 | 11/2000 |
| WO | 2001/078706 A2 | 10/2001 |
| WO | 2004/080372 A2 | 9/2004 |
| WO | 2008/028301 A1 | 3/2008 |
| WO | 2008/086069 A1 | 7/2008 |
| WO | 2014/113564 A1 | 7/2014 |

OTHER PUBLICATIONS

Azimi et al., "Substance P activates Mas-related G protein-coupled receptors to induce itch." Journal of Allergy and Clinical Immunology 140(2):447-453 (2017).
Conus et al., "Cathepsins: Key Modulators of Cell Death and Inflammatory Responses", Biochem Pharmacol, 76 (11):1374-1382 (2008).
Kamohara et al., "Identification of MrgX2 as a human G-protein-coupled receptor for proadrenomedullin N-terminal peptides." Biochemical and Biophysical Research Communications 330(4):1146-1152 (2005).
Kuraishi et al., "Scratching behavior induced by pruritogenic but not algesiogenic agents in mice." European Journal of Pharmacology 275(3):229-233 (1995).
Maeno et al., "Distribution of the substance P receptor (NK-1 receptor) in the central nervous system." Molecular Brain Research 18(1):43-58 (1993).
Regoli et al., "Receptors and antagonists for substance P and related peptides." Pharmacological Reviews 46 (4):551-599 (1994).
Robas et al., "MrgX2 is a high potency cortistatin receptor expressed in dorsal root ganglion." Journal of Biological Chemistry 278(45):44400-44404 (2003).
Rost et al., "Neurokinin 1 receptor antagonists—between hope and disappointment." Medizinische Monatsschrift fur Pharmazeuten 29(6):200-205 (2006) (Abstract Included).
Shimada et al., "Scratching behavior in mice induced by the proteinase-activated receptor-2 agonist, SLIGRL-NH 2." European Journal of Pharmacology 530(3):281-283 (2006).

(Continued)

*Primary Examiner* — Jeanette M Lieb
(74) *Attorney, Agent, or Firm* — Nixon Peabody, LLP

(57) ABSTRACT

Embodiments described herein relates to compositions and methods of preventing and/or treating itch in a subject using a therapeutically effective amount of a MRG receptor antagonist. e.g., a tripeptide QWF. In one embodiment, the itch is a non-histamine mediated itch.

8 Claims, 13 Drawing Sheets
Specification includes a Sequence Listing.

(56) References Cited

OTHER PUBLICATIONS

Shults et al., "A comparison of the anatomical distribution of substance P and substance P receptors in the rat central nervous system" Peptides 5(6):1097-1128 (1984).
Tatemoto et al., "Immunoglobulin E-independent activation of mast cell is mediated by Mrg receptors." Biochemical and Biophysical Research Communications 349(4):1322-1328 (2006).
Wahlgren et al., "Patients' perception of itch induced by histamine, compound 48/80 and wool fibres in atopic dermatitis." Acta Dermato-Venereologica 71(6):488-494 (1991).
Al-Ani et al., "Modified proteinase-activated receptor-1 and-2 derived peptides inhibit proteinase-activated receptor-2 activation by trypsin." Journal of Pharmacology and Experimental Therapeutics 300(2)702-708 (2002).
Al-Ani et al., "Proteinase-activated receptor 2: differential activation of the receptor by tethered ligand and soluble peptide analogs." Journal of Pharmacology and Experimental Therapeutics 302(3):1046-1054 (2002).
Andoh et al., "Nitric oxide enhances substance P-induced itch-associated responses in mice" Br J Pharmacol., 138 (1):202-208 (2003).
Andoh et al., "Substance P induction of itch-associated response mediated by cutaneous NK1 tachykinin receptors in mice." Journal of Pharmacology and Experimental Therapeutics 286(3):1140-1145 (1998).
Bader et al., "Mas and Its Related G Protein-Coupled Receptors, Mrgprs." Pharmacological Reviews 66 :4):1080-1105 (2014).
Biro et al., "How Best to Fight that nasty itch—From new insights into the neuroimmunological, neuroendocrine, and neurophysiological basesof pruritus to novel therapeutic approaches", Experimental Dermatology, 14(3):225-240 (2005).
Covic et al. "Activation and inhibition of G protein-coupled receptors by cell-penetrating membrane-tethered peptides." PNAS 99(2):643-648 (2002).
Database WPI Week 200271, Derwent Publications Ltd., London, GB; AN 2002-663986, XP002479657 & JP 2002 265324 A (Ichimaru Pharcos Inc), Sep. 18, 2002.
Database WPI Week 200669, Derwent Publications Ltd., London, GB; AN 2006-664363, XP002479658 & JP 2006 257059 A, Sep. 28, 2006.
Desai et al., "An orally active reversible inhibitor of cathepsin S inhibits human trans vivo delayed-type hypersensitivity", European Journal of Pharmacology, 538:168-174 (2006).
Dong et al., "A diverse family of GPCRs expressed in specific subsets of nociceptive sensory neurons." Cell 106 (5):619-632 (2001).
Fujisawa et al., "Expression of Mas-related gene X2 on mast cells is upregulated in the skin of patients with severe chronic urticaria." Journal of Allergy and Clinical Immunology 134(3):622-633 (2014).
Grice et al., "The SAR of 4-substituted (6,6-bicyclic) piperidine cathepsin S inhibitors", Bioorg Med Chem Lett.,16 (8):2209-2212 (2006).
Hagermark et al., "Flare and itch induced by substance P in human skin." Journal of Investigative Dermatology 71 (4):233-235 (1978).
Herndon, "Itching: The Pathophysiology of Pruritus", Int. J. Derm., 14:465-484 (1975).
Hollenberg et al., "Proteinase-activated receptor-4: evaluation of tethered ligand-derived peptides as probes for receptor function and as inflammatory agonists in vivo." British Journal of Pharmacology 143(4):443-454 (2004).
Ikoma et al., "The Neurobiology of itch", Nature Reviews Neurosci., 7:535-547 (2006).
Johanek et al., "A Role for Polymodal C-fiber Afferents in Nonhistaminergic Itch", 28:7659-7669 (2008).
Kahn et al., "Protease-activated receptors 1 and 4 mediate activation of human platelets by thrombin." Journal of Clinical Investigation 103(6):879-887 (1999).
Kasuda et al., "Inhibition of PAR4 Signaling Mediates Ethanol-Induced Attenuation of Platelet Function in Vitro." Alcoholism: Clinical and Experimental Research 30(9):1608-1614 (2006).
Kutsukake et al., "Venomous protease of aphid soldier for colony defense", PNAS, 101(31):11338-11343 (2004).
Lembo et al., "Proenkephalin A gene products activate a new family of sensory neuron-specific GPCRs." Nature Neuroscience 5(3):201-209 (2002).
Liu et al., "Mechanisms of itch evoked by ß—alanine." Journal of Neuroscience 32(42):14532-14537 (2012).
Liu et al., "Sensory neuron-specific GPCR Mrgprs are itch receptors mediating chloroquine-induced pruritus." Cell 139 (7):1353-1365 (2009).
Liu et al., "The distinct roles of two GPCRs, MrgprC11 and PAR2, in itch and hyperalgesia." Science Signaling 4(181): ra45 (2011).
McNeil et al., "Identification of a mast-cell-specific receptor crucial for pseudo-allergic drug reactions." Nature 519 (7542):237-241 (2015).
McNeil et al., "Inhibition Mast Cell Activation by Targeting the Orphan GPCR MrgprX2" Case ID: C11779 Mast Cell Activation Target for Immunotherapy Research, Johns Hopkins University, Web Published Oct. 7, 2014.
Namer et al., "Separate peripheral pathways for pruitus in man", 100:2062-2069 (2008).
Palermo et al., "Cysteine cathepsin proteases as pharmacological targets in cancer", Trends Pharmacol Sci., 29 (1):22-28 (2008).
Reddy et al., "Cowhage evoked itch is mediated by a novel cystine protease—a ligand protease activated recptors" J Neurosci., 28(17):4331-4335 (2008).
Schemann et al., "The mast cell degranulator compound 48/80 directly activates neurons." PLoS One 7(12):e52104 ;2012).
Solinski et al., "Pharmacology and Signaling of MAS-Related G Protein-Coupled Receptors." Pharmacological Reviews 66(3):570-597 (2014).
Steinhoff et al., "Proteinase-activated receptor-2 mediates itch: a novel pathway for pruritus in human skin." Journal of Neuroscience 23(15):6176-6180 (2003).
Steinhoff et al., "Tachykinins and their receptors: contributions to physiological control and the mechanisms of disease." Physiological Reviews 94(1):265-301 (2014).
Subramanian et al., Mas-related gene X2 (MrgX2) is a novel G protein-coupled receptor for the antimicrobial peptide LL-37 in human mast cells: resistance to receptor phosphorylation, desensitization, and internalization. The Journal of Biological Chemistry 286(52):44739-44749 (2011).
Subramanian et al., "β-Defensins activate human mast cells via Mas-related gene X2." The Journal of Immunology 191(1):345-352 (2013).
Summerfield et al., "Pain, itch and endorphins", Br. J. Dermatol., 105:725-726 (1981).
Thurmond et al., "Identification of a potent and selective noncovalent cathepsin S inhibitors", J Pharmacol Exp Ther., 308(1):268-276 (2004).
Twycross et al., "Itch: Scratching more than the surface", Q J Med., 96:7-26 (2003).
Wallengren et al., "Topical aprepitant in clinical and experimental pruritus." Archives of Dermatology 148 (8):957-959 (2012).
Wei et al., "Pyrazole-based cathepsin S inhibitors with improved cellular potency", Boorganic & Medicinal Chemistry Letters, 17:5525-28 (2007).
Wilson et al., "The epithelial cell-derived atopic dermatitis cytokine TSLP activates neurons to induce itch." Cell 155 (2):285-295 (2013).
Wilson et al., "TRPA1 is required for histamine-independent, Mas-related G protein-coupled receptor-mediated itch." Nature Neuroscience 14(5):595-602 (2011).
Winklemann, "Pharmacologic control of pruritus", Med. Clins. N. Am.,66:1119-33 (1982).
Yosipovitch et al., "Itch" Lancet 361:690-694 (2004).

* cited by examiner

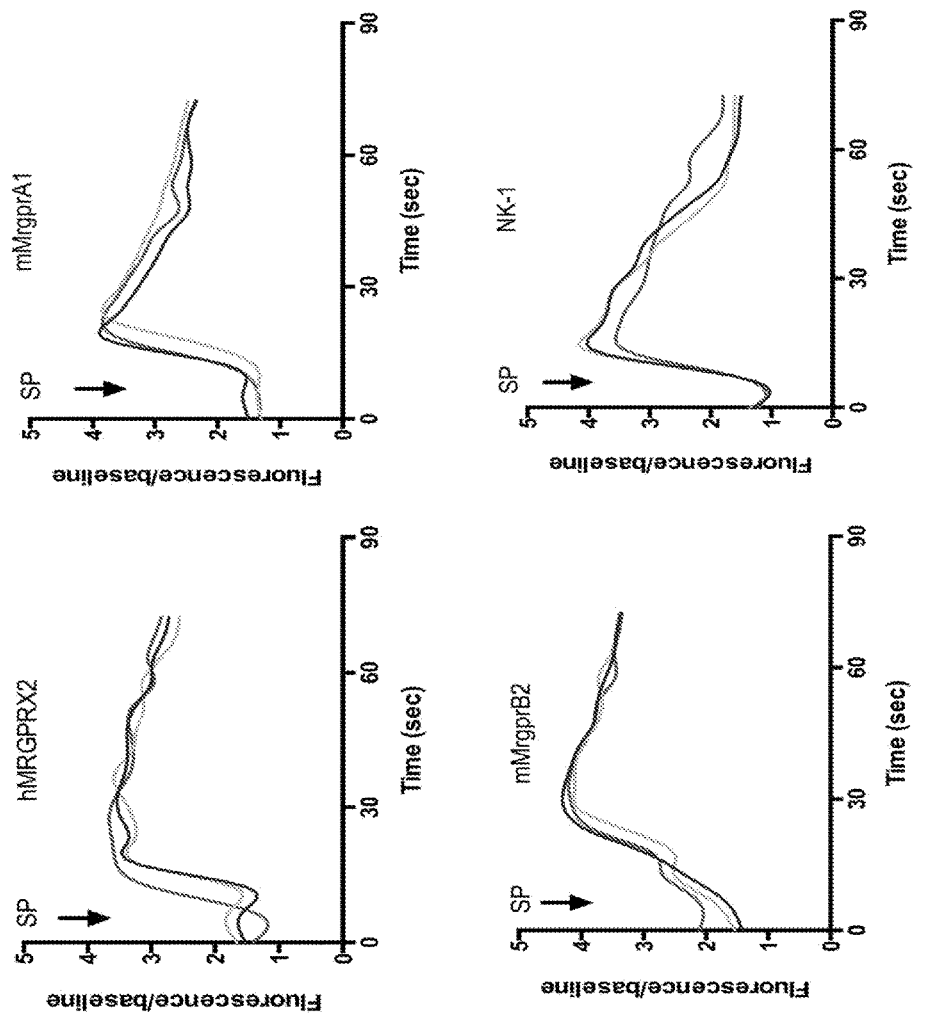
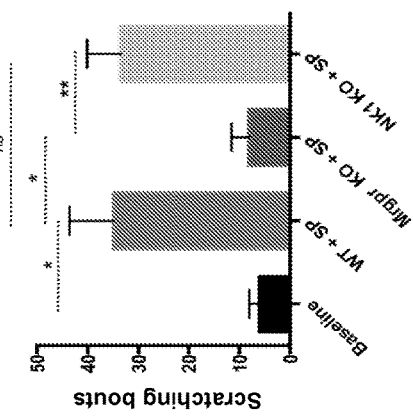
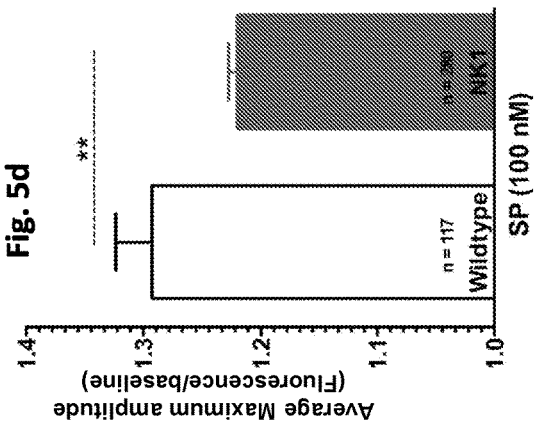

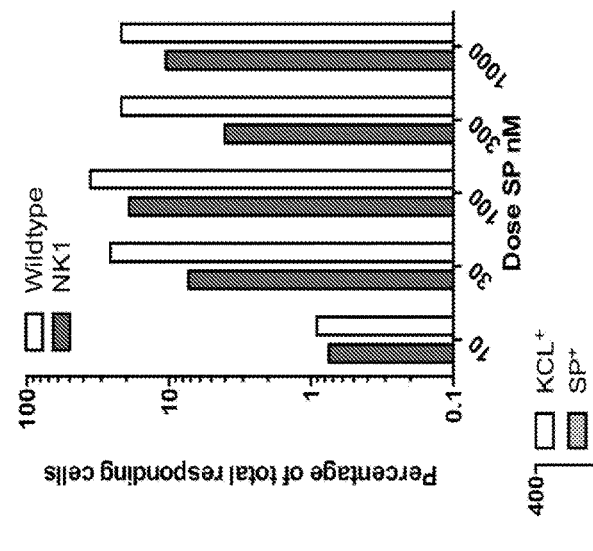
Fig. 5e
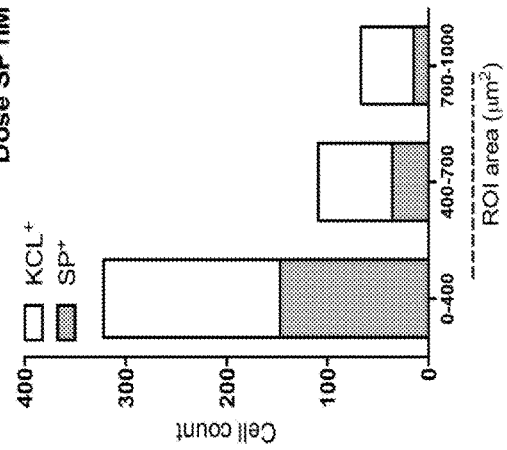
Fig. 5f
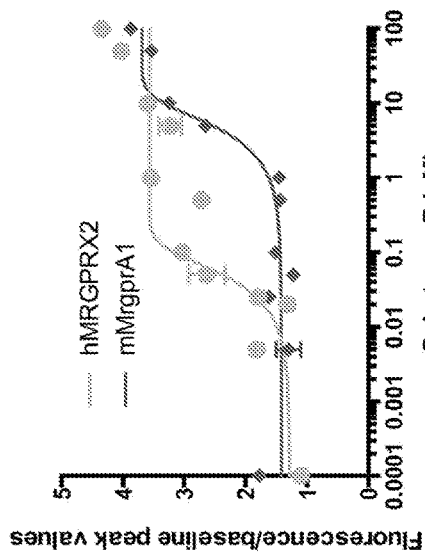
Fig. 5c
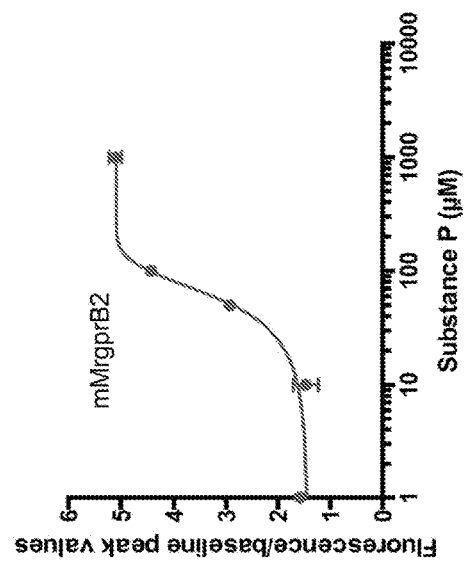

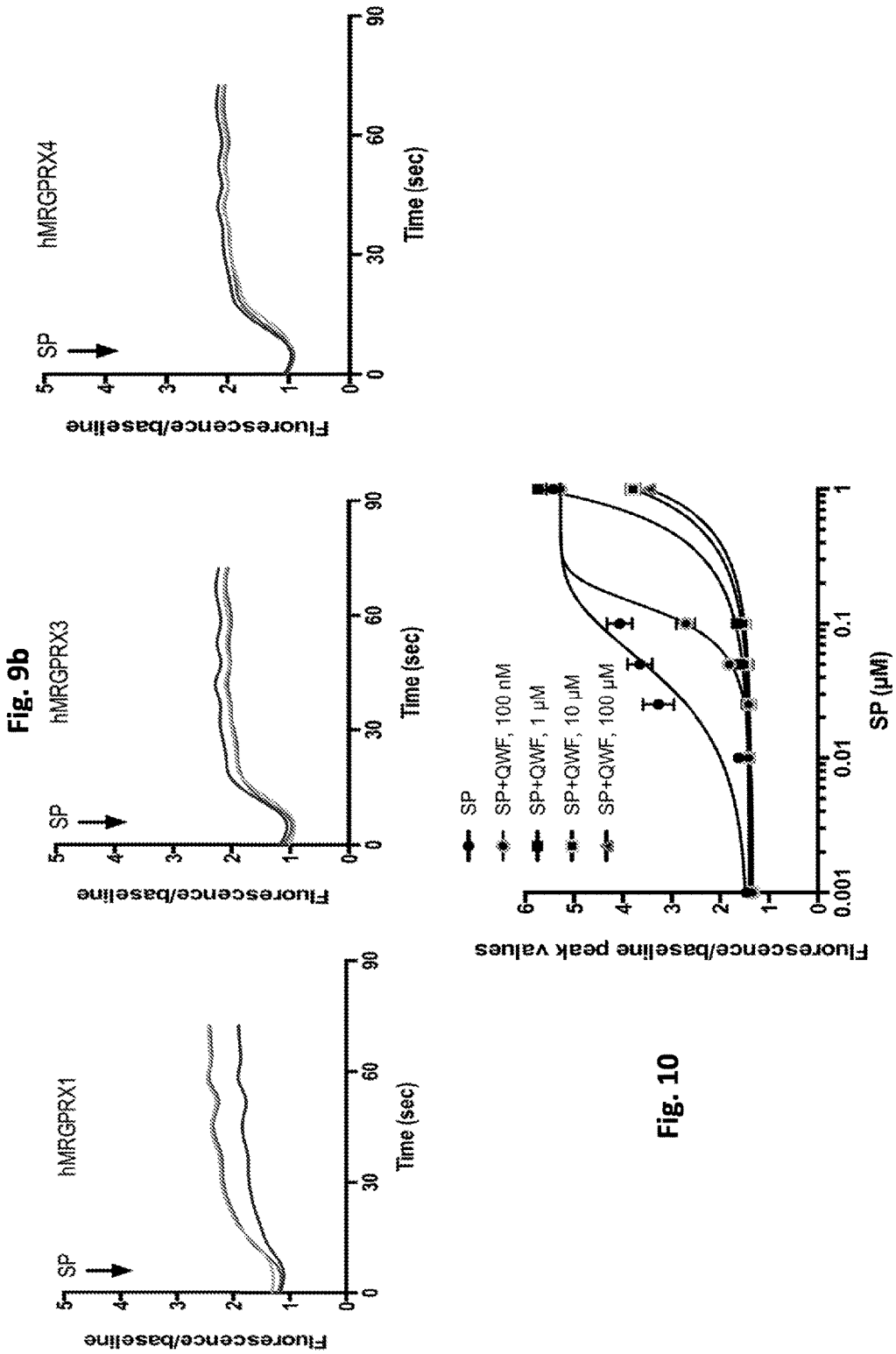

PREVENTION AND TREATMENT OF ITCH WITH AN MRGPR ANTAGONIST

CROSS REFERENCE TO RELATED APPLICATIONS

This application is a 35 U.S.C. § 371 National Phase Entry Application of International Application No. PCT/US2016/014138 filed Jan. 20, 2016, which designates the U.S., and which claims benefit under 35 U.S.C. § 119 of the U.S. Provisional Application No. 62/105,420 filed Jan. 20, 2015, the contents, the contents of each of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 7, 2016, is named 030258-084271-PCT_SL.txt and is 1,805 bytes in size.

GOVERNMENT SUPPORT

This invention was made with Government support under Grant No.: AR057744 awarded by the National Institutes of Health. The Government has certain rights in the invention.

BACKGROUND

Itch, or pruritus, is the unpleasant sensation that leads to a desire to scratch and is a common and distressing symptom in a variety of conditions and diseases. Itch also typically a symptom/sensation that occurs in certain medical conditions, peripheral diseases and disorders such as allergic conjunctivitis, allergic rhinitis, hemorrhoids, and dermatoses of fungal, allergic and non-allergic origin, and in various inflammation-related diseases and disorders. Itching can also be a major symptom of many systemic diseases such as, Hodgkin's disease, chronic renal failure, polycythema vera, hyperthyroidism and cholestasis (see, for example, Herndon, J. H. Jr., Int. J. Derm. 14:465-484 (1975); Winkelmann, R. K., Med. Clins. N. Am. 66:1119-1133 (1982). In addition, senile itch is without an obvious cause, except perhaps xerosis, occurs in more than half of the population aged 70 years (Twycross et al., QJM. 2003, 96:7-26). In all cases, chronic severe generalized itch can be disabling.

Recognition that itch is of major medical significance is driving research into the basic mechanisms that underlie this sensory phenomenon. Progress is being made on identification of periphery and central mediators, receptors and channels that contribute to itch.

The sensation of itch is known to be mediated by two distinct non-overlapping populations of cutaneous nerve fibers that evoke comparable degrees of itch (B. Namer et al., J. Neurophysiol. 100:2062-2069 (2008); L. M. Johanek et al., J. Neurosci. 28:7659-7669 (2008)). One set of fibers, the mechano-insensitive population, is more responsive to histamine than to cowhage. The other set is mechanosensitive and is more responsive to cowhage than to histamine (B. Namer et al.; L. M. Johanek et al., supra). Histamine is a classical mediator of itch and is associated with a wheal and flare. Since most clinical itches do not have a wheal or flare and do not respond to antihistamines, histamine is not thought to contribute to most itches (A. Ikoma et al., Nature Reviews Neurosci. 7, 535-547 (2006)). Cowhage refers to a tropical legume or, in this case, the loose hairs that cover the pods of *Mucuna pruriens*, and cowhage evoke itch. The active component of cowhage is mucunain, a cysteine protease that serves as a ligand for protease-activated receptors (PARs) 2 and 4 (V. B. Reddy et al., J. Neurosci. 28:4331-4335 (2008)).

Itching can be elicited by chemical, electrical, mechanical and thermal stimulation. So far no morphological structure has been identified as a specific receptor for the itch sensation, but it is assumed that itch receptors are linked to the free nerve endings of C-fibers close to the dermo-epidermal junction. The impulses set up in the thin, non-myelinated, slowly conducting C-fibers enter the spinal cord via the dorsal horn, then ascend in the contralateral spinothalmic tract, pass via the thalamus and end in the somatosensory cortex of the post-central gyrus. Itching and pain are related phenomena, and it was previously believed that itching was equal to sub-threshold pain, i.e. with increased activity in the C-fibers the perceived sensation changed from itching to pain. Although itch was once thought to be a subliminal form of pain (intensity theory), current evidence points to separate sensory neuronal systems mediating the two modalities. First, pain and itch are dissociable. Pain and itch evoke different motor responses, scratching for itch and withdrawal for pain. Second, based on clinical observations, systemically-administered opioids have a dichotomous effect on these two sensory modalities. µ-opioid receptor agonists reduce pain but can cause itch. Furthermore, antagonizing the central µ-opioid receptors, for example with naloxone or naltrexone, suppresses pruritus and at the same time may lower the pain threshold (Summerfield et al. Br. J. Dermatol. 1981, 105:725-6).

Currently the standard treatment for itch is the administration of anti-histamines. However, not all forms of itch are responsive to anti-histamines. For example, chole stasis is characterized by generalized itch, which is not responsive to H1-antihistamines, indicating that histamine is probably not the major mediator involved. Approximately 25% of patients with uremia (chronic renal failure) suffer from severe itch unresponsive to H1-antihistamines or dialysis. However, since histamine was believed to be the primary mediator of the itch sensation, conventional itch therapy involves H1-antihistamines as a first-line medication although antihistamines have no general anti-pruritic effect, and in many instances they are either ineffective or only partially effective.

Clearly among all the topical and systemic agents that suppress itching in selected clinical settings there is no universally effective anti-pruritic drug. There is an urgent need for therapeutic agents for itch that do not target the histamine pathway. Such therapeutic agents would target non-histamine mediated itch.

SUMMARY

Embodiments described herein are based on the surprising discovery that the orphan receptors, the MRG receptors, participate in histamine-independent itch elicited by Substance P. Substance P (SP) is an inflammatory neuropeptide that is implicated in eliciting the itch sensation. While the classic receptor for SP is neurokinin-1 (NK-1), the inventors have found that SP activates other receptors in addition to NK1. In particular, the inventors have determined that SP activates the mouse receptor MrgprA1 and the homologous human receptor MRGPRX2, which are necessary to induce itch. Mice that are knockout for MrgprA1 exhibited no response to SP.

Although SP is known to provoke itch, a functional link between Mrgprs and SP has never been considered. The inventors show that SP provokes itch via activation of Mrgprs rather than NK-1, its classical receptor. Human MRGPRX2, implicated in pseudo-allergic drug reactions, was also activated by substance P. More importantly, the inventors have identified a potent tripeptide antagonist of these MRG receptors. The tripeptide inhibits both itch provoked by SP in mice and drug-induced degranulation of human mast cells. Antagonists of human MRGPRX2 would be of benefit in the treatment of itch and drug reactions.

Accordingly, it is the objective of this disclosure to provide antagonists of MRG receptors for (1) use in the manufacture of medicament for the prevention and/or treatment of itch; and (2) use in a method for the prevention and/or treatment of itch.

Accordingly, it is the objective of this disclosure to provide antagonists of MRG receptors for use in the manufacture of medicament for providing relief to the unpleasant itch sensation.

Accordingly, in one embodiment, provided herein is a use of an MRG receptor antagonist in the manufacture of medicament for the prevention of itch.

In one embodiment, medicament for the prevention of itch can also be used for the treatment of itch. In one embodiment, provided herein is a use of an MRG receptor antagonist in the manufacture of medicament for the treatment of itch.

In one embodiment, provided herein is a use of an MRG receptor antagonist in the manufacture of medicament for the prevention and/or treatment of itch, wherein the itch is not a symptom or sensation associated with psoriasis and atopic dermatitis.

In one embodiment, provided herein is a use of an MRG receptor antagonist in the manufacture of medicament for the prevention and/or treatment of itch, wherein the itch is non-histamine mediated.

In one embodiment, provided herein is a use of an MRG receptor antagonist for the prevention and/or treatment of itch. In one embodiment, the itch is not a symptom or sensation associated with psoriasis and atopic dermatitis. In another embodiment, the itch is non-histamine mediated.

In one embodiment, provided herein is a use of an MRG receptor antagonist for the prevention and/or treatment of itch, wherein the itch is not a symptom or sensation associated with psoriasis and atopic dermatitis.

In one embodiment, provided herein is a use of an MRG receptor antagonist for the prevention and/or treatment of itch, wherein the itch is non-histamine mediated.

In one embodiment, provided herein is a use of a tri-peptide QWF, (Gln-Trp-Phe) or an analog or a derivative thereof in the manufacture of medicament for the prevention of itch. In one embodiment, medicament for the prevention of itch can also be used for the treatment of itch.

In one embodiment, provided herein is a use of a tri-peptide QWF, (Gln-Trp-Phe) or an analog or a derivative thereof in the manufacture of medicament for the prevention and/or treatment of itch.

In one embodiment, provided herein is a use of [Boc-Gln-D-Trp(Formyl)-Phe benzyl ester] or the tri-peptide QWF [Gln-D-Trp(Formyl)-Phe benzyl ester] or an analog or a derivative thereof in the manufacture of medicament for the prevention and/or treatment of itch.

In one embodiment, the itch is not a symptom or sensation associated with psoriasis and atopic dermatitis. In another embodiment, the itch is non-histamine mediated.

Accordingly, in one embodiment, provided herein is a use of a tri-peptide QWF, (Gln-Trp-Phe) or an analog or a derivative thereof in the manufacture of medicament for the prevention and/or treatment of itch, wherein the itch is not a symptom or sensation associated with psoriasis and atopic dermatitis.

In one embodiment, provided herein is a use of a tri-peptide QWF, (Gln-Trp-Phe) or an analog or a derivative thereof in the manufacture of medicament for the prevention and/or treatment of itch, wherein the itch is non-histamine mediated.

In one embodiment, provided herein is a use of a tri-peptide QWF, (Gln-Trp-Phe) or an analog or a derivative thereof for the prevention and/or treatment of itch.

In one embodiment, provided herein is a use of [Boc-Gln-D-Trp(Formyl)-Phe benzyl ester] or the tri-peptide QWF [Gln-D-Trp(Formyl)-Phe benzyl ester] or an analog or a derivative thereof for the prevention and/or treatment of itch.

In one embodiment, provided herein is a use of a tri-peptide QWF, (Gln-Trp-Phe) or an analog or a derivative thereof for the prevention and/or treatment of itch, wherein the itch is not a symptom or sensation associated with psoriasis and atopic dermatitis.

In one embodiment, provided herein is a use of a tri-peptide QWF, (Gln-Trp-Phe) or an analog or a derivative thereof for the treatment and/or prevention of itch, wherein the itch is non-histamine mediated.

In one embodiment, provided herein is a method of preventing or treating itch in a subject, the method comprising administering a therapeutically effective amount of an MRG receptor antagonist to the subject. In one embodiment, a therapeutically effective amount of a composition comprising an MRG receptor antagonist is administered to the subject.

In one embodiment, provided herein is a method of treating a disease or disorder having itch as a symptom or sensation associated with the disease or disorder in a subject, the method comprising administering a therapeutically effective amount of an MRG receptor antagonist to the subject. In one embodiment, a therapeutically effective amount of a composition comprising an MRG receptor antagonist is administered to the subject.

In one embodiment, provided herein is a method of preventing or treating itch in a subject, the method comprising administering a therapeutically effective amount of a tri-peptide QWF, (Gln-Trp-Phe) or an analog or a derivative thereof to the subject. In one embodiment, a therapeutically effective amount of a composition comprising a tri-peptide QWF, (Gln-Trp-Phe) or an analog or a derivative thereof is administered to the subject.

In one embodiment, provided herein is a method of treating a disease or disorder having itch as a symptom or sensation associated with the disease or disorder in a subject, the method comprising administering a therapeutically effective amount of a tri-peptide QWF, (Gln-Trp-Phe) or an analog or a derivative thereof to the subject. In one embodiment, a therapeutically effective amount of a composition comprising a tri-peptide QWF, (Gln-Trp-Phe) or an analog or a derivative thereof is administered to the subject.

In one embodiment, provided herein is a method of treating a disease or disorder having itch as a symptom or sensation associated with the disease or disorder in a subject, the method comprising administering a therapeutically effective amount of [Boc-Gln-D-Trp(Formyl)-Phe benzyl ester] or the tri-peptide QWF [Gln-D-Trp(Formyl)-Phe benzyl ester] or an analog or a derivative thereof to the subject.

In one embodiment, a therapeutically effective amount of a composition comprising [Boc-Gln-D-Trp(Formyl)-Phe benzyl ester] or the tri-peptide QWF [Gln-D-Trp(Formyl)-Phe benzyl ester] or an analog or a derivative thereof is administered to the subject.

In one embodiment, provided herein is a method of preventing or treating one or more symptom or sensation arising from an irritation, urticarial (hives), pain, inflammation, asthma, allergy, allergic rhinitis, inflammatory bowel disease or irritable bowel disease in a subject, the method comprising administering a therapeutically effective amount of an MRG receptor antagonist to the subject. In one embodiment, a therapeutically effective amount of a composition comprising an MRG receptor antagonist is administered to the subject.

In one embodiment, provided herein is a method of preventing or treating one or more symptom or sensation arising from an irritation, urticarial (hives), pain, inflammation, asthma, allergy, allergic rhinitis, inflammatory bowel disease or irritable bowel disease in a subject, the method comprising administering a therapeutically effective amount of a tri-peptide QWF, (Gln-Trp-Phe) or an analog or a derivative thereof is administered to the subject. In one embodiment, a therapeutically effective amount of a composition comprising a tri-peptide QWF, (Gln-Trp-Phe) or an analog or a derivative thereof is administered to the subject.

In one embodiment, provided herein is a method of preventing or treating one or more symptom or sensation arising from an irritation, urticarial (hives), pain, inflammation, asthma, allergy, allergic rhinitis, inflammatory bowel disease or irritable bowel disease in a subject, the method comprising administering a therapeutically effective amount of a tri-peptide QWF, (Gln-Trp-Phe) or an analog or a derivative thereof is administered to the subject. In one embodiment, a therapeutically effective amount of a composition comprising a tri-peptide QWF, (Gln-Trp-Phe) or an analog or a derivative thereof is administered to the subject.

In one embodiment of any uses or methods described, the itch is not a symptom or sensation associated with psoriasis and atopic dermatitis. In another embodiment of any uses or methods described, the itch is non-histamine mediated.

In one embodiment of any uses or methods described, the MRG receptor is MRGPRX1.

In one embodiment of any uses or methods described, the MRG receptor is MRGPRX2.

In one embodiment of any uses or methods described, the MRG receptor antagonist also antagonizes an NK1 receptor.

In one embodiment of any uses or methods described, the MRG receptor antagonist is a tri-peptide QWF, (Gln-Trp-Phe) or an analog or a derivative thereof.

In one embodiment of any uses or methods described, the tri-peptide QWF is [Boc-Gln-D-Trp(Formyl)-Phe benzyl ester] or the tri-peptide QWF [Gln-D-Trp(Formyl)-Phe benzyl ester] or an analog or a derivative thereof.

In one embodiment of any uses or methods described, the itch is a symptom or sensation associated with a disease or disorder selected from anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen planopilaris, frontal fibrosing alopecia, central centrifugal scarring alopecia, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma.

In another embodiment, the uses and methods described herein are also applicable to itch with no known etiology.

In one embodiment of any uses or methods described, the itch is a non-histamine mediated itch. As used herein, a "non-histamine mediated itch" refers to an itch sensation that is not alleviated by antihistamines and is not elicited via histaminergic pathway.

In one embodiment of any methods described, the subject is any mammal that expresses a MRG receptor and/or an NK1 receptor. For example, a human, a dog, a cat, pig, goat, a canine, and a horse, etc.

In one embodiment of any uses or methods described, the MRG receptor antagonist is administered topically to the subject.

In one embodiment of any uses or methods described, the MRG receptor antagonist is contained in a topical formulation and the topical formulation is selected from the group consisting of a solution, a suspension, a lotion, a gel, a cream, a foam, a eutectic mixture, an ointment and an emulsion.

In one embodiment of any uses or methods described, the formulation is associated with a skin patch device.

In one embodiment of any uses or methods described, the MRG receptor antagonist is administered systemically to the subject.

In one embodiment of any uses or methods described, the administration is selected from the group consisting of oral, parenteral, introatracheal, intrathecal, intracranial, intrarectal, intranasal, intravenous, intramuscular, intraperitoneal, intracerebrospinal, subcutaneous, intra-epidermal, intra-arterial and intrasynovial administration.

In one embodiment of any methods described, the method further comprising administering an additional agent to the subject in combination with the MRG receptor antagonist.

In one embodiment of any uses or methods described, the additional agent is selected from the group consisting of a mast cell stabilizer, a TRP channel inhibitor or activator, an inhibitor of a nerve growth factor receptor, e.g., TrkA or an inhibitor of a cytokine, e.g., thymic stromal lymphopoietin or interleukin-4 or its receptor or interleukin-31 or its receptor or a calcinuerin inhibitor or a corticosteroid.

In one embodiment of any uses or methods described, the additional agent has anti-itch properties.

In one embodiment of any uses or methods described, the MRG receptor antagonist or tri-peptide QWF, (Gln-Trp-Phe) or an analog or a derivative thereof can be administered in conjunction with other medicaments associated with the respective medical condition. Examples include menthol and phenol, calamine, topical antihistamines, local anesthetics, capsaicin, strontium nitrate, H1-receptor antagonists, H2-receptor antagonists, H4-receptor antagonists, doxepin, ondansetron, paroxetine, and mirtazapine. Other medicaments include but are not limited to, for dry skin: emollient cream; for cholestasis: colestyramine, rifampicin, opioid antagonists, androgens; for uremia: dialysis, UVB phototherapy and for paraneoplasia: paroxetine.

In one embodiment of any uses or methods described, the additional agent having anti-itch properties is a cysteine protease.

In one embodiment of any uses or methods described, the cysteine protease used in the methods of preventing and/or treating itch is a cathepsin.

BRIEF DESCRIPTION OF THE DRAWINGS

FIGS. 5a-5f show that Substance P (SP) activates Mrgprs to provoke itch.

FIG. 5a. The mouse cheek model was used to quantify SP-provoked scratching bouts in wild type (WT), Mrpgr cluster Δ-/- mice (Mrgpr KO), and NK1 Δ-/- (NK1 KO) mice. 10 μL of SP (1 mM) was delivered to the cheek via intradermal injection. SP-provoked itch was not decreased in NK1 mice compared to WT (p=0.90, N=7 mice/group). SP-provoked itch was significantly decreased in Mrpgr mice compared to WT (p=0.022, N=7 mice/group) and NK1 mice (p=0.007, N=7 mice/group).

FIG. 5b. HeLa cells were transfected with cDNAs encoding NK1, human MRGPRX2, mouse MrgprA1 and mouse MrgprB2. Intracellular calcium concentration traces [$Ca^{2+}$]i were measured by ratiometric FURA-2 imaging after the cells are treated with SP. Concentration of SP was calculated based on $EC_{50}$s for each receptor. 10 nM, 500 nM, 10 μM, and 50 μM SP were used for NK1, human MRGPRX2, mouse MrgprA1, and mouse MrgprB2 transfected cells respectively. Each trace is a response from a unique transfected HeLa cell.

FIG. 5c. Concentration-effect curves of SP on human MRGPRX2 (expressed on human mast cells and dorsal root ganglion neurons), mouse MrgprA1 (expressed on mouse dorsal root ganglion neurons), and mouse MrgprB2 (expressed on mouse mast cells). SP activity on Mrgprs was as follows human MRGPRX2>mouse MrgprA1>mouse MrgprB2.

FIG. 5d and FIG. 5e. Dorsal root ganglion neurons (DRGs) from WT and NK1 mice were cultured and treated with SP.

FIG. 5f. Binning the size of SP responsive NK1 DRGs revealed that mainly small (soma of <600 μm) and to a lesser extent, medium sized (soma of 600-1200 μm) NK1 DRG neurons were activated by SP. Data expressed as mean±S.E.M; Two-tailed unpaired Student's t-test was used to determine significance in statistical comparisons, and differences were considered significant at p≤0.05. ns, p>0.05, *p≥0.05. **p≥0.01.

FIG. 6a, HeLa cells were transfected with cDNAs encoding NK1, human MRGPRX2, mouse MrgprA1, and mouse MrgprB2. Cells were pretreated with the NK1 inhibitors for 10 minutes, SP added as indicated by the arrow, and intracellular calcium [Ca2+]i determined by ratiometric Fura-2 imaging Concentration of SP and antagonists were calculated based on EC50s for each receptor (FIG. 5c). 5 nM, 500 nM, 5 μM SP and 1 μM, 1 μM, 10 μM concentration of the inhibitors were used for NK1, human MRGPRX2 and mouse MrgprA1 transfected cells respectively. Each trace is a response from a different cell. L733060 and aprepitant do not inhibit the activation of Mrgprs by SP. QWF, a tripeptide NK1 inhibitor, blocks the activation of Mrgprs in addition to NK1.

FIG. 6b. QWF inhibits activation of cultured NK1 DRGs. The trace demonstrates averages of 49 DRG neurons. A high proportion of these cells were AITC and/or capsaicin responsive suggesting that they are of TRPV1 lineage.

FIG. 6c. The difference between the activation amplitude of SP-responsive NK1 DRGs was calculated in the presence and absence of QWF. QWF significantly decreases the activation amplitude induced by SP.

FIG. 6d. The cheek model was used to quantify SP-provoked scratching bouts in C57BL/6 mice. A total of 10 μl of SP+L733060 or QWF (500 μM of each substance) was injected intradermally. QWF significantly decreases SP-provoked itch but L733060 does not (p=0.022, N=7 mice/group). Data expressed as mean±S.E.M; Two-tailed unpaired Student's t-test was used to determine significance in statistical comparisons, and differences were considered significant at p≤0.05. ns, p>0.05, *p≤0.05, ****p≤0.0001.

FIG. 7a. Cells were treated with SLIGRL (SEQ ID NO: 7) (10 μM). QWF (1 μM) inhibits activation of Mrgprs by SLIGRL (SEQ ID NO: 7) (Also See FIG. 10).

FIG. 7b. Cells were treated with compound 48/80 (1 μM). QWF (1 μM) inhibits activation of Mrgprs by compound 48/80.

FIG. 7c. Cells were treated with chloroquine (CQ) (100 μM) which activates human MRGPRX1 and mouse MrgprA3 to provoke itch. QWF (100 μM) does not inhibit activation of human MRGPRX1 or human MRGPRA3 by CQ.

FIG. 7d. The cheek model was used to quantify scratching bouts provoked by SLIGRL (SEQ ID NO: 7) and compound 48/80 in C57BL/6 mice. A total of 10 μL of QWF+SLIGRL (SEQ ID NO: 7) or compound 48/80 was dissolved in the same vehicle (500 μM of each substance) and delivered to the cheek by intradermal injection. QWF significantly decreased SLIGRL (SEQ ID NO: 7) and compound 48/80-provoked itch (p=0.019 and p=0.002 respectively, N=7 mice/group). Data expressed as mean±S.E.M; Two-tailed unpaired Student's t-test was used to determine significance in statistical comparisons, and differences were considered significant at p≤0.05. *p≤0.05. **p≤0.01.

FIG. 8a. HeLa cells were transfected with cDNAs encoding human MRGPRX2 or mouse MrgprB2 and intracellular calcium concentration traces $[Ca^{2+}]i$ were measured by ratiometric FURA-2 imaging after the cells were treated with SP. QWF inhibits activation of human MRGPRX2 and mouse MrgprB2 by these medications. Each trace is a response from a unique cell.

FIG. 8b. Activation of human MRGPRX2 by fluoroquinolone antibiotics and curare-derived neuromuscular-blocking agents induces an IgE-independent mast cell degranulation implicated in the pseudo-allergic drug reactions observed with these medications. QWF significantly inhibits the degranulation induced by SP, compound 48/80, atracurium, and ciprofloxacin in human LAD2 mast cells. QWF or a derivative could potentially prevent allergic drug reactions mediated by human MRGPRX2. Data expressed as mean±S.E.M; Two-tailed unpaired Student's t-test was used to determine significance in statistical comparisons, and differences were considered significant at p≤0.05. * p≤0.05. p≤0.01. *p≤0.001. ****p≤0.0001. ns, not significant.

FIGS. 9a-9b show that SP (10 μM) does not activate hMRGPRX1, 3, and 4 or any of the mMrgprs deleted in the Mrgpr cluster Δ−/− mouse. HeLa cells were transfected with cDNAs encoding the Mrgprs deleted in the Mrgpr cluster Δ−/− mouse and hMRGPRX1, 3, and 4. Each trace is a response from a different cell.

FIG. 10 shows that QWF is a competitive antagonist of substance P on hMRGPRX2. QWF is a competitive antagonist of substance P on hMRGPRX2. Concentration-effect curves with substance P versus the indicated concentrations of QWF on a stable HEK-293 cell line expressing hMRGPRX2. HEK293 cells were transfected with a pcDNA3.1(−) vector containing MRGPRX2 cDNA and clones resistant to gentamicin (G418) were selected. The data were generated from one of those clones. The experiment was done once with each data point done in triplicate. Error bars represent+/−SEM.

DETAILED DESCRIPTION

Figure 1:
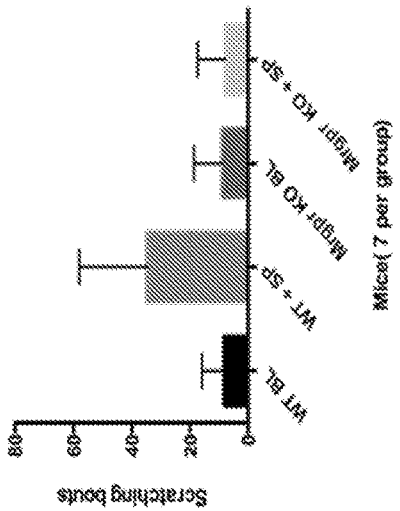
FIG. 1 shows that SP activates Mouse MrgprA1 and Human MrgprX2 in addition to NK1 receptor.

Unless otherwise explained, all technical and scientific terms used herein have the same meaning as commonly understood by one of ordinary skill in the art to which this disclosure belongs. Definitions of common terms in medicine, dermatology, cell and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Definitions of common terms in molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

It should be understood that this disclosure is not limited to the particular methodology, protocols, and reagents, etc., described herein and as such may vary. The terminology used herein is for the purpose of describing particular embodiments only, and is not intended to limit the scope of the present disclosure, which is defined solely by the claims.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example Thus, the abbreviation "e.g." is synonymous with the term "for example."

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

Definitions of Terms

As used herein, the term "itch", technically known as pruritus refers to the sensation that elicits a reflex response to scratch. Itch can be a symptom of a disease, disorder or infection, or itch can arise spontaneously, without an underlying or identifiable physiological cause, known as idiopathic pruritus.

As used herein, the term "treatment" refers to all aspects of control of itching including therapy. Control of itch includes reducing, alleviating, relieving and numbing the sensation of itch. Control of itch also includes reducing the desire to scratch.

As used herein, the term "prevent" or "prevention" refers to stopping, hindering, and/or slowing down the onset of itch sensations and symptoms, wherein the itch sensations and symptom can be associated with medical conditions or have no known etiology.

As used herein, the term "therapeutically effective amount" and grammatical variations thereof refer to sufficient quantities of the active compound that can produce the desired therapeutic effect when administered to a mammal afflicted with pruritus. The term "therapeutic effect" is used herein in a broad sense and includes prophylactic effects. Desired therapeutic effects includes but not limited to reduced sensation of itch, distraction due to the itch sensation and the desire to scratch.

As used herein, the term "antagonist" in "a MRG receptor antagonist" or "Mrgpr antagonist" refers to any organic or inorganic molecule that opposes, blocks, reduces and/or inhibits the naturally occurring signaling events elicited by the Substance P via the MRG receptor respectively. For example, an antibody or a small peptide that blocks the interaction of the Substance P via the MRG receptor, and thereby preventing the MRG receptor signaling pathway. In one embodiment, the naturally occurring signaling events elicited by the Substance P via the MRG receptor can be assayed by the $Ca^{2+}$ influxes into a cell in the presence of the antagonist as described in the Example section. In one embodiment, the antibody is a MRG receptor antagonist when the antibody prevents or inhibits the naturally occurring signaling events elicited by the Substance P via the MRG receptor in cells. In some embodiments, the inhibitory antibody to MRG receptor is a monoclonal antibody—the monoclonal antibody is a human monoclonal antibody, a mouse monoclonal antibody, or a humanized mouse monoclonal antibody; a single chain antibody; a single chain Fv (scFv) fragment; a Fab fragment; a humanized antibody; a chimeric antibody; chimeric antigen receptor (CAR); or an antibody is produced by a hybridoma cell line. In one embodiment, the MRG receptor antagonist is a MRGPRD siRNA/shRNA/RNAi or lentivirus that inhibits expression of the receptor in the cell. Such MRGPRD siRNA/shRNA/RNAi Lentivirus are commercially available, for example, from ABM®. MRGPRD siRNA/shRNA/RNAi can also be designed using the shrna design softwares such as from INVIVOGEN or GE Dharmacon using the GENECard data on MRGPRs, eg. DNA data of the MRGPRX2 gene.

As used herein, the term "antibody" is used to mean immunoglobulin molecules and functional fragments thereof, regardless of the source or method of producing the fragment. As used herein, a "functional fragment" of an immunoglobulin is a portion of the immunoglobulin molecule that specifically binds to a binding target. Thus, the term "antibody" as used herein encompasses whole antibodies, such as antibodies with isotypes that include but are not limited to IgG, IgM, IgA, IgD, IgE and IgY, and even single-chain antibodies found in some animals e.g., camels, as well as fragments that specifically bind to target. Whole antibodies or fragments thereof may be monoclonal or polyclonal, and they may be humanized or chimeric. The term "monoclonal antibody" as used herein is not limited to antibodies produced through hybridoma technology. Rather, the term "monoclonal antibody" refers to an antibody that is derived from a single clone, including any eukaryotic, prokaryotic, or phage clone, and not the method by which it is produced. The term "antibody" also encompasses functional fragments of immunoglobulins, including but not limited to Fab fragments, Fab' fragments, F(ab')2 fragments and Fd fragments. "Antibody" also encompasses fragments of immunoglobulins that comprise at least a portion of a VL and/or VH domain, such as single chain antibodies, a single-chain Fv (scFv), disulfide-linked Fvs and the like.

As used herein, "chimeric antigen receptor" or "CAR" refers to an artificially constructed hybrid polypeptide comprising an antigen-binding domain (e.g. an antigen-binding portion of an antibody (e.g. a scFV)) linked to a cell signaling and/or cell activation domain. In some embodiments the cell-signaling domain can be a T-cell signaling domain. In some embodiments, the cell activation domain can be a T-cell activation domain. CARs have the ability to redirect the specificity and reactivity of T cells and other immune cells toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fabs (instead of from an antibody, e.g., obtained from Fab libraries), in various embodiments, this scFv is fused to a transmembrane domain and then to an intracellular signaling domain. "First-generation" CARs include those that solely provide CD3zeta signals upon antigen binding, "Second-generation" CARs include those that provide both costimulation (e.g. CD28 or CD 137) and activation (CD3Q. "Third-generation" CARs include those that provide multiple costimulation (e.g. CD28 and CD 137) and activation (CD3Q). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety. The chimeric antigen receptors (CARs) can be introduced into T cells, and other immune cells such as Natural Killer (NK) cells or Natural Killer T (NKT) cells permitting the transfected cells to recognize a desired antigen. This approach equips the transfected cells with an immune receptor that does not require recognition of the major histocompatibility complex (MHC), which tumors can modify to avoid immune recognition. Moreover, upon engagement of the antibody with the targeted cancer cells, the transfected cells (T cells, NK or NKT) get activated and their killing capabilities are enhanced.

As used herein, the term "humanized" immunoglobulin or "humanized" antibody refers to an immunoglobulin comprising a human framework, at least one complementarity determining regions (CDR) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. For example, a humanized immunoglobulin would encompass a chimeric mouse variable region/human constant region antibody.

As used herein, the term "chimeric" antibody refers to an antibody whose heavy and light chains have been constructed, typically by genetic engineering, from immunoglobulin gene segments belonging to different species. For example, the variable (V) segments of the genes from a mouse monoclonal antibody can be joined to human constant (C) segments, such as gamma1 and/or gamma4. A typical therapeutic or diagnostic chimeric antibody is thus a hybrid protein comprising at least one V region (e.g., VH or VL) or the entire antigen-binding domain (i.e., VH and VL) from a mouse antibody and at least one C (effector) region (e.g., CH (CH1, CH2, CH3, or CH4) or CL or the entire C domain (i.e., CH and CL) from a human antibody, although other mammalian species can be used. In some embodiments, especially for use in the therapeutic methods of the antibodies should contain no CH2 domain.

As used herein, the term "fragments" of the antibodies include, for example, Fab, Fab', F(ab')2 and Fv. These fragments lack the Fc fragment of intact antibody, clear more rapidly from the circulation, and can have less non-specific tissue binding than an intact antibody (Wahl et al., J. Nucl. Med. 24:316-325 (1983)). These fragments are produced from intact antibodies using methods well known in the art, for example by proteolytic cleavage with enzymes such as papain (to produce Fab fragments) or pepsin (to produce F(ab')2 fragments).

The terms "RNAi" and "RNA interference" and "RNA interference agent" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g. the MRGPR gene sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, according to Jackson et al. (Id.), 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the MRGPR mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O- alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA. The Examples herein provide specific examples of RNA interfering agents, such as shRNA molecules that effectively target MRGPR gene mRNA.

In one embodiment, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells after transcription into siRNA capable of targeting, for example, MRGPR.

As used herein, the term "comprising" means that other elements can also be present in addition to the defined elements presented. The use of "comprising" indicates inclusion rather than limitation.

As used herein, a "non-histamine mediated itch" refers to a itch sensation that is not alleviated by antihistamines and is not elicited via histaminergic pathway.

Embodiments of the present disclosure are based on the discovery that the orphan receptors, the MRG receptors, participate in histamine-independent itch elicited by Substance P.

Itch is a major medical problem. Its impact on quality of life equals that of pain. It represents an unmet medical need as few effective therapies are available. Antihistamines have been found to have little clinical benefit for itch, uncovering the importance of histamine-independent pathways.

Substance P (SP) is an inflammatory neuropeptide that is implicated in eliciting the itch sensation. Substance P is known to provoke itch but a functional link between Mrgprs and substance P has not been considered. The inventors show that substance P provokes itch via activation of Mrgprs rather than neurokinin 1 (NK-1), its classical receptor Human MRGPRX2, implicated in pseudo-allergic drug reactions, was also activated by SP. SP elicited a signal transduction event via Mrgprs that led to the sensation of itch. The inventors have identified a potent tripeptide antagonist of these receptors. The tripeptide inhibits both itch provoked by substance P in mice and drug-induced degranulation of human mast cells. Therefore, targeting the MRG receptors (Mrgprs) can prevent and/or treat itch. Antagonists of human MRGPRX2 may be of benefit in the treatment of itch and drug reactions.

Accordingly, the MRG receptor and its signaling represent as targets for the prevention, inhibiting, and/or treatment of itch.

Itch or pruritus is defined as an unpleasant sensation that evokes the desire or reflex to scratch. Itches are a common problem and can be localized (limited to one area of the body) or generalized (occurring all over the body or in several different areas). The medical term for itching is pruritus. Generalized itch, for obvious reasons, is more difficult to treat than localized itch. Itches can also occur with or without skin lesions (for example, bumps or blisters).

Itch can originate in the peripheral nervous system (dermal or neuropathic) or in the central nervous system (neuropathic, neurogenic, or psychogenic). Itch originating in the skin is considered pruritoceptive and can be induced by a variety of stimuli, including mechanical, chemical, thermal, and electrical stimulation. The primary afferent neurons responsible for histamine induced itch are unmyelinated C-fibers. In human C-fiber nociceptors, two major classes exist: mechano-responsive nociceptors and mechano-insensitive nociceptors. Mechano-responsive nociceptors have been shown in studies to respond to mostly pain and mechano-insensitive receptors respond mostly to itch induced by histamine. The feeling of itchiness can be caused by a movement of hair or the release of a chemical (histamine) from cells under the skin. Itchiness is regarded as protective when it helps creatures remove parasites that land on their skin.

Neuropathic itch can originate at any point along the afferent pathway as a result of damage of the nervous system. They could include diseases or disorders in the central nervous system or peripheral nervous system. Examples of neuropathic itch in origin are nostalgia paresthetica, brachioradial pruritus, brain tumors, multiple sclerosis, peripheral neuropathy, and nerve irritation.

Neurogenic itch, which is itch induced centrally but with no neural damage, is often associated with increased accumulation of endogenous opioids and possibly synthetic opioids.

Itch is also associated with some psychiatric disorders such as delusions of parasitosis or related obsessive-compulsive disorders, for example neurotic scratching.

Itching can be caused by many other conditions. For example, xerosis, is the most common cause, frequently seen in winters. It is associated with older age, frequent bathing in hot showers or baths, and high temperature and low humidity environments. Skin conditions (such as psoriasis, eczema, sunburn, athlete's foot, hidradenitis suppurativa and many others) are also other common causes. Most are of an inflammatory nature. Other causes include but are not limited to: insect bites, such as those from mosquitoes, fleas or chiggers; anaphylaxis or allergic reactions, e.g. to contact with specific chemicals, such as urushiol from poison ivy or poison oak; cancers of the blood such as Hodgkin's disease; jaundice where the built up of bilirubin is a skin irritant at high concentrations; polycythemia, which can cause generalized itching due to increased histamine; scabies or infection with lice or worms; liver, kidney, and thyroid illnesses; shaving, which can irritate the skin; diabetes mellitus; dandruff where there is an unusually large amount of epidermal flaking associated with this sensation; iron deficiency such as anemia; parasitic infections such as certain parasites of birds and mammals that are released from infected snails in fresh and saltwater and they cause swimmer's itch, also called cercarial dermatitis; allergy to psychiatric medication; fungal infections, e.g. of the crotch (tinea cruris) commonly known as jock itch, as well as vaginal itching and/or anal itching from sexually transmitted diseases (STDs) or other types of infections; photodermatitis—sunlight reacts with chemicals in the skin, leading to the formation of irritant metabolites, for example, sunburn; directly contact or ingestion of chemical compounds or drugs, e.g. morphine and other opiates; cholestasis related to pregnancy: pruritic urticarial papules and plaques of pregnancy (PUPPP); and gestational pemphigoid. Cholestasis is a condition where bile cannot flow from the liver to the duodenum. Basically, any condition in which the flow of bile from the liver stops or slows. The two basic distinctions are an obstructive type of cholestasis where there is a mechanical blockage in the duct system that can occur from a gallstone or malignancy, and metabolic types of cholestasis which are disturbances in bile formation that can occur because of genetic defects or acquired as a side effect of many medications. Pruritus (itchiness) is the primary symptom of cholestasis. Other symptoms include jaundice, pale stool (from obstructive cholestasis) and dark urine. Some of the causes of cholestasis are cirrhosis, pregnancy, and liver diseases. Pruritus can also occur in pruritus ani, cough, migraine, pain, and pain of apthous ulcers, mastocytosis, and mast cell activation syndrome. Pruritus ani (also known as anusitis), is a Latin term meaning "itchy anus" and is the irritation of the skin at the exit of the rectum, known as the anus, causing the desire to scratch. The intensity of anal itching increases from moisture, pressure, and rubbing caused by clothing and sitting. Causes of itch can also be psychological, that is, due to stress, anxiety, etc., and stress also can aggravate itch from other causes.

Accordingly, itch can be a sensation or symptom associated with a disease or disorder selected from anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with liver, kidney disease, and hyperthyroidism; itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma.

Itching usually prompts scratching, which can sometimes lead to a vicious itch-scratch cycle. Scratching can initially feel so satisfying, but prolonged scratching just leaves one with irritated skin that can still itch and often causes itching itself. Since scratching provides only temporary relief and does not promote healing of the underlying problem, it is best to avoid scratching if at all possible. If scratching breaks open the skin, bacterial infection can set in. And if scratching continues for many months or years, the area that is scratched may develop thickened skin (lichenification) or pigmentation that darkens the area. Obviously, the best way to allow irritated skin to heal is to stop scratching it. However, will power often is not enough since the urge to scratch can be compelling.

In one embodiment, the method described herein is applicable to preventing itch that is a sensation or symptom associated with seasonal conditions such as seborrheic dermatitis, xerosis, anaphylaxis, pruritus ani, cough, migraine, pain, and pain of apthous ulcers, mastocytosis, and mast cell activation syndrome, cholestasis, eczema, and atopic eczematous dermatitis. Subjects that have previous episodes of these conditions but currently the symptoms have disappeared. Such subjects are highly susceptible to itch when these conditions do occur again, For example, xerosis is common among the elderly living in temperate climates mainly during the winter months because of the enclosed indoor heating and low humidity during the winter months. Similarly, eczema, and atopic eczematous dermatitis tend to "flare up" when there is low humidity and/or during the winter months. Other examples of seasonal itch include but are not limited to the itch associated with seasonal allergy (also known as hay fever) during the autumn and spring each year. Dogs and horses are known to suffer from seasonal itch in the fall and the late spring Summer seasonal recurrent dermatitis (SSRD), also known as summer eczema and sweet itch is a skin disease caused by allergic reaction to insect bites. SSRD is considered to be caused by an allergic reaction to the saliva of *Culicoides* flies (also called midges and "no-see-ums"), grass protein, and filariad worm larvae. Sweet itch occurs only in the late spring and summer when insects are present; during the winter months the skin heals and the hair grows back. The therapeutics described herein can be administered during the winter months to the elderly, administered for a subject who has eczema and is temporarily relocating to a dry climate, e.g. vacation, or administered during the seasons when seasonal itch occurs.

Accordingly, in one embodiment, provided herein is a use of an MRG receptor antagonist in the manufacture of medicament for the prevention of itch. In one embodiment, provided herein is a use of an MRGPRX2 receptor antagonist in the manufacture of medicament for the prevention of itch.

In one embodiment, medicament for the prevention of itch can also be used for the treatment of itch. In one embodiment, provided herein is a use of an MRG receptor antagonist in the manufacture of medicament for the treatment of itch. In one embodiment, provided herein is a use of an MRGPRX2 receptor antagonist in the manufacture of medicament for the treatment of itch.

In one embodiment, provided herein is a use of an MRG receptor antagonist in the manufacture of medicament for the prevention and/or treatment of itch, wherein the itch is not a symptom or sensation associated with psoriasis and atopic dermatitis. In one embodiment, provided herein is a use of an MRGPRX2 receptor antagonist in the manufacture of medicament for the prevention and/or treatment of itch, wherein the itch is not a symptom or sensation associated with psoriasis and atopic dermatitis.

In one embodiment, provided herein is a use of an MRG receptor antagonist in the manufacture of medicament for the prevention and/or treatment of itch, wherein the itch is non-histamine mediated. In one embodiment, provided herein is a use of an MRGPRX2 receptor antagonist in the manufacture of medicament for the prevention and/or treatment of itch, wherein the itch is non-histamine mediated.

In one embodiment, provided herein is a use of an MRG receptor antagonist for the prevention and/or treatment of itch. In one embodiment, provided herein is a use of an MRGPRX2 receptor antagonist for the prevention and/or treatment of itch. In one embodiment, the itch is not a symptom or sensation associated with psoriasis and atopic dermatitis. In another embodiment, the itch is non-histamine mediated.

In one embodiment, provided herein is a use of an MRG receptor antagonist for the prevention and/or treatment of itch, wherein the itch is not a symptom or sensation associated with psoriasis and atopic dermatitis. In one embodiment, provided herein is a use of an MRGPRX2 receptor antagonist for the prevention and/or treatment of itch, wherein the itch is not a symptom or sensation associated with psoriasis and atopic dermatitis.

In one embodiment, provided herein is a use of an MRG receptor antagonist for the prevention and/or treatment of itch, wherein the itch is non-histamine mediated. In one embodiment, provided herein is a use of an MRGPRX2 receptor antagonist for the prevention and/or treatment of itch, wherein the itch is non-histamine mediated.

In one embodiment, provided herein is a use of a tri-peptide QWF, (Gln-Trp-Phe) or an analog or a derivative thereof in the manufacture of medicament for the prevention of itch. In one embodiment, medicament for the prevention of itch can also be used for the treatment of itch.

In one embodiment, provided herein is a use of a tri-peptide QWF, (Gln-Trp-Phe) or an analog or a derivative thereof in the manufacture of medicament for the prevention and/or treatment of itch.

In one embodiment, provided herein is a use of [Boc-Gln-D-Trp(Formyl)-Phe benzyl ester] or the tri-peptide QWF [Gln-D-Trp(Formyl)-Phe benzyl ester] or an analog or a derivative thereof in the manufacture of medicament for the prevention and/or treatment of itch.

In one embodiment, provided herein is a use of [Boc-Gln-D-Trp(Formyl)-Phe benzyl ester] or the tri-peptide QWF [Gln-D-Trp(Formyl)-Phe benzyl ester] or an analog or a derivative thereof for the prevention and/or treatment of itch.

In one embodiment, the itch is not a symptom or sensation associated with psoriasis and atopic dermatitis. In another embodiment, the itch is non-histamine mediated.

Accordingly, in one embodiment, provided herein is a use of a tri-peptide QWF, (Gln-Trp-Phe) or an analog or a derivative thereof in the manufacture of medicament for the prevention and/or treatment of itch, wherein the itch is not a symptom or sensation associated with psoriasis and atopic dermatitis.

In one embodiment, provided herein is a use of a tri-peptide QWF, (Gln-Trp-Phe) or an analog or a derivative thereof in the manufacture of medicament for the prevention and/or treatment of itch, wherein the itch is non-histamine mediated.

In one embodiment, provided herein is a use of a tri-peptide QWF, (Gln-Trp-Phe) or an analog or a derivative thereof for the prevention and/or treatment of itch.

In one embodiment, provided herein is a use of a tri-peptide QWF, (Gln-Trp-Phe) or an analog or a derivative thereof for the prevention and/or treatment of itch, wherein the itch is not a symptom or sensation associated with psoriasis and atopic dermatitis.

In one embodiment, provided herein is a use of a tri-peptide QWF, (Gln-Trp-Phe) or an analog or a derivative thereof for the treatment and/or prevention of itch, wherein the itch is non-histamine mediated.

In one embodiment, provided herein is a method of preventing or treating itch in a subject, the method comprising administering a therapeutically effective amount of an MRG receptor antagonist to the subject. In one embodiment, a therapeutically effective amount of a composition comprising an MRG receptor antagonist is administered to the subject.

In one embodiment, provided herein is a method treating a disease or disorder having itch as a symptom or sensation associated with the disease or disorder in a subject, the method comprising administering a therapeutically effective amount of an MRG receptor antagonist to the subject. In one embodiment, a therapeutically effective amount of a composition comprising an MRG receptor antagonist is administered to the subject.

In one embodiment, provided herein is a method of preventing or treating itch or treating a disease or disorder having itch as a symptom or sensation associated with the disease or disorder in a subject, the method comprising administering a therapeutically effective amount of an MRGPRX2 receptor antagonist to the subject. In one embodiment, a therapeutically effective amount of a composition comprising an MRGPRX2 receptor antagonist is administered to the subject.

In one embodiment, provided herein is a method of preventing or treating itch in a subject, the method comprising administering a therapeutically effective amount of an MRGPRX2 receptor antagonist to the subject. In one embodiment, a therapeutically effective amount of a composition comprising an MRGPRX2 receptor antagonist is administered to the subject.

In one embodiment, provided herein is a method of preventing or treating itch in a subject, the method comprising administering a therapeutically effective amount of a tri-peptide QWF, (Gln-Trp-Phe) or an analog or a derivative thereof to the subject. In one embodiment, a therapeutically effective amount of a composition comprising a tri-peptide QWF, (Gln-Trp-Phe) or an analog or a derivative thereof is administered to the subject.

In one embodiment, provided herein is a method of preventing or treating itch in a subject, the method comprising administering a therapeutically effective amount of [Boc-Gln-D-Trp(Formyl)-Phe benzyl ester] or the tri-peptide QWF [Gln-D-Trp(Formyl)-Phe benzyl ester] or an analog or a derivative thereof to the subject. In one embodiment, a therapeutically effective amount of a composition comprising [Boc-Gln-D-Trp(Formyl)-Phe benzyl ester] or the tri-peptide QWF [Gln-D-Trp(Formyl)-Phe benzyl ester] or an analog or a derivative thereof is administered to the subject.

In one embodiment, provided herein is a method of treating a disease or disorder having itch as a symptom or sensation associated with the disease or disorder in a subject, the method comprising administering a therapeutically effective amount of a tri-peptide QWF, (Gln-Trp-Phe) or an analog or a derivative thereof to the subject. In one embodiment, a therapeutically effective amount of a composition comprising a tri-peptide QWF, (Gln-Trp-Phe) or an analog or a derivative thereof is administered to the subject.

In one embodiment, provided herein is a method of treating a disease or disorder having itch as a symptom or sensation associated with the disease or disorder in a subject, the method comprising administering a therapeutically effective amount of [Boc-Gln-D-Trp(Formyl)-Phe benzyl ester] or the tri-peptide QWF [Gln-D-Trp(Formyl)-Phe benzyl ester] or an analog or a derivative thereof to the subject. In one embodiment, a therapeutically effective amount of a composition comprising [Boc-Gln-D-Trp(Formyl)-Phe benzyl ester] or the tri-peptide QWF [Gln-D-Trp(Formyl)-Phe benzyl ester] or an analog or a derivative thereof is administered to the subject.

In one embodiment, provided herein is a method of preventing or treating one or more symptom or sensation arising from an irritation, urticarial (hives), pain, inflammation, asthma, allergy (anaphylaxis), allergic rhinitis, inflammatory bowel disease or irritable bowel disease in a subject, the method comprising administering a therapeutically effective amount of an MRG receptor antagonist to the subject. In one embodiment, a therapeutically effective amount of a composition comprising an MRG receptor antagonist is administered to the subject. In another embodiment, a therapeutically effective amount of a composition comprising an MRGPRX2 receptor antagonist is administered to the subject.

In one embodiment, provided herein is a method of preventing or treating one or more symptom or sensation arising from an irritation, urticarial (hives), pain, inflammation, asthma, allergy (anaphylaxis), allergic rhinitis, inflammatory bowel disease or irritable bowel disease in a subject, the method comprising administering a therapeutically effective amount of a tri-peptide QWF, (Gln-Trp-Phe) or an analog or a derivative thereof is administered to the subject. In one embodiment, a therapeutically effective amount of a composition comprising a tri-peptide QWF, (Gln-Trp-Phe) or an analog or a derivative thereof is administered to the subject.

In one embodiment, provided herein is a method of preventing or treating one or more symptom or sensation arising from an irritation, urticarial (hives), pain, inflammation, asthma, allergy (anaphylaxis), allergic rhinitis, inflammatory bowel disease or irritable bowel disease in a subject, the method comprising administering a therapeutically effective amount of [Boc-Gln-D-Trp(Formyl)-Phe benzyl ester] or the tri-peptide QWF [Gln-D-Trp(Formyl)-Phe benzyl ester] or an analog or a derivative thereof is administered to the subject. In one embodiment, a therapeutically effective amount of a composition comprising [Boc-Gln-D-Trp (Formyl)-Phe benzyl ester] or the tri-peptide QWF [Gln-D-Trp(Formyl)-Phe benzyl ester] or an analog or a derivative thereof is administered to the subject.

In certain embodiments, the present disclosure provides compositions that are useful for treating itch and/or itch-associated conditions in a subject, e.g., a mammal. In one embodiment, the present composition is the tri-peptide QWF. Specifically, the tri-peptide QWF is Boc-Gln-D-Trp (Formyl)-Phe benzyl ester or the tri-peptide QWF is Gln-D-Trp(Formyl)-Phe benzyl ester, or it is any one of the derivatives thereof those compounds, and is sometimes referred to herein in simply as "the tri-peptide QWF" or "QWF". It therefore is to be understood that both the "the tri-peptide QWF" and "QWF" refers to both the Boc-Gin-D-Trp(Formyl)-Phe benzyl ester and Gln-D-Trp(Formyl)-Phe benzyl ester forms of the tri-peptide QWF, and to all of the derivatives of those compounds.

In another embodiment, the present composition is an analog of QWF. One of ordinary skill in the art will recognize that there exists a plurality of QWF analogs, and therefore, based on the findings presented herein, that such plurality of QWF analogs would be useful for treating itch and itch-associated conditions in a mammal.

While not wishing to be bound by theory in any way, in other embodiments, the present composition is any composition that is antagonist of one or both of an MRG receptor and an NK1 receptor. The MRG receptor may be, but is not limited to being, either one or both of the human receptors MRGPRX1 and MRGPRX2, for example.

In certain embodiments, present compositions are useful for treating itch and/or itch-associated conditions in a mammal. The itch-associated condition may be, but is not limited to being, any one or more of anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, scalp itch, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planes, lichen planopilaris, frontal fibrosing alopecia, central centrifugal scarring alopecia, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodermatoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma, for example.

Further, in certain embodiments, the present compositions are useful for treating certain other conditions in a mammal, such as, but not limited to, any one or more of irritation, urticaria, pain, inflammation, asthma, allergy (anaphylaxis), allergic rhinitis, inflammatory bowel disease and irritable bowel disease, for example.

Regardless of their intended therapeutic or contraceptive purpose, the present compositions are effective in all mammals. For example, the present compositions are effective in humans. As another example, the present compositions are effective in canines. As yet another example, the present compositions are effective in all mammals that are typically kept as pets or as livestock, such as, but not limited to, felines, bovines, and equines.

The present disclosure further provides methods of using the compositions described herein to achieve any one or more of the aforementioned intended purposes. In certain method embodiments, one or more of the compositions of the present disclosure are administered topically to a mammal, such as a human or canine, for example. The present compositions therefore may be included in a topical formulation, such as a solution, a suspension, a lotion, a gel, a cream, a foam, a eutectic mixture, an ointment or an emulsion or even a suppository for treating pruritis ani, for example, and the formulation may be topically administered to the mammal, either by the mammal or by another, such as a caretaker or clinician, for example. Further, topical administration of the present compositions optionally may be achieved by using an administration device, such as, but not limited to, a skin patch device, for example.

In other embodiments, the method of the present disclosure includes systemic administration of the present compositions to a mammal. For example, such administration may be, but is not limited to being, oral, parenteral, intratracheal, intrathecal, intracranial, intrarectal, intranasal, intravenous, intramuscular, intraperitoneal, intracerebrospinal, subcutaneous, intra-epidermal, intra-arterial or intrasynovial administration.

In certain embodiments, the present compositions are administered to a mammal in conjunction with one or more agents. For example, these agents may be, but are not limited to being, any one or more of a mast cell stabilizer, a TRP channel inhibitor or activator, e.g., menthol which activates TRPM8 an inhibitor of a nerve growth factor receptor, e.g., TrkA or an inhibitor of a cytokine, e.g., thymic stromal lymphopoietin or interleukin-4 or its receptor or interleukin-31 or its receptor or a calcinuerin inhibitor or a corticosteroid.

In one embodiment, provided herein is a composition or formulation comprising an MRG receptor antagonist and/or tri-peptide QWF, (Gln-Trp-Phe) or an analog or a derivative thereof for use in the prevention and/or treatment of itch or for use in treating a disease or disorder having itch as a symptom or sensation associated with the disease or disorder in a subject, or of preventing or treating one or more symptom or sensation arising from an irritation, urticarial (hives), pain, inflammation, asthma, allergy, allergic rhinitis, inflammatory bowel disease or irritable bowel disease in a subject.

In some embodiments, the described composition or formulation further comprises a pharmaceutically acceptable carrier.

In one embodiment, provided herein is a pharmaceutical composition or pharmaceutical formulation comprising an MRG receptor antagonist and/or tri-peptide QWF, (Gln-Trp-Phe) or an analog or a derivative thereof, and a pharmaceutically acceptable carrier. In some embodiments, the described pharmaceutical composition or formulation further comprises at least one addition agent having anti-itch properties. For example, a PAR2 or PAR4 antagonist, or a cysteine protease inhibitor such as a cathepsin (see known cysteine protease inhibitors shown in Table 2). In one embodiment, provided herein is a pharmaceutical composition or pharmaceutical formulation comprising an MRG receptor antagonist and/or tri-peptide QWF, (Gln-Trp-Phe) or an analog or a derivative thereof, an addition agent having anti-itch properties, and a pharmaceutically acceptable carrier. In other embodiments, the compositions or formulations described herein comprise a MRGPRX2 receptor antagonist. That is, an antagonist that is specific to the MRGPRX2 receptor and have minimal effect on other MRG receptors. In other embodiments, the compositions or formulations described herein comprise a MRGPRX2 receptor antagonist that is an inhibitory antibody against MRGPRX2 and/or an RNAi molecule that inhibits the expression of MRGPRX2 in vivo.

Recognition that itch is of major medical significance is driving research into the basic mechanisms that underlie this sensory phenomenon. Progress is being made on identification of periphery and central mediators, receptors and channels that contribute to itch.

Substance P (SP) has long been established as an inflammatory neuropeptide and potent endogenous pruritogen in mice (1) and humans (2). It belongs to a family of structurally related peptides known as tachykinins that are derived from alternative processing of the Tac genes (3). Tachykinins are expressed throughout the nervous and immune systems and regulate a diverse range of physiologic processes. Tachykinins have been considered to interact with three neurokinin receptors, termed NK1, NK2 and NK3, encoded by three Tacr genes (4). SP has the highest affinity for NK1 and several antagonists of this receptor have been developed to inhibit nociceptive and pro-inflammatory properties of SP that are presumably mediated via NK1. NK1 antagonists are strikingly effective in animal models of several diseases, including migraine and asthma, but they are surprisingly ineffective in the clinic, in these conditions and their effectiveness for treating itch is not clear (5, 6). It is possible that SP interacts with a receptor other than NK1 to mediate nociceptive effects (7). SP can interact with Mrgprs, described below, but such interactions have not been investigated with respect to function, including sensory processing, until now.

A family of GPCRs now known as Mas-related G-protein coupled receptors (Mrgprs) was identified in 2001 (8). Mrgprs were found to be identical to a group of orphan receptors known as sensory neuron-specific G-protein coupled receptors on human and rat small sensory neurons implicated in nociception (9). The concept of Mrgprs serving as innate sensors in general and as sensors for pruritogens specifically is supported by the following lines of evidence. Mrgprs first appear in tetrapods (10), animals endowed with the capacity to remove exogenous agents by scratching while navigating on land. Mrgprs demonstrate high constitutive activity and respond to several ligands, many of which are pruritogens, (10-13) i.e., compounds or agents that directly or indirectly elicit the itch sensation. The tissue distribution of Mrgprs is limited primarily to where sensors are needed—sensory nerves and mast cells (10, 11, 14, 15).

The inventors have discovered that SP might provoke itch via activation of Mrgprs. The inventors also found that an existing NK1 antagonist might have the added property of serving as an antagonist to Mrgprs, the NK1 antagonist being SP. The inventors tested with in vitro and in vivo studies and a targeted compound screen. The inventors found that SP provokes itch in NK1 knockout mice, diminishing the role, at least of peripheral NK1, in itch. In contrast, SP did not provoke itch in Mrgpr cluster knockout mice, which we link to the absence of MrgprA1 which we find to be activated specifically by SP. The screen identifies QWF, a known tripeptide NK1 antagonist, as the first antagonist of human MRGPRX2, the mouse orthologue MrgprB2 and the mouse homologue MrgprA1. The inventors also find that L733060, an NK1 antagonist used to excellent effect in mouse studies of inflammation, and aprepitant, a structurally similar molecule used in the clinic, are also antagonists of mouse MrgprB2, although not human MRGPRX2. The limited effectiveness of aprepitant in itch and inflammation in humans may reflect lack of activity on human MRGPRX2. The inventors show that QWF not only inhibits SP-induced itch in mice but also inhibits degranulation of human mast cells induced by drugs associated with IgE-independent pseudo-allergic drug reactions. In other word, QWF blocked mast cell degranulation, QWF blocked in vitro activation of Mrgprs and in vivo scratching induced by pruritogens. Accordingly, it is possible that antagonists of human MRGPRX2 may be of benefit in the treatment of itch, inflammation and drug reactions.

In some embodiments, the described composition or formulation is useful in the prevention of mast cell degranulation, or the activation of Mrgprs (i.e. signal transduction via the Mrgprs, as analysed by $Ca^{2+}$ fluxes in vivo) or the scratching induced by pruritogens.

In one embodiment of any uses or methods described, the itch is not a symptom or sensation associated with psoriasis and atopic dermatitis. In another embodiment of any uses or methods described, the itch is non-histamine mediated.

In one embodiment of any uses or methods described, the MRG receptor is a human MRG receptor. In another embodiment of any uses or methods described, the MRG receptor is mouse or rat MRG receptor.

In one embodiment of any uses or methods described, the MRG receptor is MRGPRX1. That is, the antagonist affects specifically the MRGPRX1 receptor.

In another embodiment of any uses or methods described, the MRG receptor is not MRGPRX1. That is, the antagonist does not affect specifically the MRGPRX1 receptor.

In another embodiment of any uses or methods described, the MRG receptor is MRGPRX2. That is, the antagonist affects specifically the MRGPRX2 receptor.

In one embodiment of any uses or methods described, the MRG receptor antagonist also antagonizes an NK1 receptor. That is, the antagonist affects both the MRGPRX1 receptor and the NK1 receptor.

In one embodiment of any uses or methods described, the MRG receptor antagonist does not antagonizes an NK1 receptor.

In one embodiment of any uses or methods described, the MRG receptor antagonist is a tri-peptide QWF, (Gln-Trp-Phe) or an analog or a derivative thereof.

In one embodiment of any uses or methods described, the MRG receptor antagonist is an antibody against a MRG receptor, wherein the antibody antagonizes or inhibits or reduces or decreases the naturally occurring signaling from the MRG receptor in the presence of Substance P, meaning the antibody against a MRG receptor is an inhibitory antibody. In some embodiments, the antibody is a monoclonal antibody—the monoclonal antibody is a human monoclonal antibody, a mouse monoclonal antibody, or a humanized mouse monoclonal antibody; a single chain antibody; a single chain Fv (scFv) fragment; a Fab fragment; a humanized antibody; a chimeric antibody; chimeric antigen receptor (CAR); or an antibody is produced by a hybridoma cell line.

In one embodiment of any uses or methods described, the MRG receptor antagonist is an siRNA or an shRNA or RNAi or siRNA/shRNA/RNAi lentivirus or an RNA interference agent that inhibits expression of the receptor in the cell.

In one embodiment of any uses or methods described, the inhibitory antibody reduces signaling elicited by Substance P by at least 10% compared to a control reference in the absence of the inhibitory antibody, or the RNA interference agent reduces expression by at least 10% compared to a control reference of in the absence of the RNA interference agent.

In other embodiments of any uses or methods described, the inhibitory antibody reduces signaling elicited by Substance P by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 99%, and by at least 100% compared to a control reference in the absence of the inhibitory antibody.

In other embodiments of any uses or methods described, the RNA interference agent reduces expression by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 99%, and by at least 100% compared to a control reference in the absence of the RNA interference agent.

In one embodiment of any uses or methods described, the tri-peptide QWF is [Boc-Gln-D-Trp(Formyl)-Phe benzyl ester] or the tri-peptide QWF [Gln-D-Trp(Formyl)-Phe benzyl ester] or an analog or a derivative thereof.

The tri-peptide, QWF, an analog and a derivative thereof are known peptide compounds that can antagonize or inhibits the activity of Substance P in activating the neurokinin 1 receptor. Substance P (SP) is an undecapeptide (a peptide composed of a chain of 11 amino acid residues) member of the tachykinin neuropeptide family. It is a neuropeptide, acting as a neurotransmitter and as a neuromodulator. Substance P is released from the terminals of specific sensory nerves. It is found in the brain and spinal cord and is associated with inflammatory processes and pain. The endogenous receptor for substance P is neurokinin 1 receptor (NK1-receptor, NK1R). Analog and a derivative of QWF are described in the U.S. Pat. No. 5,164,372, and this publication is hereby incorporated by reference in its entirety.

In one embodiment of any uses or methods described, the itch is a symptom or sensation associated with a disease or disorder selected from anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen planopilaris, frontal fibrosing alopecia, central centrifugal scarring alopecia, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma.

In another embodiment, the uses and methods described herein are also applicable to itch with no known etiology.

In one embodiment of any uses or methods described, the itch is a non-histamine mediated itch. As used herein, a "non-histamine mediated itch" refers to an itch sensation that is not alleviated by antihistamines and is not elicited via histaminergic pathway.

In one embodiment of any methods described, the subject is any mammal that expresses a MRG receptor and/or an NK1 receptor. For example, a human, a dog, a cat, pig, goat, a canine, and a horse, etc.

In one embodiment of any methods described, the method further comprising administering an additional agent to the subject in combination with the MRG receptor antagonist.

In one embodiment of any uses or methods described, the additional agent is selected from the group consisting of a mast cell stabilizer, a TRP channel inhibitor or activator, an inhibitor of a nerve growth factor receptor, e.g., TrkA or an inhibitor of a cytokine, e.g., thymic stromal lymphopoietin or interleukin-4 or its receptor or interleukin-31 or its receptor or a calcinuerin inhibitor or a corticosteroid.

In one embodiment of any uses or methods described, the additional agent has anti-itch properties.

In one embodiment of any uses or methods described, the MRG receptor antagonist or tri-peptide QWF, (Gln-Trp-Phe) or an analog or a derivative thereof can be administered in conjunction with other medicaments associated with the respective medical condition. Examples include menthol and phenol, calamine, topical antihistamines, local anesthetics, capsaicin, strontium nitrate, H1-receptor antagonists, H2-receptor antagonists, H4-receptor antagonists, doxepin, ondansetron, paroxetine, and mirtazapine. Other medicaments include but are not limited to, for dry skin: emollient cream; for cholestasis: colestyramine, rifampicin, opioid antagonists, androgens; for uremia: dialysis, UVB phototherapy and for paraneoplasia: paroxetine.

In one embodiment of any uses or methods described, the additional agent having anti-itch properties is a cysteine protease inhibitor. Examples of known cysteine protease inhibitors are shown in Table 2 and are incorporate herein by reference in its entirety.

In one embodiment of any uses or methods described, the cysteine protease used in the methods of preventing and/or treating itch is a cathepsin.

In one embodiment of any uses or methods described, the cathepsin is selection from the group consisting of cathepsin B, C, F, J, K, H, L, P, Q, S, W, X, V, and Z.

Cathepsins belong to the papain superfamily of cysteine proteases. These proteases function in the normal physiological as well as pathological degradation of connective tissue. Cathepsins play a major role in intracellular protein degradation, turnover and remodeling. To date, a number of cathepsin have been identified and sequenced from a number of sources. These cathepsins are naturally found in a wide variety of tissues (see review by Barrett and Kirschke, Methods Enzymol. 1981, 80 Pt C:535-61). For example, cathepsin B, F, H, L, K, S, W, and Z have been cloned. Cathepsin K (which is also known by the abbreviation cat K) is also known as cathepsin O and cathepsin O2. See U.S. Pat. No. 5,861,298, which is hereby incorporated by reference in its entirety. Cathepsin L is implicated in normal lysosomal proteolysis as well as several disease states, including, but not limited to, metastasis of melanomas. Cathepsin K is synthesized as a 37 kDa pre-pro enzyme, which is localized to the lysosomal compartment and where it is presumably autoactivated to the mature 27 kDa enzyme at low pH. See McQueney, M. S. et al., 1997, J. Biol. Chem. 272:13955-13960; Littlewood-Evans, A. et al., 1997, Bone 20:81-86, which are hereby incorporated by reference in their entirety.

There are fifteen human cathepsins, including eleven cysteine, two aspartic and two serine proteases. Cathepsins were traditionally considered lysosomal proteases. It is now recognized that the broad expression and range of pH dependence of some cathepsins reveal that they have many functional roles including tissue remodeling, metastasis and inflammation. Examples of cysteine cathepsin activities include cleavage of collagen by cathepsin L to generate endostatin, an endogenous inhibitor of angiogenesis, and cleavage of the invariant chain in antigen presenting cells by cathepsin S as part of the inflammatory cascade.

In one embodiment of any uses or methods described, the cathepsin inhibitor is selected from the group consisting of stefin A, stefin B, cystatin C, human testican-1, naphthalene endoperoxide (effective against Cathepsin B, L, S), CA-074 (specific for cathepsin B), odanacatib (formerly MK-0822) (specific for cathepsin K), CLIK-148 and CLIK-195 (specific for cathepsin L), CLIK-60 (specific for cathepsin S), fluoromethyl ketone, heterocyclic oxygen-containing peptidomimetics, vinyl sulfones, pyridoxal phosphate, high potent pyrazole-based compounds such as 1-[3-[4-(6-Chloro-2,3-dihydro-3-methyl-2-oxo-1H-benzimidazol-1-yl)-1-piperidinyl]propyl]-4,5,6,7-tetrahydro-5-(methylsulfonyl)-3-[4-(trifluoromethyl)phenyl]-1H-pyrazolo[4,3-c]pyridine (aka JNJ 10329670), RWJ-445380, and compounds 1-41 of Johnson & John Pharmaceutical as described by Wei, J. et. al. (Bioorganic & Medicinal Chemistry Letters, 2007, 17:5525-5528) and in R. L. Thurmond, et al. J. Pharmaco. Exp. Therapeutics, 2004, 268-276; Compounds I, II, and III, from Boehringer Ingelheim Pharmaceuticals (Desai, S. N. et. al., Eur. J. Pharmacol. 538: 168-174); leupeptin, and chloroquine. These references are hereby incorporated by reference in their entirety.

In another embodiment of any uses or methods described, the cathepsin inhibitor is selected from those described in the U.S. Pat. Nos. 5,374,623; 5,317,086; 5,776,718; 5,998, 470; 6,004,933; 6,048,861; 6,057,362; 6,232,342; 6,284, 777; 6,353,017; 6,369,077; 6,331,1542; 6,420,364; 6,455, 502; 6,476,026; 6,462,076; 6,492,362; 6,506,733; 6,566, 373; 6,576,630; 6583137; 6,583,155; 6,635,621; 6,835,727; 6,876,706; 6,953,793; 6,936,606; 7,279,478; 7,312,211; U.S. Pat. Applications 2003/0069240 and 2007/0117785; and the PCT application WO/2005/066159, and these are hereby incorporated by reference in their entirety.

In one embodiment of any uses or methods described, the cysteine protease inhibitor is a non-specific inhibitor. For example, E-64 (trans-epoxysuccinyl-L-leucylamide-(4-guanidino) butane).

In one embodiment of any uses or methods described, the cathepsin inhibitor is a specific inhibitor, for example, specific inhibitors for cathepsin K, S, or L. Selective peptide based inhibitors of cathepsin K have been developed See Bromme, D., et al., 1996, Biochem. J. 315:85-89; Thompson, S. K., et al., 1997, Proc. Natl. Acad. Sci. USA. 94:14249-14254, which are hereby incorporated by reference in their entirety. The crystal structure of cathepsin K has been resolved. See McGrath, M. E., et al., 1997, Nat. Struct. Biol. 4:105-109; Zhao, B., et al., 1997, Nat. Struct. Biol. 4: 109-11, which are hereby incorporated by reference in their entirety. Using the crystal structures and aided by computer modeling programs, synthetic organic compounds that mimic the substrate-binding site of cathepsin K can be designed. Such software for computer assisted molecular (Drug) design can be found at the World Wide Web "period"netsci "period" org/Resources/Software/Modeling/CADD/, e.g. MOLSCAT, Chem3D, and ADAPT. Examples of specific cathepsin inhibitors include naphthalene endoperoxide-singlet oxygen. Singlet oxygen is a causal factor in light-induced skin photoaging and the cytotoxic process of tumor cells in photodynamic chemotherapy. Naphthalene endoperoxide is specific for cathepsins B, L, and S.

In one embodiment of any uses or methods described, the MRG receptor antagonist or tripeptide QWF, analogs or derivatives thereof described herein is administered in conjunction with 3-substituted-2-(diphenylmethyl)-1-azabicyclo[2.2.2]octane. The compound 3-substituted-2-(diphenylmethyl)-1-azabicyclo[2.2.2]octane is described in US Patent Application No: 2014/0303231, and this publication is hereby incorporated by reference in its entirety.

In one embodiment of any compositions or formulations described, the MRG receptor antagonist or tripeptide QWF, analogs or derivatives thereof described herein is administered in conjunction with 3-substituted-2-(diphenylmethyl)-1-azabicyclo[2.2.2]octane.

In one embodiment of any uses or methods described, the MRG receptor antagonist or tripeptide QWF, analogs or derivatives thereof described herein is administered in conjunction with a PAR2 antagonist, for example, the synthetic peptide FSLLRY-NH2 (SEQ. ID. No. 1), the small molecule ENMD-1068: N(1)-3-methylbutyryl-N(4)-6-aminohexanoyl-piperazine, PAR2 monoclonal antibody, SAM-11 and P2pal-21 (Covic, J., et. al., 2002, PNAS, 99:643-648).

In another embodiment of any uses or methods described, the MRG receptor antagonist or tripeptide QWF, analogs or derivatives thereof described herein is administered in conjunction with a PAR 4 antagonist, for example, tcY-NH(2); pepducin P4 pal-10; pepducin P4 pal-15; Tc-APGKF-NH(2) (SEQ. ID. No. 2); polyclonal anti-PAR4 antibody; monoclonal anti-PAR4 antibody, YD-3; Statins: atorvastatin, pravastatin, fluvastatin, cerivastatin, lovastatin, simvastatin, rosuvastatin, pitavastatin, and metabolite thereof; and ethanol. Method of treating itch with a PAR 4 antagonist is described in U.S. Pat. Publication No.: US2008/0213252 and this is hereby incorporated by reference by its entirety.

In another embodiment, the method described herein is used in conjunction with other known anti-itch therapies such as menthol and phenol, calamine, topical antihistamines, local anesthetics, capsaicin, strontium nitrate, H1-receptor antagonists, H2-receptor antagonists, doxepin, ondansetron, paroxetine, mirtazapine, opioid antagonists. For example, for dry skin itch: emollient cream; for cholestasis-related itch: colestyramine, rifampicin, opioid antagonists, and androgens, for uremia-related itch: dialysis, UVB phototherapy; and for paraneoplasia-related itrch: paroxetin.

In another embodiment, the method described herein can be used in conjunction with therapies for anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma.

In one embodiment of any uses or methods described, the MRG receptor antagonist is administered topically to the subject.

In one embodiment of any uses or methods described, the MRG receptor antagonist is contained in a topical formulation and the topical formulation is selected from the group consisting of a solution, a suspension, a lotion, a gel, a cream, a foam, a eutectic mixture, an ointment and an emulsion.

In one embodiment of any uses or methods described, the formulation is associated with a skin patch device.

In one embodiment of any uses or methods described, the MRG receptor antagonist is administered systemically to the subject.

In one embodiment of any uses or methods described, the administration is selected from the group consisting of oral, parenteral, introatracheal, intrathecal, intracranial, intrarectal, intranasal, intravenous, intramuscular, intraperitoneal, intracerebrospinal, subcutaneous, intra-epidermal, intra-arterial and intrasynovial administration.

The compositions or formulations useful in the disclosed purposes include solutions, suspensions, lotions, gels, creams, ointments, emulsions, skin patches, etc. All of these dosage forms, along with methods for their preparation, are well known in the pharmaceutical and cosmetic art. Harry's Cosmeticology (Chemical Publishing, 7th ed. 1982); Remington's Pharmaceutical Sciences (Mack Publishing Co., 18th ed. 1990). Typically, such topical formulations contain the active ingredient in a concentration range of 0.001 to 10 mg/ml, in admixture with suitable vehicles. Other desirable ingredients for use in such anti-pruritic preparations include preservatives, co-solvents, viscosity building agents, carriers, etc. Solvents includes such as propylene glycol, polyethylene glycol 300, polyethylene glycol 400 or polyethylene glycol 1540 alone or in combination with 1,2,6-hexanetriol, propylene carbonate or other such solvents. The carrier itself or a component dissolved in the carrier may have palliative or therapeutic properties of its own, including moisturizing, cleansing, or anti-inflammatory/anti-itching properties. The cysteine protease inhibitors of the method described herein can be combined with a therapeutically effective amount of anti-inflammatories such as corticosteroids, fungicides, antibiotics, moisturizers or anti-itching compounds; and MRG receptor antagonists.

Penetration enhancers may, for example, be surface active agents; certain organic solvents, such as di-methylsulfoxide and other sulfoxides, dimethyl-acetamide and pyrrolidone; certain amides of heterocyclic amines, glycols (e.g. propylene glycol); propylene carbonate; oleic acid; alkyl amines and derivatives; various cationic, anionic, nonionic, and amphoteric surface active agents; and the like.

Topical administration of a pharmacologically effective amount may utilize transdermal delivery systems well known in the art such as those described in U.S. Pat. No. 4,627,429, D296,006, 4,921,475, 5,591,767, 5,681,580, 6,009,346, 6,190,315, 7,066,884 for passive, automated, iontophoretic, and sonophoretic transdermal delivery. These patents are hereby incorporated by reference in their entirety.

In addition to topical therapy, the MRG receptor antagonist or tripeptide QWF, analogs or derivatives thereof described herein can also be administered systemically in a pharmaceutical formulation. Systemic routes include but are limited to oral, parenteral, nasal inhalation (aerosol nebulizer), intratracheal, intrathecal, intracranial, and intrarectal. The pharmaceutical formulation is preferably a sterile saline or lactated Ringer's solution. For therapeutic applications, the preparations described herein are administered to a mammal, preferably a human, in a pharmaceutically acceptable dosage form, including those that may be administered to a human intervenously as a bolus or by continuous infusion over a period of time, by intramuscular, intraperitoneal, intracerebrospinal, subcutaneous, intra-arterial, intrasynovial, intrathecal, oral, topical, or inhalation routes. For these uses, additional conventional pharmaceutical preparations such as tablets, granules, powders, capsules, and sprays may be preferentially required. In such formulations further conventional additives such as binding-agents, wetting agents, propellants, lubricants, and stabilizers may also be required.

The compositions can be formulated as a sustained release composition. For example, sustained-release pharmaceutical compositions include, but are not limited to, sustained-release matrices such as biodegradable matrices or semi-permeable polymer matrices in the form of shaped articles, e.g., films, or mirocapsules that comprise cysteine protease inhibitors described herein.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of polylactide, polyglycolide, or polylactide co-glycolide (co-polymers of lactic acid and glycolic acid).

Sustained-release matrices include polylactides (U.S. Pat. No. 3,773,919; EP 58,481), copolymers of L-glutamic acid and gamma-ethyl-L-glutamate (U. Sidman et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(-)-3-hydroxybutyric acid (EP 133,988). Sustained-release compositions also include liposomally entrapped cathepsin inhibitors. Such liposomes can be prepared by methods known well known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979). Other known methods are described in DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324, all of which are hereby incorporated by reference in its entirety. Ordinarily, the liposomes are of the small (about 200-800 Angstroms) unilamellar type in which the lipid content is greater than about 30 mol. percent cholesterol, the selected proportion being adjusted for the optimal therapy. Other biodegradable polymers and their use are described, for example, in detail in Brem et al. (1991, J. Neurosurg. 74:441-446).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474; 4,925,673 and 3,625,214, and Jein, TIPS 19:155-157 (1998), the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations comprising cysteine protease inhibitors are administered via catheter directly to the inside of blood vessels. The administration can occur, for example, through holes in the catheter. In those embodiments wherein the active compounds have a relatively long half-life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

In one embodiment, osmotic minipumps are used to provide controlled sustained delivery of pharmaceutical compositions comprising MRG receptor antagonist or tripeptide QWF, analogs or derivatives thereof described herein, through cannulae to the site of interest, e.g. directly into a tissue at the site of metastatic growth or into the vascular supply of a tumor. The pump can be surgically implanted, for example continuous administration of endostatin, an anti-angiogenesis agent, by intraperitoneally implanted osmotic pump is described in Cancer Res. 2001 Oct. 15; 61(20):7669-74. Therapuetic amounts of a cysteine protease inhibitor can also be continually administered by an external pump attached to an intravenous needle.

For enteral administration, a composition comprising MRG receptor antagonist or tripeptide QWF, analogs or derivatives thereof described herein can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature. The enteral composition can be formulated for timed, sustained release such as in beads with multi layers providing a lag time before drug release.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethyl-ammonio-1-propanesulfonate), Big-CHAPS (N, N-bis 3-D-gluconamidopropyl)-cholamide), chlorobutanol, octoxynol-9, benzyl alcohol, phenols, cresols, and alkyl alcohols. An especially preferred oral absorption enhancer for the present disclosure is sodium lauryl sulfate.

Formulations for rectal administration may be presented as a suppository with a conventional carrier, e.g., cocoa butter or Witepsol S55 (trademark of Dynamite Nobel Chemical, Germany), for a suppository base.

When the MRG receptor antagonist or the tripeptide QWF forms the basic group of the anti-itch formulation or composition, pharmaceutically acceptable salts can be used. Such salts encompassed within the term "pharmaceutically acceptable salts" refer to non-toxic salts which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucaamine ammonium salt, oleate, oxalate, pamoate (embonate), palmitate, pantothenate, phosphate/diphosphate, polygalacturonate, salicylate, stearate, sulfate, subacetate, suceinate, tannate, tartrate, teoclate, tosylate, triethiodide and valerate. Furthermore, where the compounds of the disclosure carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

In one embodiment, MRG receptor antagonist or the tripeptide QWF described herein includes within its scope prodrugs of the MRG receptor antagonist or the tripeptide QWF. In general, such prodrugs will be functional derivatives of the MRG receptor antagonist or the tripeptide QWF which are readily convertible in vivo into the active MRG receptor antagonist or the tripeptide QWF. Thus, in the methods of treatment of the present disclosure, the term "administering" shall encompass the treatment of the various conditions described with the MRG receptor antagonist or the tripeptide QWF specifically disclosed or with a MRG receptor antagonist or the tripeptide QWF which may not be specifically disclosed, but which converts to an active MRG receptor antagonist or the tripeptide QWF in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of MRG receptor antagonist or the tripeptide QWF into the biological milieu.

Pharmaceutically acceptable carriers that are inherently nontoxic and nontherapeutic are preferred. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of compositions include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. No. 3,773,919; EP 58,481A; U.S. Pat. No. 3,887,699; EP 158,277A; Canadian Patent No. 1176565; U. Sidman et al., Biopolymers 22:547 (1983) and R. Langer et al., Chem. Tech. 12:98 (1982), all of which are hereby incorporated by reference in its entirety. The cysteine protease inhibitors will usually be formulated in such vehicles at a concentration of about 0.1 mg/ml to 1000 mg/ml.

In one embodiment, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the pharmaceutical formulation to be used for therapeutic administration must be sterile. Sterility is readily accomplished by filtration through sterile filtration membranes (e.g., 0.2 micron membranes). The MRG receptor antagonist, or the MRGPRX2 receptor antagonist, or the tripeptide QWF can be stored in lyophilized form or as an aqueous solution if it is highly stable to thermal and oxidative denaturation. The pH of the cysteine protease inhibitor preparations typically can be about from 6 to 8.

The precise dosage of a selected MRG receptor antagonist or tripeptide QWF, analogs or derivatives thereof will vary with the route of administration, the dosage form, the dosing schedule, the oral potency of the selected MRG receptor antagonist or the tripeptide QWF chosen, its physicochemical characteristics, the age, size, sex and condition of the mammal or human, the nature, severity, and the location of the itch sensations and underlying disorder if any, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. The selection of proper dosage is well within the skill of an ordinary skilled physician. For example, topical formulations are usually administered up to four-times a day; an effective oral dose of a MRG receptor antagonist or the tripeptide QWF is typically from about 1.5 to about 6000 µg/kg body weight and preferably about 10 to about 2000 µg/kg of body weight.

The disclosure can be defined by any of the following numbered paragraphs:

[1] Use of an MRG receptor antagonist in the manufacture of medicament for the prevention of itch.

[2] Use of an MRG receptor antagonist in the manufacture of medicament for the treatment of itch, wherein the itch is not a symptom or sensation associated with psoriasis and atopic dermatitis.

[3] Use of an MRG receptor antagonist in the manufacture of medicament for the treatment of itch, wherein the itch is non-histamine mediated.

[4] Use of an MRG receptor antagonist for the prevention of itch.

[5] Use of an MRG receptor antagonist for the treatment of itch, wherein the itch is not a symptom or sensation associated with psoriasis and atopic dermatitis.

[6] Use of an MRG receptor antagonist for the treatment or prevention of itch, wherein the itch is non-histamine mediated.
[7] The use of any one of paragraphs 1-6, wherein the MRG receptor antagonist also antagonizes an NK1 receptor.
[8] The use of any one of paragraphs 1-7, wherein the MRG receptor antagonist antagonizes a MRGPRX1 receptor.
[9] The use of any one of paragraphs 1-7, wherein the MRG receptor antagonist does not antagonizes a MRGPRX1 receptor.
[10] The use of any one of paragraphs 1-9, wherein the MRG receptor antagonist antagonizes a MRGPRX2 receptor.
[11] The use of any one of paragraphs 1-10, wherein the MRG receptor antagonist is a tri-peptide QWF, (Gln-Trp-Phe) or an analog or a derivative thereof.
[12] The use of paragraph 11, wherein the tri-peptide QWF is [Boc-Gln-D-Trp(Formyl)-Phe benzyl ester] or the tri-peptide QWF [Gln-D-Trp(Formyl)-Phe benzyl ester] or an analog or a derivative thereof.
[13] The use of any one of paragraphs 1-12, wherein the itch is a symptom or sensation associated with a disease or disorder selected from anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen planopilaris, frontal fibrosing alopecia, central centrifugal scarring alopecia, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma.
[14] Use of a tri-peptide QWF, (Gln-Trp-Phe) or an analog or a derivative thereof in the manufacture of medicament for the prevention of itch.
[15] Use of a tri-peptide QWF, (Gln-Trp-Phe) or an analog or a derivative thereof in the manufacture of medicament for the treatment of itch, wherein the itch is not a symptom or sensation associated with psoriasis and atopic dermatitis.
[16] Use of a tri-peptide QWF, (Gln-Trp-Phe) or an analog or a derivative thereof in the manufacture of medicament for the treatment of itch, wherein the itch is non-histamine mediated.
[17] Use of a tri-peptide QWF, (Gln-Trp-Phe) or an analog or a derivative thereof for the prevention of itch.
[18] Use of a tri-peptide QWF, (Gln-Trp-Phe) or an analog or a derivative thereof for the treatment of itch, wherein the itch is not a symptom or sensation associated with psoriasis and atopic dermatitis.
[19] Use of a tri-peptide QWF, (Gln-Trp-Phe) or an analog or a derivative thereof for the treatment or prevention of itch, wherein the itch is non-histamine mediated.
[20] The use of any one of paragraphs 14-19, wherein the tri-peptide QWF is [Boc-Gln-D-Trp(Formyl)-Phe benzyl ester] or the tri-peptide QWF [Gln-D-Trp(Formyl)-Phe benzyl ester] or an analog or a derivative thereof
[21] The use of any one of paragraphs 14-20, wherein the tri-peptide QWF antagonizes an NK1 receptor.
[22] The use of any one of paragraphs 14-21, wherein the tri-peptide QWF antagonizes a MRGPRX1 receptor.
[23] The use of any one of paragraphs 14-21, wherein the tri-peptide QWF does not antagonizes a MRGPRX1 receptor.
[24] The use of any one of paragraphs 14-23, wherein the tri-peptide QWF antagonizes a MRGPRX2 receptor.
[25] The use of any one of paragraphs 14-24, wherein the itch is a symptom or sensation associated with a disease or disorder selected from anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen planopilaris, frontal fibrosing alopecia, central centrifugal scarring alopecia, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma.
[26] A method of preventing or treating itch or treating a disease or disorder having itch as a symptom or sensation associated with a disease or disorder in a subject, the method comprising administering a therapeutically effective amount of an MRG receptor antagonist to the subject.
[27] The method of paragraph 26, whereby the itch sensation is reduced.
[28] The method of paragraph 26 or 27, wherein the MRG receptor antagonist also antagonizes an NK1 receptor.
[29] The method of any one of paragraphs 26-28, wherein the MRG receptor antagonist is a tri-peptide QWF (Gln-Trp-Phe) or an analog or a derivative thereof.
[30] The method of paragraph 29 wherein the tri-peptide QWF is [Boc-Gln-D-Trp(Formyl)-Phe benzyl ester] or the tri-peptide QWF [Gln-D-Trp(Formyl)-Phe benzyl ester] or an analog or a derivative thereof.
[31] The method of method of any one of paragraphs 26-30, wherein the MRG receptor is MRGPRX1.
[32] The method of method of any one of paragraphs 26-30, wherein the MRG receptor is not MRGPRX1.
[33] The method of method of any one of paragraphs 26-30, wherein the MRG receptor is MRGPRX2.

[34] The method of method of any one of paragraphs 26-33, wherein the disease or disorder is selected from the group consisting of anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, scalp itch, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen plans, lichen planopilaris, frontal fibrosing alopecia, central centrifugal scarring alopecia, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodermatoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma.

[35] The method of method of any one of paragraphs 26-35, wherein the MRG receptor antagonist is administered topically to the subject.

[36] The method of method of any one of paragraphs 26-35, wherein the MRG receptor antagonist is contained in a topical formulation and the topical formulation is selected from the group consisting of a solution, a suspension, a lotion, a gel, a cream, a foam, a eutectic mixture, an ointment and an emulsion.

[37] The method of paragraph 36, wherein the formulation is associated with a skin patch device.

[38] The method of method of any one of paragraphs 26-35, wherein the MRG receptor antagonist is administered systemically to the subject.

[39] The method of paragraph 38, wherein the administration is selected from the group consisting of oral, parenteral, introatracheal, intrathecal, intracranial, intrarectal, intranasal, intravenous, intramuscular, intraperitoneal, intracerebrospinal, subcutaneous, intraepidermal, intra-arterial and intrasynovial administration.

[40] The method of method of any one of paragraphs 26-39, the method further comprising administering an additional agent to the subject in combination with the MRG receptor antagonist.

[41] The method of paragraph 40, wherein the additional agent is selected from the group consisting of a mast cell stabilizer, a TRP channel inhibitor or activator, an inhibitor of a nerve growth factor receptor, e.g., TrkA or an inhibitor of a cytokine, e.g., thymic stromal lymphopoietin or interleukin-4 or its receptor or interleukin-31 or its receptor or a calcinuerin inhibitor or a corticosteroid.

[42] The method of method of any one of paragraphs 40-41, wherein the additional agent has anti-itch properties.

[43] A method of preventing or treating one or more sensation arising from an irritation, urticaria, pain, inflammation, asthma, allergy, allergic rhinitis, inflammatory bowel disease and irritable bowel disease in a subject, the method comprising administering a therapeutically effective amount of an MRG receptor antagonist to the subject.

[44] The method of paragraph 43, whereby the itch sensation is reduced.

[45] The method of paragraph 43 or 44, wherein the MRG receptor antagonist also antagonizes an NK1 receptor.

[46] The method of any one of paragraphs 43-45, wherein the MRG receptor antagonist is a tri-peptide QWF (Gln-Trp-Phe) or an analog or a derivative thereof.

The method of paragraph 46 wherein the tri-peptide QWF is [Boc-Gln-D-Trp(Formyl)-Phe benzyl ester] or the tri-peptide QWF [Gln-D-Trp(Formyl)-Phe benzyl ester] or an analog or a derivative thereof.

[48] The method of any one of paragraphs 43-47, wherein the MRG receptor is MRGPRX1.

[49] The method of any one of paragraphs 43-47, wherein the MRG receptor is not MRGPRX1.

[50] The method of any one of paragraphs 43-49, wherein the MRG receptor is MRGPRX2.

[51] The method of any one of paragraphs 43-50, wherein the MRG receptor antagonist is administered topically to the subject.

[52] The method of any one of paragraphs 43-51, wherein the MRG receptor antagonist is contained in a topical formulation and the topical formulation is selected from the group consisting of a solution, a suspension, a lotion, a gel, a cream, a foam, a eutectic mixture, an ointment and an emulsion.

[53] The method of paragraph 52, wherein the formulation is associated with a skin patch device.

[54] The method of any one of paragraphs 43-53, wherein the MRG receptor antagonist is administered systemically to the subject.

[55] The method of paragraph 54, wherein the administration is selected from the group consisting of oral, parenteral, introatracheal, intrathecal, intracranial, intrarectal, intranasal, intravenous, intramuscular, intraperitoneal, intracerebrospinal, subcutaneous, intraepidermal, intra-arterial and intrasynovial administration.

[56] The method of any one of paragraphs 43-55, the method further comprising administering an additional anti-itch agent to the subject in combination with the MRG receptor antagonist.

[57] The method of paragraph 56, wherein the additional anti-itch agent is selected from the group consisting of a mast cell stabilizer, a TRP channel inhibitor or activator, and an inhibitor of a nerve growth factor receptor, e.g., TrkA.

This disclosure is further illustrated by the following example which should not be construed as limiting. The contents of all references cited throughout this application, as well as the figures and table are incorporated herein by reference.

EXAMPLES

Materials and Method

Peptides and Chemicals:

Substance P (SP) was synthesized by GenScript and dissolved in 1× Phosphate buffered saline (PBS) and 0.5 M sodium acetate, pH 6.5. The SP antagonists, QWF (Boc-Gln-D-Trp(Formyl)-Phe benzyl ester trifluoroacetate) and aprepitant, were obtained from SIGMA and THERMO FISHER, respectively.

Cell Culture:

HeLa cells were obtained from the ATCC and maintained in DMEM supplemented with 10% fetal bovine serum (FISHER Biochemicals), L-glutamine, penicillin and streptomycin.

Animals:

Mrgpr cluster Δ−/− and NK1−/− mice were generously provided by Xinzhong Dong at Johns Hopkins, Baltimore, Md. and Norma Gerard, Children's Hospital, Boston, Mass., respectively. C57BL/6 mice were purchased from Jackson Laboratory. All experiments were reviewed and approved by Institutional Animal Care and Use Committee (IACUC) at Massachusetts General Hospital.

cDNA Clones:

human MRGPRX2 was isolated by PCR from human genomic DNA using the forward and reverse primers, CTCGAGAGCATGGATCCAACCACC (SEQ. ID. NO: 3) and AAGCTTCTCTACACCAGACTGCTTCTCG (SEQ. ID. NO: 4), and cloned into pcDNA3.1(−). The mouse MrgprA1 cDNA expression clone was purchased from ORIGENE Technologies. The mouse MrgprB2 coding sequences were PCR-amplified from mouse genomic DNA using the primer pair, CTCGAGAACATGAGTGGAGATTTCCTAATCAAG (SEQ. ID. NO: 5) and AAGCTTTCAGCTGCAGCTCTGAACAGTTTCCAG (SEQ. ID. NO: 6), and cloned into pcDNA3.1 (−).

Human NK1 cDNA was obtained from LIFE Technologies, PCR cloned with Xho I-Hind III ends and cloned into pcDNA3.1(−). Mouse NK2 and NK3 expression-ready vectors were obtained from GENSCRIPT (Piscataway, N.J.). All other Mrgprs (human MRGPRX1, human MRGPRX2, human MRGPRX3, human MRGPRX4, mouse MrgprA2a, mouse MrgprA2b, mouse MrgprA3, mouse MrgprA4, mouse MrgprA9, mouse MrgprA10, mouse MrgprB4 and mouse MrgprB5) were cloned by PCR from genomic DNAs and inserted into pcDNA3.1 (−).

Calcium Imaging of Transfected HeLa Cells:

10 μg of expression vector (human MRGPRX2, mouse MrgprA1 or NK1) and 10 μl of LIPOFECTAMINE 2000 transfection reagent were diluted into 0.5 ml of DMEM and separately left at room temperature (RT) for 5 min. They were then mixed and incubated at RT for 20 minutes prior to being added to HeLa cells. HeLa cells were grown to confluence, trypsinized and 1×10$^6$ cells were pelleted in a 15 ml tube by centrifugation at 1000 rpm for 5 minutes. The DMEM-LIPOFECTAMINE 2000-DNA mixture (1 ml) was then added to the cell pellet, suspended and incubated at RT for 5 minutes. 2 ml of complete DMEM with 10% FBS without antibiotics were added to the tube, mixed by inverting the tube, plated into a 96-well glass bottom plate at 50,000 cells/well, and placed in a 37° C. CO$_2$ incubator for 3 hours. HeLa cells transfected with salmon sperm DNA were plated as a control. The medium was changed after 3 hours and left in the incubator. 24 hours after transfection, the medium in the wells was removed and 100 μl of complete DMEM containing 2 μM of FURA-2 were added to each well and left at room temperature in the dark for 1 hr. Following loading with FURA-2, the medium was removed, washed with PBS and replaced with 90 μl of HEPES-buffered saline (20 mM HEPES, 115 mM NaCl, 5.4 mM KCl, 2 mM CaCl$_2$, 0.8 mM MgCl$_2$, 13.8 mM glucose, pH 7.4).

Calcium imaging was performed immediately after loading cells with Fura-2, using a ZEISS Axiovert 200M microscope platform equipped with a flipping filter wheel for ratiometric imaging. Axiovision software, version 4.6 was used for calcium image analysis of the cells excited at 340 nm and 380 nm. Agonists were added at 15 seconds after the start of the excitation procedure. Antagonists were added five minutes before imaging with the agonists. Images were taken every 5 seconds, including at zero time, during a 90 second period or longer if required. The software later analyzed all images taken during each excitation period. Ratiometric changes were measured in 10-20 cells in each individual experiment. An average of the fluorescence of the cells in each image was calculated and plotted against time in seconds.

Concentration-Effect Measurements for Substance P:

HeLa cells transfected with human MRGPRX2, mouse MrgprA1 and NK1 cDNAs were subjected to ratiometric imaging as described above with SP at concentrations from 0.1 nM-50 μM. Each of the concentration dependent readings was performed in triplicate. Maximum intensities at each of the dilutions were calculated and plotted against concentration using GraphPad Prism software. Error bars represent SEM.

DRG Culture and Calcium Imaging:

Cervical to lumbar dorsal root ganglia (DRG) from C57/B6 or NK1 mice (1 month old) were dissected and maintained in DMEM (GIBCO, Langley, Okla., USA), containing 200 mM L-glutamine (FISHER SCIENTIFIC, Pittsburgh, Pa., USA), 10% heat inactivated fetal bovine serum (GIBCO, Langley, Okla., USA), 5000 U/ml penicillin and 5000 μg/ml streptomycin (FISHER SCIENTIFIC, Pittsburgh, Pa., USA). Enzymatic digestion was carried out with 1 mg collagenase in 1 ml dispase (ROCHE Applied Sciences, IN, USA), at 37° C. for 70 min. The collagenase/dispase solution was removed, and DRGs were washed and suspended in DMEM containing 125 U DNAse (SIGMA, St Louis, USA) within which the ganglia were mechanically triturated using fire-polished glass pipettes. These cells were centrifuged over a 10% bovine serum albumin solution (BSA; SIGMA, St Louis, USA) gradient, pelleted and suspended in Neurobasal medium (GIBCO; Langley, Okla., USA) supplemented with B27® (INVITROGEN, Carlsbad, USA), nerve growth factor (NGF; INVITROGEN, Carlsbad, USA), glial cell-derived neurotrophic factor (GDNF; SIGMA, St Louis, USA) and arabinocytidine (Ara-C; SIGMA, St Louis, USA). The cells were plated onto glass bottom 35 mm dishes coated with 10 μg/ml laminin (SIGMA, St Louis, USA) and cultured for 24 h. For calcium imaging experiments, neurons were loaded for 30 min with 10 μM of FURA-2 AM (LIFE TECHNOLOGIES, CA, USA) in Neurobasal medium, washed with Standard Extracellular Solution (SES; 145 mM NaCl, 5 mM KCl, 2 mM CaCl$_2$, 1 mM MgCl$_2$, 10 mM glucose, 10 mM HEPES, pH 7.5), and imaged at room temperature. Cells were evaluated using a NIKON Eclipse Ti inverted microscope equipped with an Exi Aqua CCD camera (QIMAGING, British Columbia, Canada). Ca$^{2+}$ flux fluorescence was measured as an absorbance ratio at 340 nm and 380 nm (F340/380) (Lambda DG4, Sutter Instruments, Novato, Calif., US). The 340/380 ratiometric images were analyzed using NIKON Elements AR Software (NIKON, Melville, N.Y. USA). Substance P (SP; 10, 30, 100, 300 and 1000 nM) and QWF (1 μM) solutions were delivered directly onto neurons, at a flow rate at 2 ml/min for 20 seconds, using perfusion barrels followed by buffer washout and further application. 1 μM allyl isothiocyanate (AITC; SIGMA, St Louis, USA), 1 μM capsaicin (TOCRIS Bioscience, Bristol, United Kingdom) and 40 mM KCl (SIGMA, St Louis, USA) were applied at the end of each experiment.

Behavioral Studies:

The mouse cheek model was used to evaluate scratching behavior in Mrgpr cluster Δ−/− and NK1−/− mice. Mice used for behavioral studies were 2 to 3 months old, 20-30 g. Mice were habituated for 30 minutes/day for 3 days prior and for 15 minutes on the day of the study. 10 µl of each compound were delivered by a 31G needle to the cheek. The mice were not shaved prior to injections to avoid irritation. All experiments were performed at consistent times during the day (9:00 am to 2:00 pm) and under the same conditions and in groups of at least 7 mice. The mice were videotaped in a soundproof environment minimize distraction. Recordings were scored for the number of scratching bouts that occur over 1 minute intervals during 25 minute observation periods and the investigator was not aware of the group allocation during scoring the study and behavioral analysis. A scratching bout was initiated by lifting of the hind paw to the area of injection, and ended by returning of the hind paw to the floor or to the mouth. Compounds injected: Substance P (500 µM), Compound 48/80 (500 µM), SLIGRL (SEQ ID NO: 7) (500 µM), L733060 (500 µM), and QWF (500 µM).

Human LAD2 Mast Cell Culture:

The human LAD2 mast cell line (from D. Metcalfe, National Institute of Allergy and Infectious Diseases, NIH, Bethesda, Md.) was cultured in StemPro-34 SFM medium (LIFE TECHNOLOGIES) supplemented with 2 mM L-glutamine, 100 U/ml penicillin, 100 µg/ml streptomycin, and 100 ng/ml recombinant human stem cell factor (PEPROTECH). The cells were maintained at $0.25-5 \times 10^5$ cells/ml at 37° C. and 5% $CO_2$ and hemi-depleted each week.

Human LAD2 Mast Cell Degranulation Assay:

Degranulation was measured as described previously (36). In brief, LAD2 cells were preincubated with 100 µM QWF for 10 min before activation by agonists at indicated concentrations for 30 min. The level of mast cell degranulation was assessed by the release of β-hexosaminidase in mast cell granules, quantified by the level of its substrate p-nitrophenyl N-acetyl-β-$_D$-glucosamide (PNAG) digested in a colorimetric assay.

Statistical Analysis:

For behavioral studies, average numbers of scratching bouts were compared across groups using one-way ANOVA. Pair-wise comparisons were performed using student t test after correcting p values for multiple comparisons using the Bonferroni procedure. For DRG studies and mast cell degranulation studies, unpaired student t-test was used. Differences were considered to be statistically significant for $P < 0.05$. Data analysis was performed using PRISM 6.

Example 1

Substance P (SP) is an inflammatory neuropeptide implicated in itch. While the classic receptor for SP is neurokinin-1 (NK-1), the inventors have found that SP activates other receptors in addition to NK1. In particular, they have determined that SP activates the mouse receptor MrgprA1 and the homologous human receptor MRGPRX2, which are necessary to induce itch (FIGS. 1 and 2).

Figure 3:
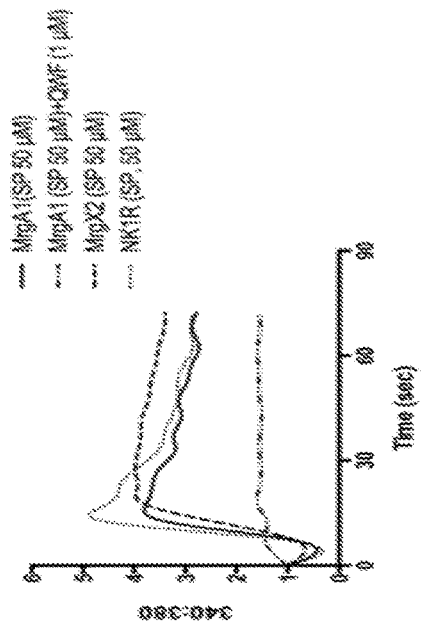
FIG. 3 shows that the tripeptide, QWF, blocks scratching in mice provoked by pruritogens. Substance P (SP), compound 48/80 and SLIGRL (SEQ ID NO: 7) all provoke itch in mice when injected into the cheek. When pruritogens are co-injected with QWF, scratching bouts are reduced to baseline. All of the pruritogens are acting through the MrgprA1 receptor. While SP was thought to act through the NK I receptor, the role of this receptor is small, as shown by the lack of significant blockade by L733060, a NK1 antagonist. QWF blocks both the NK1 and MrgprA1 receptors but it is the effect on the latter that is relevant.

A tri-peptide comprising modified amino acids QWF (glutamine-tryptophan-phenylalanine) was found to inhibit NK1. QWF significantly decreases SP-induced itch in mice (FIG. 3).

Figure 2:
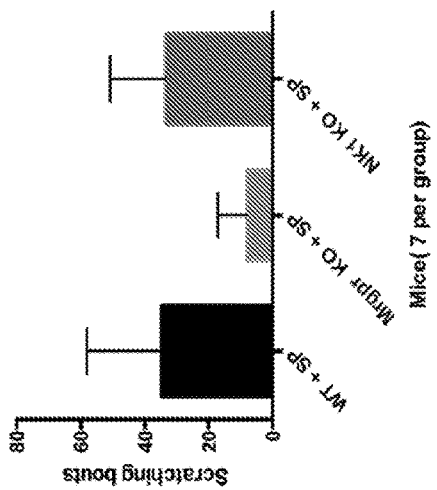
FIG. 2 shows that SP-induced itch is significantly decreased in Mrgpr cluster knock out (Mrgpr KO) mice.

The inventors have determined that QWF is an excellent inhibitor of mMrgprA1 and hMRGPRX2 (FIG. 1). Furthermore, they compared the ability of QWF to suppress SP-induced itch in mice to that of L733060, a known NK1 inhibitor. QWF significantly decreases SP-induced itch (p-value 0.0006), but L733060 does not significantly decrease SP-induced itch (p-value 0.0584) (FIG. 3). These results highlight the role of Mrgprs in SP-induced itch for the first time and also identify QWF as an anti-itch composition.

Example 2

Histamine dependent and independent pathways mediate itch through activation of GPCRs. The importance of histamine independent pathways has become clear, as antihistamines have been found to have little clinical benefit. Mrgprs are innate sensors and candidate GPCRs for mediating itch independently of histamine. Substance P (SP) evokes itch that is histamine independent. The classical receptor for substance P is the neurokinin-1 GPCR but antagonists to this receptor have not been proven effective in relieving itch. Here it is shown that SP mediates itch via MrgprA1 in mice and activates MrgprX2 in humans and that a small molecule blocks receptor activation and itch.

In 2001, comparison of cDNA libraries from wild type (WT) and mice lacking the transcription factor neurogenin 1 led to the discovery of genes encoding a new family of GPCRs, now known as Mas-related G protein-coupled receptors (Mrgprs) (1). Mrgprs were found to be identical to a group of orphan receptors known as sensory neuron-specific G-protein coupled receptors (SNSRs), on human and rat small sensory neurons implicated in nociception (2). Several factors support the concept of Mrgprs serving as innate sensors in general and as sensors for pruritogens specifically. Mrgprs first appear in tetrapods (3), animals endowed with the capacity to remove exogenous agents by scratching while navigating on land. Mrgprs demonstrate high constitutive activity and respond to several ligands, many of which are pruritogens (3-7). The tissue distribution of Mrgprs is limited primarily to where sensors are needed—sensory nerves and, for certain members, mast cells (3, 4, 8, 9). The interaction between Mrgprs and substance P has not been investigated previously with respect to sensory processing.

SP is a potent endogenous pruritogen in mice (10) and human (11). It belongs to a family of structurally related peptides known as tachykinins that are derived from alternative processing of the Tac genes (12). Tachykinins are expressed throughout the peripheral and central nervous, immune, and gastrointestinal systems and regulate a diverse range of physiologic processes. Tachykinins have been considered to interact with three neurokinin receptors (NKRs) coded by three Tact genes (13). The possibility that SP interacts with a receptor other than NK1 to mediate nociceptive effects was suggested as far back as 1984 (14). The level of NK1R mRNA in the dorsal horn of the spinal cord is insufficient to account for the high level of SP binding in this region, suggesting that NK1R could not account for all of the SP binding activity (15).

SP does not Induce Itch in Mrgpr Cluster KO Mice.

Figure 4:
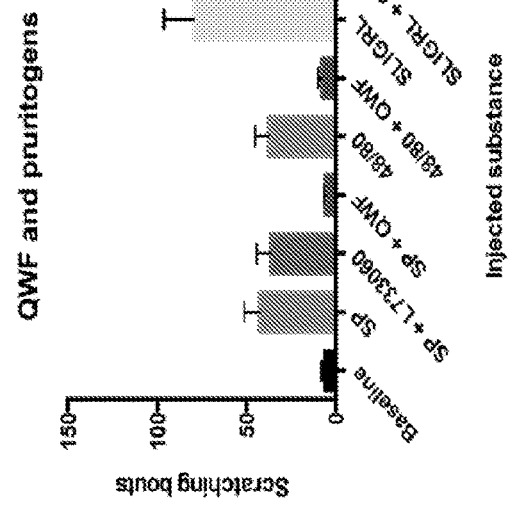
FIG. 4 shows that Substance P (SP) provokes itch in wild type (WT) mice to a similar degree to that in NK1 knockout mice but does not provoke itch in Mrgpr cluster knockout mice. The difference in the number of scratching bouts provoked by substance P in WT and NK1 knockout mice is not significant (P value=0.505). In contrast, the difference in the number of scratching bouts provoked by substance P in WT and Mrgpr cluster knockout mice is significantly (P value=0.044).

To evaluate the role of Mrgprs in SP-induced itch, the inventors performed behavioral itch studies using the mouse cheek model which differentiates itch from pain (16). As shown in FIG. 4, they examined responses in wild type (WT), neurokinin-1 knock out (NKI KO), and Mrgpr cluster KO mice in which genes coding for 12 Mrgprs have been knocked out (5). SP-induced itch in WT and NK1 KO mice but not in Mrgpr cluster mice. This finding implicated at least one of the 12 Mrgprs in SP evoked scratching.

SP Specifically Activates mMrgprA1 and hMRGPRX2 in Addition to NK1.

To identify the Mrgprs activated by SP, calcium imaging was performed on cells transfected with cDNAs encoding the four human Mrgprs, hMRGPRXI, hMRGPRX2, hMRGPRX3, hMRGPRX4, and 9 of the 12 mouse Mrgprs deleted in the Mrgpr cluster KO mice (sequences of Mrpgrs A12, A16, and 19 are not yet available). SP specifically activated cells expressing hMRGPRX2 and mMrgprA1 with equal potency to NK1R, but not other Mrgprs.

The NK1 Antagonist QWF Inhibits hMRGPRX2, mMrgprA1 and Itch from SP.

The activation of hMRGPRX2 by SP may have clinical relevance to itch and urticarial (17). An MRGPRX2 antagonist could be useful but none have been reported. Numerous NK1 antagonists have been developed, and considered for itch, but results from human studies have been inconsistent (18-20). Because SP interacts with NK1 and Mrgprs, the inventors asked if known NK1 antagonists might also block the pharmacological and behavioral effects of SP on Mrgprs. If so, the inconsistency in the effectiveness of NK1 inhibitors on itch in animal and human studies could be explained.

The NK1 antagonists aprepitant and L-733060 did not impact Mrgprs. In contrast, the inventors identified QWF as a potent antagonist of hMRGPRX2 and mMrgprA1. Next, they performed behavioral studies in WT mice to evaluate the effect of QWF on SP-induced itch. QWF decreased SP-induced itch to baseline while L-733060, frequently used in mouse studies, was only minimally effective. This result is consistent with the finding above that SP evokes scratching in NK1 KO mice. SP-evoked scratching is thus mediated primarily by MrgprA1 rather than NK1.

QWF Blocks the Effects of SLIGRL (SEQ ID NO: 7), and Compound 48/80 on Mrgprs.

Additional pruritogens activate Mrgprs and this activation has been used to suggest functional homologies between specific mouse and human receptors. Some of these pruritogens also activate PAR2. The present inventors evaluated the capacity of QWF to impact receptor activation by the pruritogens SLIGRL (SEQ ID NO: 7) and compound 48/80 in DRGs and transfected cells. SLIGRL (SEQ ID NO: 7), the tethered hexapeptide ligand of mouse PAR2, is used widely to study histamine-independent itch (7). SLIGRL (SEQ ID NO: 7) activates not only PAR2 but also mMrgprC11 and hMRGPRX2. QWF inhibits the SLIGRL (SEQ ID NO: 7) activation on the Mrgprs but not PAR2.

Compound 48/80 is a polymer that induces mast cell degranulation and evokes itch in humans and scratching in mice (10, 21). It had been thought that compound 48/80 evokes itch via mast cell degranulation and was thus histamine-dependent. It was subsequently determined that compound 48/80, and SP, induce similar numbers of scratching bouts in WT and mast cell deficient mice. These results revealed that mast cells were not critical for itch evoked by these compounds (10). Compound 48/80 has also been shown to interact directly with sensory nerves, potentially through Mrgprs (22). Because QWF inhibited the interaction of SP with NKI and Mrgprs, the inventors next examined the capacity of QWF to inhibit receptor activation and scratching from compound 48/80. Compound 48/80 activates hMRGPRX2, mMrgprA1, mMrgprC11, mMrgprB2, mMrgprA10, mMrgprA2 and PAR2 but not NK1. QWF antagonizes the activation of the Mrgprs and PAR2 by compound 48/80 and blocks compound 48/80-induced itch to baseline.

DRG Studies

To further evaluate the interaction of SP and mMrgprA1, the inventors cultured DRGs from NK1 KO mice and evaluated their response to SP with calcium imaging. The inventors have demonstrated that NK1 KO DRGs are activated by SP at nanomolar concentrations. They next repeated the experiments in the presence of QWF and the response of the DRGs to SP was significantly diminished. The inventors also demonstrate that QWF significantly decreases the response of WT DRGs to compound 48/80.

Substance P an Endogenous Ligand for hMRGPRX2, an Orphan Receptor with Multiple Ligands.

The appearance of Mrgprs in tetrapods, high constitutive activity, narrow tissue distribution to DRGs and mast cells (3, 4), makes these receptors excellent candidates as sensors to detect a wide range of environmental insults from microbial and macroorganisms to plants and chemicals. Receptor activation would lead to scratching behavior directed at repelling such insults. Mrgprs respond to a diverse range of ligands, consistent with a sensing role. While Mrgprs had been considered orphan receptors as endogenous ligands, including cortistatin-14 and the proadrenomedullin C-terminal peptides PAMP-12 and -20 activate hMRGPRX2, but their tissue distribution does not overlap (23, 24). The inventors reported that cathepsin S, an endogenous cysteine protease implicated in itch, activates mMrgprC11 and hMRGPRX2, The established link between SP and itch and here, the activation of mMrgprA1 and hMRGPRX2, indicate that these receptors are no longer orphans.

Functional homology of Mrpgs within and between mice and humans is based on ligand specificity, as sequence homology has not been predictive. inMrgprA3 and hMRGPRX1 respond to chloroquine and are considered homologous (5). mMrgprXl (also known as mMrgprC11) and hMRGPRX1 respond to BAM22 (2). MrgprD in both mice and humans is activated by B-alanine (6). hMRGPRX2 has a wider expression pattern when compared to other Mrgprs, being highly expressed on mast cells in addition to DRGs. It has been suggested that mMrgprB2 on mast cells is homologous to hMRGPRX2 but hMRGPRX2 is much more sensitive to SP than mMrgprB2 (9). The data presented here, that at nanomolar concentrations, SP activates mMrgprA1 and hMRGPRX2, suggest that these receptors have functional homologies.

The results reveal that mMrgprA1 is essential for SP-induced itch. In addition it is demonstrated that QWF inhibits activation of mMrgprA1, mMrgprB2 and hMRGPRX2 by SP and compound 48/80. It is recognized that NK1 may be modulating SP-induced itch at some level but the present inventors conclude that NK1 is not the major mediator of SP-induced itch in the periphery and this may explain the inconsistent results obtained with NKI inhibitors for the treatment of itch. In addition to SP and compound 48/80, other peptides including B-defensins and LL-37 also induce mast cell degranulation by activation of hMRGPRX2 (25, 26) but their direct involvement in itch is not clear for several reasons. First, mast cell degranulation may contribute to inflammation but may not necessarily induce itch, as demonstrated by our behavioral studies (supplemental data: PAMP and LL-37 don't cause itch) and previous studies in mast cell deficient mice (10). Second it has been demonstrated that coupling of MrgprA3 and C11 to transient receptor potential channel AI (TRPAI), is necessary for transmitting histamine-independent itch (27, 28) and that coupling to transient receptor potential cation channel VI (TRPVI) is required for histamine-induced itch (29). Mrgprs including hMRGPRX2 activate multiple second messenger signaling pathways (3, 4, 24, 25) that don't necessarily couple to the downstream pathways transmitting itch. Consistent with this hypothesis, previous studies have demonstrated that SP-induced itch is impaired in TRPA1 KO mice suggesting that TRPA1 is necessary for SP-induced itch and that TRPA1 may be downstream of the primary receptors transmitting SP-induced itch (30).

The most abundant human Mrgpr expressed on mast cells, is hMRGPRX2 (3, 4, 8). The expression pattern of hMRGPRX2 and its ability to induce IgE-independent degranulation of mast cells, along with its interaction with SP, underscore the role of hMRGPRX2 in neurogenic inflammation and the crosstalk between the nervous and the immune systems. These findings support previous studies that demonstrate the role of the nervous system in inflammatory conditions including eczema and psoriasis (31, 32). The present data are consistent with SP functioning as a messenger between the nervous and immune systems and that SP is the endogenous ligand for hMRGPRX2. hMRGPRX2 has been implicated in IgE-independent mast cell degranulation associated with allergy and drug reactions and may be amenable to blockage by receptor inhibition (9). As SP activation of mMrgprA1 causes scratching in mice, and is blocked by QWF, it is possible that SP activation of hMRGPRX2 in humans induces itch that could likewise be inhibited by blockade of hMRGPRX2.

REFERENCES FOR EXAMPLES 1 AND 2

1. Dong X, et al. A diverse family of GPCRs expressed in specific subsets of nociceptive sensory neurons. Cell. 2001; 106(5):619-32.
2. Lembo P M, et al. Proenkephalin A gene products activate a new family of sensory neuron—specific GPCRs. Nature neuroscience. 2002; 5(3):201-9.
3. Bader M, et al. MAS and its related G protein-coupled receptors, Mrgprs. Pharmacological reviews. 2014; 66(4): 1080-105.
4. Solinski I J J, et al. Pharmacology and signaling of MAS-related G protein-coupled receptors. Pharmacological reviews. 2014; 66(3):570-97.
5. Liu Q, et al. Sensory neuron-specific GPCR Mrgprs are itch receptors mediating thloroquine-induced pruritus. Cell. 2009; 139(7):1353-65.
6. Liu Q, et al. Mechanisms of itch evoked by beta-alanine. The Journal of neuroscience the official journal of the Society for Neuroscience. 2012; 32(42):14532-7.
7. Liu Q, et al. The distinct roles of two GPCRs, MrgprC11 and PAR2, in itch and hyperalgesia. Science signaling. 2011; 4(181):ra45.
8. Tateinoto K, et al Immunoglobulin E-independent activation of mast cell is mediated by Mrg receptors. Biochemical and biophysical research communications. 2006; 349(4):1322-8.
9. McNeil B D, et al. Identification of a mast-cell-specific receptor crucial for pseudo-allergic drug reactions. Nature. 2014.
10. Andoh T, et al. Substance P induction of itch-associated response mediated by cutaneous NK1 tachykinin receptors in mice. J Pharmacol Exp 1998; 286(3):1140-5.
11. Hagermark 0, et al. Flare and itch induced by substance P in human skin. The Journal of investigative dermatology. 1978; 71(4):233-5.
12. Steinhoff M S, et al. Tachykinins and their receptors: contributions to physiological control and the mechanisms of disease. Physiological reviews. 2014; 94(1):265-301.
13. Regoli D, et al. Receptors and antagonists for substance P and related peptides. Pharmacological reviews. 1994; 46(4):551-99.
14. Shults C W et al. A comparison of the anatomical distribution of substance P and substance P receptors in the rat central nervous system. Peptides. 1984; 5(6):1097-128.
15. Maeno H, et al. Distribution of the substance P receptor (NK-1 receptor) in the central nervous system. Brain research Molecular brain research. 1993; 18(1-2):43-58.
16. Shimada S G, and LaMotte R H. Behavioral differentiation between itch and pain in mouse. Pain. 2008; 139(3):681-7.
17. Fujisawa D, et al. Expression of Mas-related gene X2 on mast cells is upregulated in the skin of patients with severe chronic urticaria. J Allergy Clin Immunol 2014; 134(3):622-33 e9.
18. Wallengren J. Topical aprepitant in clinical and experimental pruritus. Archives of dermatology. 2012; 148(8): 957-9.
19. Wallengren J, and Edvinsson L. Topical non-peptide antagonists of sensory neurotransmitters substance P and CGRP do not modify patch test and prick test reactions: a vehicle-controlled, double-blind pilot study. Arch Dermatol Res. 2014; 306(5):505-9.
20. Santini D, et al. Aprepitant for management of severe pruritus related to biological cancer treatments: a pilot study. The Lancet Oncology. 2012; 13(10):1020-4.
21. Wahlgren C F, et al. Patients' perception of itch induced by histamine, compound 48/80 and wool fibres in atopic dermatitis. Acta dermato-venereologica. 1991; 71(6):488-94.
22. Schemann M, et al. The mast cell degranulator compound 48/80 directly activates neurons. PloS one. 2012; 7(12):e52104.
23. Kamohara M, et al. Identification of MrgX2 as a human 0-protein-coupled receptor for proadrenomedullin N-terminal peptides. Biochemical and biophysical research communications. 2005; 330(4): 1146-52.
24. Robas N, et al. MrgX2 is a high potency cortistatin receptor expressed in dorsal root ganglion. The Journal of biological chemistry. 2003; 278(45):44400-4.
25. Subramanian H, et al. Mas-related gene X2 (MrgX2) is a novel G protein-coupled receptor for the antimicrobial peptide LL-37 in human mast cells: resistance to receptor phosphorylation, desensitization, and internalization. The Journal of biological chemistry. 2011; 286(52):44739-49.
26. Subramanian H, et al. beta-Defensins activate human mast cells via Mas-related gene X2. Journal of immunology. 2013; 191(1):345-52.
27. Wilson S R, et al. TRPA1 is required for histamine-independent, Mas-related G protein-coupled receptor-mediated itch. Nat Neurosci. 2011; 14 (5):595-602.
28. Wilson S R, et al. The epithelial cell-derived atopic dermatitis cytokine TSLP activates neurons to induce itch. Cell. 2013; 155(2):285-95.
29. Shim W S, et al. TRPV1 mediates histamine-induced itching via the activation of phospholipase A2 and 12-lipoxygenase. The Journal of neuroscience: the official journal of the Society for Neuroscience. 2007; 27(9): 2331-7.
30. Liu B, et al. TRPA1 controls inflammation and pruritogen responses in allergic contact dermatitis. Faseb J. 2013; 27(9):3549-63.
31. Azimi E, et al. Altered manifestations of skin disease at sites affected by neurological deficit. The British journal of dermatology. 2014.
32. Ostrowski S M, et al. Cutaneous denervation of psoriasifonn mouse skin improves acanthosis and inflammation in a sensory neuropeptide-dependent manner. The Journal of investigative dermatology. 2011; 131(7):1530-8.

Example 3

In Table 1 herein, the left hand column shows receptors that have been evaluated with respect to the tri-peptide QWF. The top row lists ligands that have been tested versus the various receptors, both in the absence and presence of QWF.

Based on data shown in the Table 1, it is concluded that QWF has the capacity to block the action of anything that causes itch where such cause involves activating the human receptor MRGPRX2. The present inventors have found that many compounds that cause itch have the ability to activate MRGPRX2. Substance P is only one of several compounds that activate MRGPRX2. The action of QWF thus includes but extends beyond substance P.

Example 4

SP Activates MrgprA1 to Induce Itch in Mice.

To evaluate the role of Mrgprs in SP-provoked itch, the inventors performed behavioral itch studies using the mouse cheek model which differentiates itch from pain (16). Behavioral responses were examined in WT, neurokinin-1 knock out (NK1−/−), and Mrgpr cluster knockout mice (Mrgpr cluster Δ−/−) in which genes coding for 12 Mrgprs have been knocked out (12). SP provoked itch in WT and NK1 mice but not in Mrgpr mice (FIG. 5a). This finding implicated at least one of the 12 Mrgprs in the itch provoked by SP.

Figure 9A:
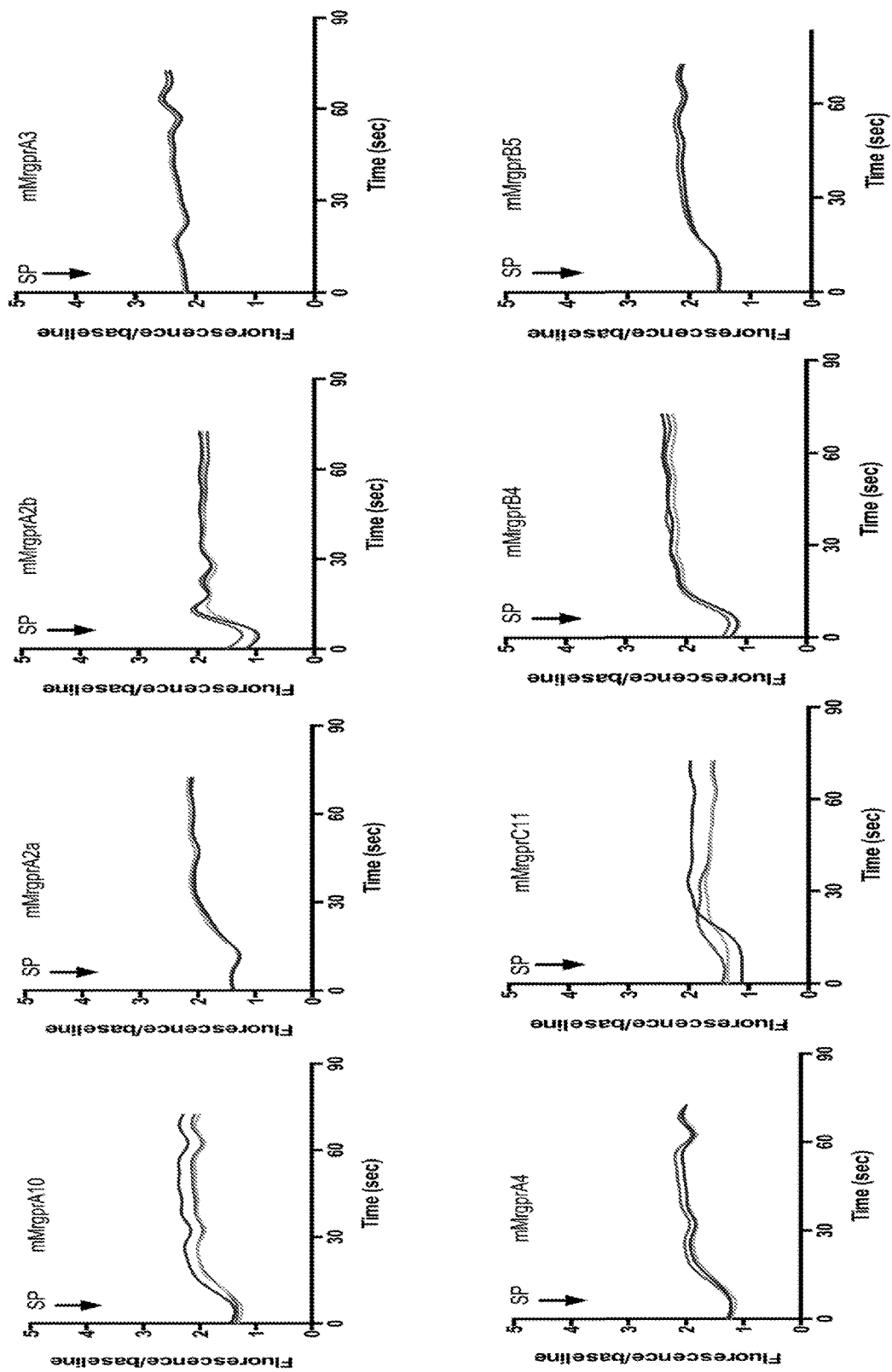

To identify the Mrgprs activated by SP, calcium imaging was performed on cells transfected with cDNAs encoding the four human Mrgprs (hMRGPRX1-4) and 9 of the 12 mouse Mrgprs deleted in Mrgpr mice (sequences of Mrpgrs A12, A16, and 19 are not yet available) (FIGS. 9a and 9b). SP specifically activated heterologous cells expressing human MRGPRX2, mouse MrgprA1 or NK1 (FIGS. 5b and 5c). SP also activated cultured dorsal root ganglion neurons from NK1 mice (FIGS. 5d and 5e). The size of the activated neurons is consistent with small diameter sensory neurons (FIG. 5f).

QWF, an Mrgpr Antagonist, Inhibits SP-Induced Itch in Mice.

As the activation of human MRGPRX2 may contribute to itch, urticaria, and pseudo-allergic drug reactions (15, 17), an antagonist of this receptor could have therapeutic benefit for itch and preventing drug reactions. No such antagonist has been reported. In contrast, numerous NK1 antagonists have been developed, and considered for itch, but results from human studies have been inconsistent (18, 19). The inventors asked if known NK1 antagonists might block the pharmacological and behavioral effects of SP on Mrgprs.

Figure 6A:
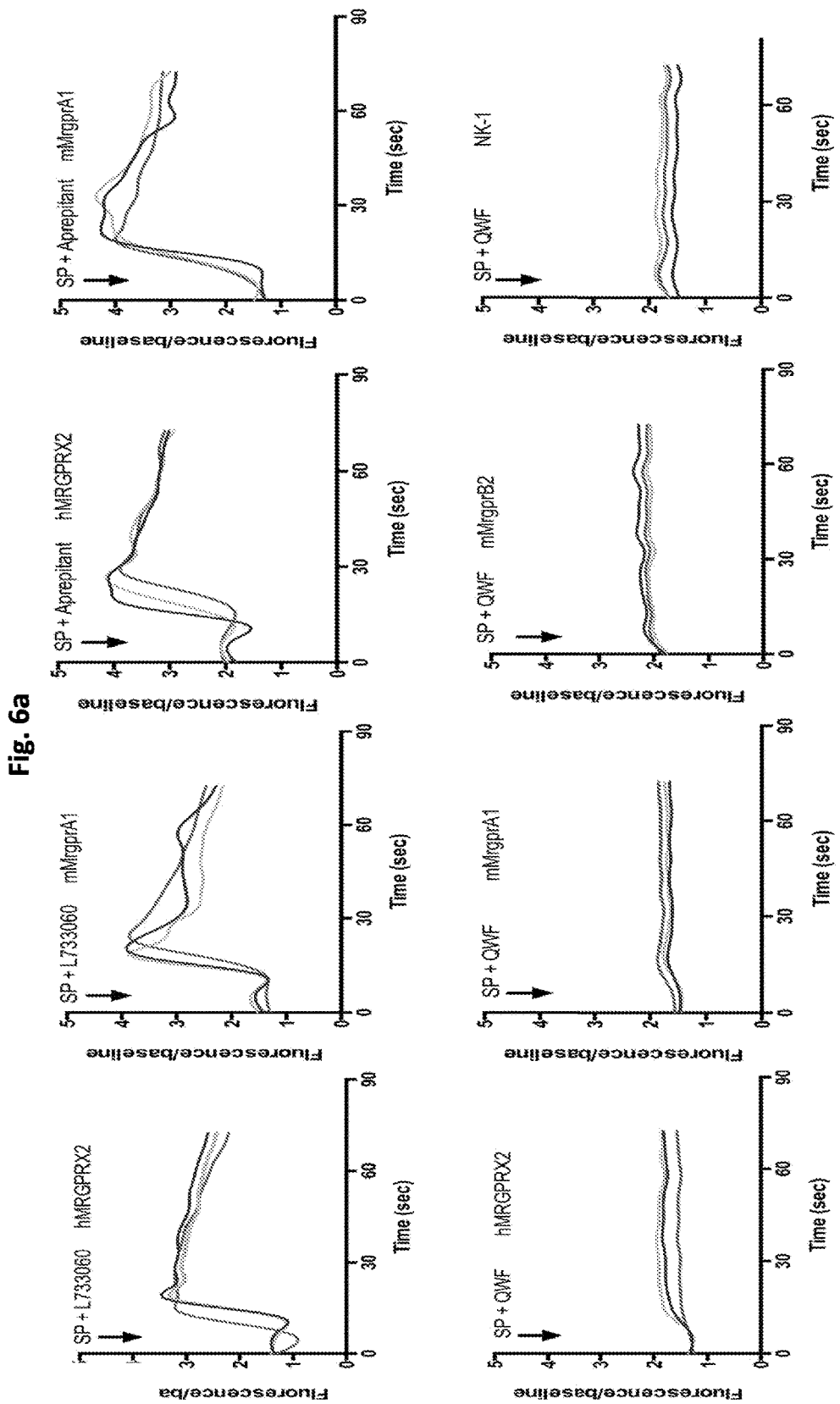
FIGS. 6a-6d show that QWF inhibits activation of Mrgprs by SP and inhibits SP-provoked itch in WT mice.
Figure 6C:
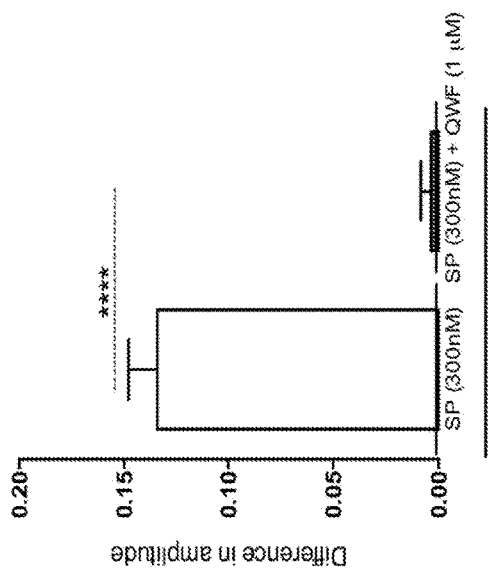
Figure 6D:
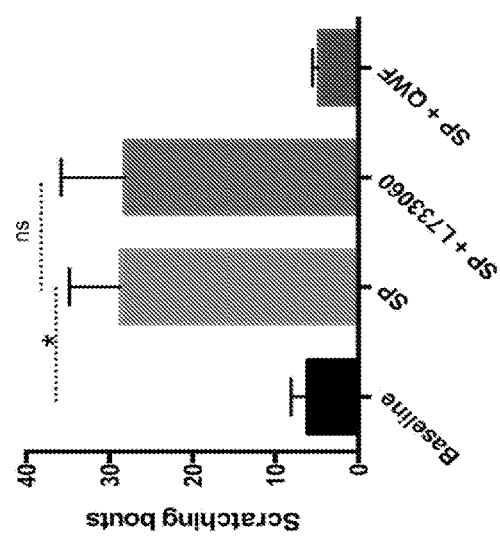
Figure 6B:
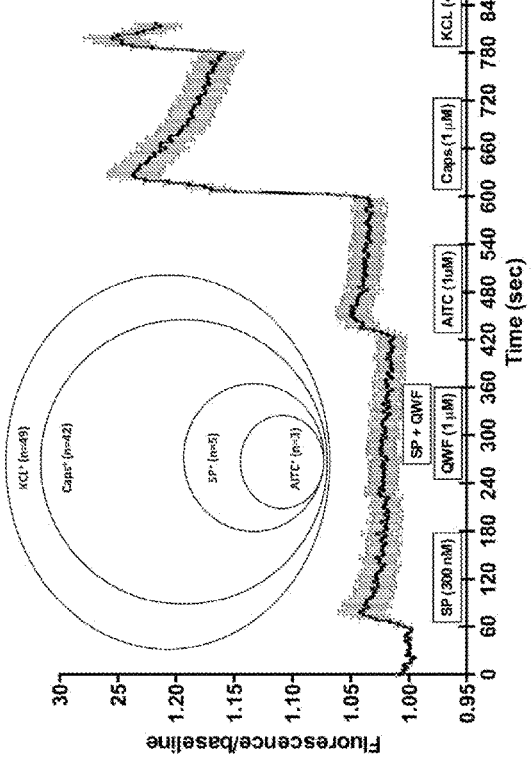

The NK1 antagonists L-733060 and aprepitant, which are structurally very similar, (FIG. 6a-6c) did not impact human MRGPRX2 or mouse MrgprA1. The inventors screened commercially available peptide antagonists of NK1 for the ability to block calcium responses in HeLa cells transfected with Mrgprs. The inventors identified the tripeptide QWF (20), as a potent antagonist of SP-induced activation of human MRGPRX2, and mouse MrgprA1 (FIG. 6d, FIG. 10). QWF also blocked SP-induced activation of cultured NK1 DRG neurons (FIGS. 6e and 6f). The majority of these neurons were responsive to the TRPA1 agonist AITC and/or capsaicin, a TRPV1 agonist (FIG. 6e). The inventors next asked if these in vitro observations could be extended in vivo. Behavioral studies were performed in WT mice to evaluate the effect of QWF on SP-provoked itch. QWF decreased SP-provoked itch to baseline while L-733060, frequently used in mouse studies, was not effective (FIG. 6g). This result is consistent with the finding above that SP provoked itch is preserved in NK1 mice. SP-provoked itch in mice is thus mediated primarily by MrgprA1 rather than NK1.

QWF Inhibits SLIGRL (SEQ ID NO: 7) and Compound 48/80-Induced Itch.

Functional homology of Mrgprs between mice and humans is based on ligand specificity, as sequence homology has not been predictive. For example mouse MrgprA3 and human MRGPRX1 respond to chloroquine (12) while mouse MrgprC11 and human MRGPRX2 respond to SLI-GRL (SEQ ID NO: 7) (13). The inventors evaluated the capacity of QWF to impact receptor activation in vitro and scratching behavior in vivo by pruritogens.

Figure 7A:
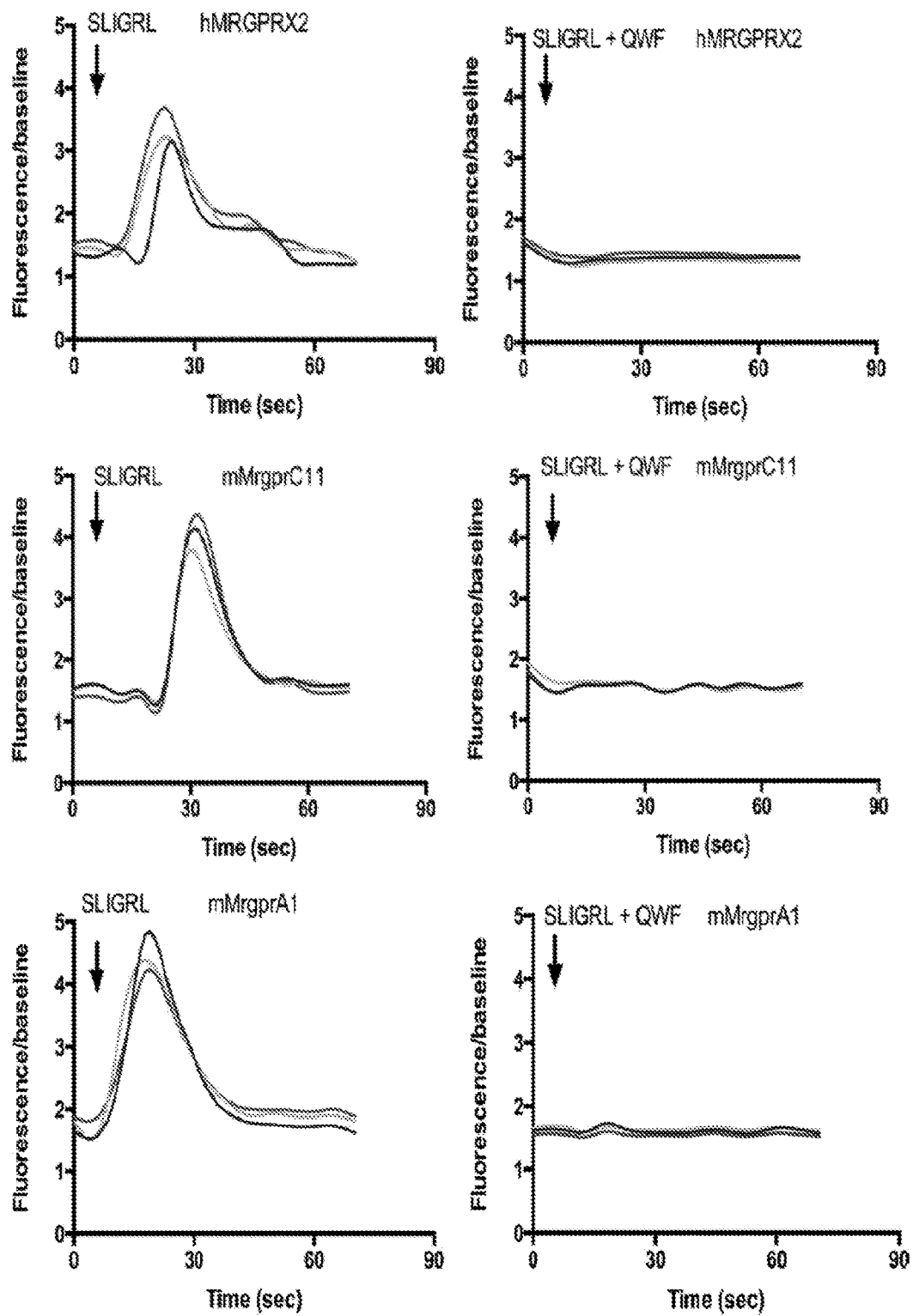
FIGS. 7a-7d show that QWF inhibits activation of Mrgprs by SLIGRL (SEQ ID NO: 7) and compound 48/80. HeLa cells were transfected with cDNAs encoding human MRGPRX2, human MRGPRX1, mouse MrgprA1, mouse MrgprA3, mouse MrgprB2, mouse MrgprC11 and intracellular calcium [$Ca^{2+}$]i determined by ratiometric FURA-2 imaging. Each trace is a response from a different cell.
Figure 7B:
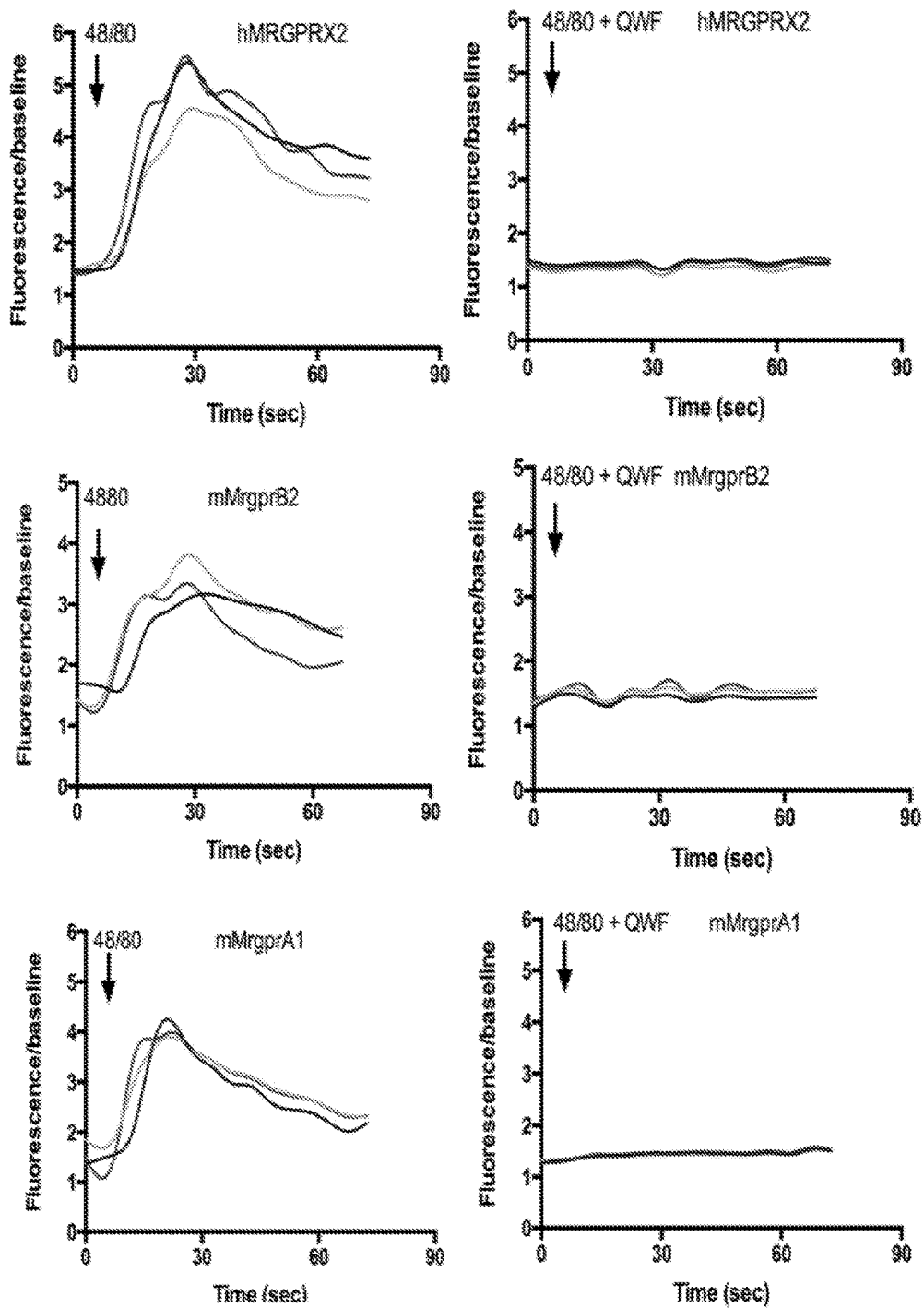
Figures 7C, 7D:
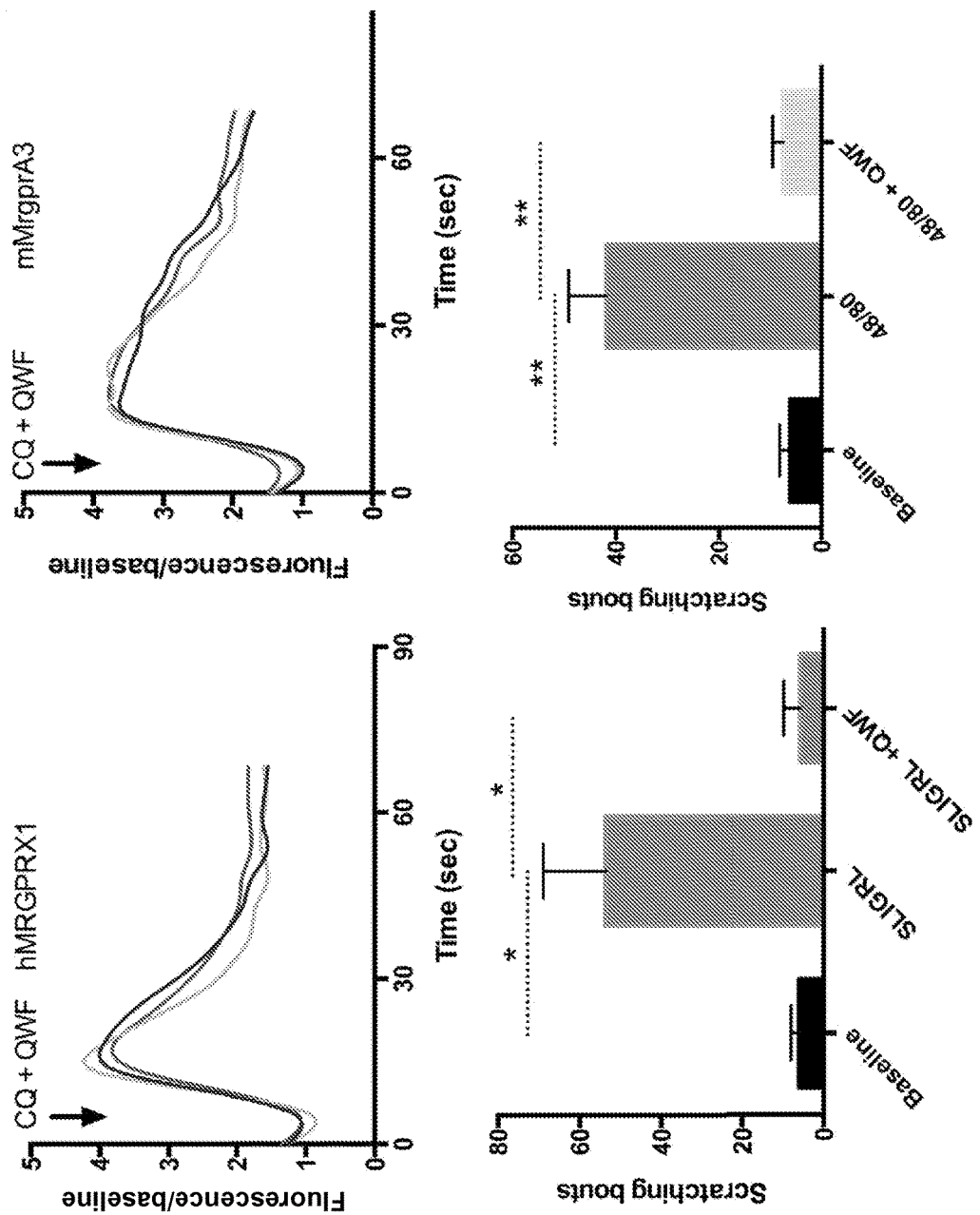
Figure 12:
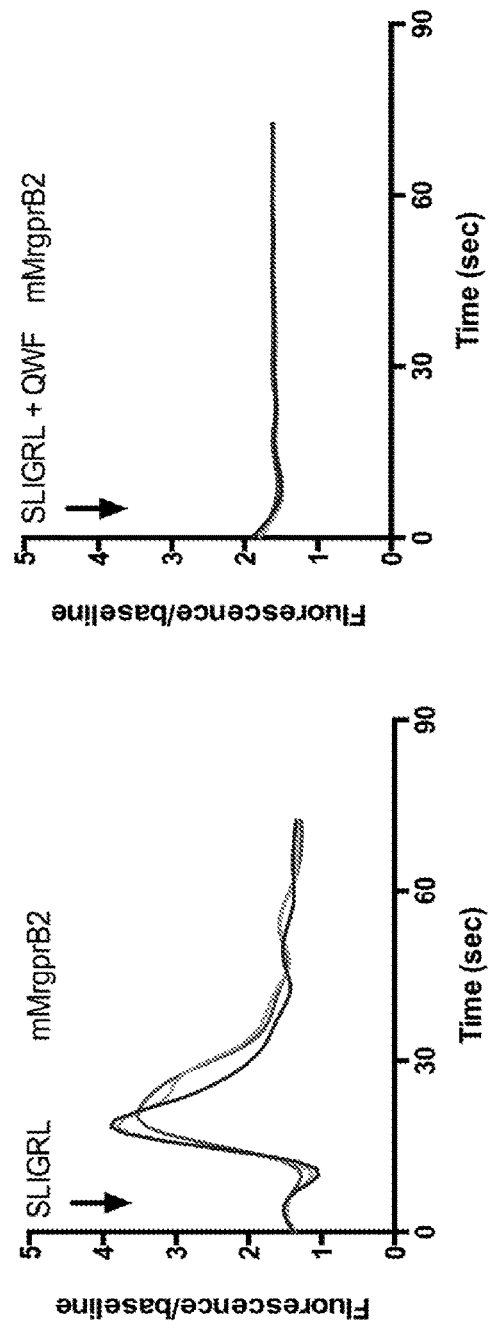
FIG. 12 shows that QWF (10 μM) inhibits activation of mMrgprB2 by SLIGRL (SEQ ID NO: 7) (10 μM). HeLa cells were transfected with cDNAs encoding mMrgprB2.

SLIGRL (SEQ ID NO: 7), the tethered hexapeptide ligand of mouse PAR2, is widely used to study histamine-independent itch (13, 21). Previous studies have demonstrated that SLIGRL (SEQ ID NO: 7) activates not only PAR2 but also mouse MrgprC11 and human MRGPRX2. SLIGRL-provoked itch ("SLIGRL" disclosed as SEQ ID NO: 7) in mice was found to be mediated by mouse MrgprC11 rather than PAR2 (13). The inventors extend this finding by demonstrating that SLIGRL (SEQ ID NO: 7) activates additional Mrgprs, specifically mouse MrgprA1 and mouse MrgprB2 (FIG. 7a and FIG. 12). QWF antagonizes the SLIGRL-induced activation ("SLIGRL" disclosed as SEQ ID NO: 7) of all of these Mrgprs in vitro (FIG. 7a) and blocks SLIGRL-provoked itch ("SLIGRL" disclosed as SEQ ID NO: 7) to baseline (FIG. 7d).

Compound 48/80 is a polymer that induces mast cell degranulation and provokes itch in humans and mice (1, 22). It had been thought that compound 48/80 provokes itch via mast cell degranulation and was thus histamine-dependent. It was subsequently determined that compound 48/80, and SP, provoke similar numbers of scratching bouts in WT and mast cell deficient mice (1). These results revealed that mast cells were not critical for itch provoked by these compounds in mice. It was suggested that mast cells may thus play a modulatory role (1). In addition, compound 48/80 directly interacts with sensory nerves, potentially through Mrgprs (23). Studies in human subjects have demonstrated that subcutaneous pretreatment with compound 48/80, inhibits SP-provoked itch (24). This observation has been confirmed in mice (1, 25) but given the fact that mast cells are not the major mediators of SP or compound 48/80-provoked itch in mice, the simple explanation that pretreatment with compound 48/80 depletes the mast cells from histamine, is not satisfactory. The direct interaction of compound 48/80 and SP with a common receptor on murine nerves, and desensitization of this receptor by 48/80 could explain this observation but compound 48/80 does not activate NK1 which, prior to the data presented here, was thought to mediate SP-provoked itch.

Since QWF antagonizes the interaction of SP with Mrgprs, the inventors examined the capacity of QWF to block receptor activation and compound 48/80-provoked itch. Compound 48/80 activates human MRGPRX2, mouse MrgprA1 and mouse MrgprB2 (FIG. 7b). QWF antagonizes the activation of the Mrgprs by compound 48/80 and blocks compound 48/80-provoked itch to baseline (FIG. 7d).

The present studies demonstrate that both compound 48/80 and SP activate mouse MrgprA1 and human MRG-PRX2. These results suggest a mast cell-independent but common pathway for compound 48/80 and SP-provoked itch. In addition, SP and compound 48/80 individually activate MrgprB2 on mouse mast cells but MrgprB2 is less sensitive than MrgprA1 and human MRGPRX2 to SP (FIG. 5c). This finding could explain the more prominent role of nerves as compared to mast cells in SP-provoked itch in mice. MrgprB2 is two orders of magnitude more sensitive to compound 48/80 than SP (15) indicating that mast cells may play a more prominent role in compound 48/80-provoked itch as compared to SP-provoked itch in mice.

The inventors next studied the interaction of QWF with human MRGPRX1 in order to evaluate the specificity of QWF. The antimalarial medication, chloroquine, activates human MRGPRX1 and mouse MrgprA3 to induce itch (12). QWF does not affect the activation of these Mrgprs by chloroquine (FIG. 7c).

Effect of QWF and Other NK1 Antagonists on Mouse MrgprB2

Figure 11:
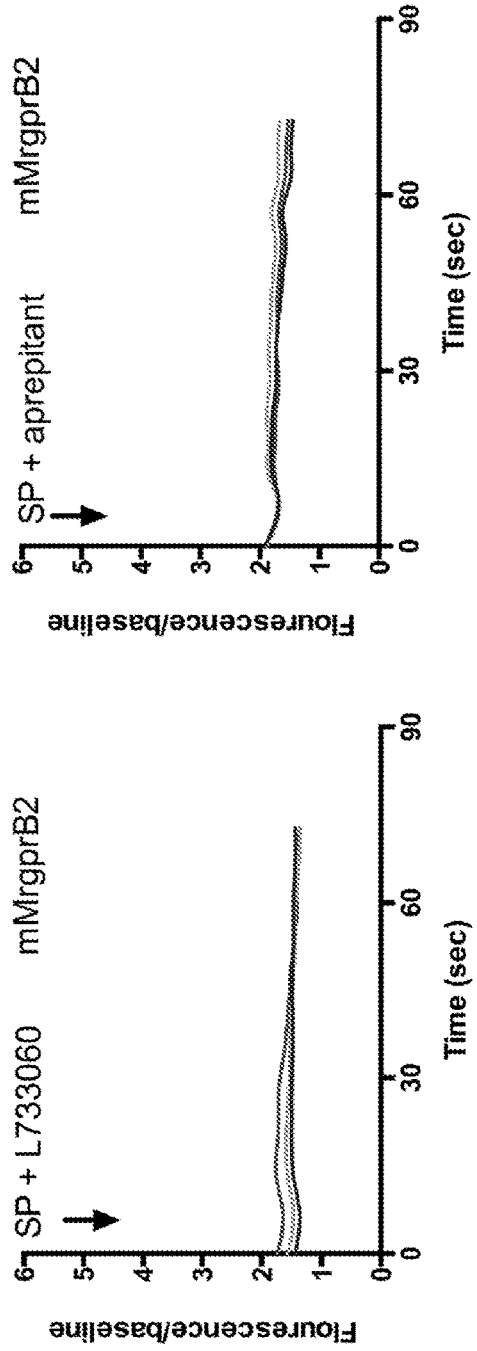
FIG. 11 shows that NK1 antagonists (50 μM) inhibit activation of mouse MrgprB2 by SP (50 μM). HeLa cells were transfected with cDNAs encoding mMrgprB2.

The inventors showed above that QWF is an antagonist of human MRGPRX2 while L733060 and aprepitant are not. As mouse MrgprB2 has been considered the orthologue of human MRGPRX2, and these receptors have been implicated in IgE-independent or so-called pseudo-allergic drug reactions, the inventors examined the effects of QWF, L733060 and aprepitant on mouse MrgprB2. Each of these compounds antagonized the activation of mouse MrgprB2 by SP (FIG. 11). This observation is critical. It can explain the inconsistencies between clinical trials of NK1 antagonists in humans and mouse models of inflammatory disease as described herein, that mouse MrgprB2 and human MRGPRX2 are important for inflammation. L733060 is effective in mouse models, most likely by antagonizing both NK1 and, as reported here, MrgprB2. Aprepitant has limited effectiveness in humans because it is an antagonist of NK1 only, and not MRGPRX2.

QWF Inhibits IgE-Independent Mast Cell Degranulation Mediated by Human MRGPRX2

Figure 8A:
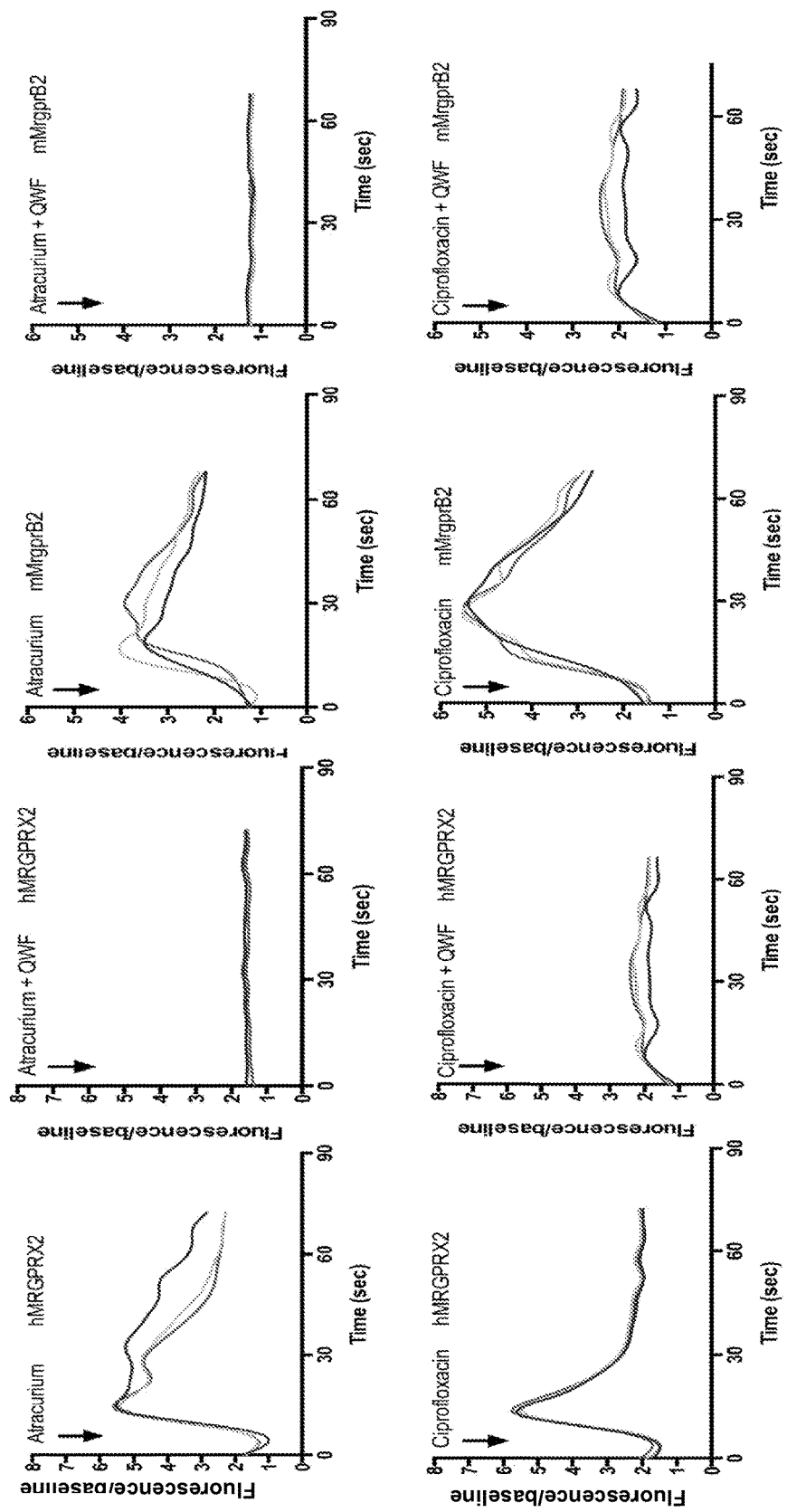
FIGS. 8a-8b show that QWF inhibits activation of human MRGPRX2 and degranulation of human LAD2 mast cells by drugs associated with pseudoallergic reactions.
Figure 8B:
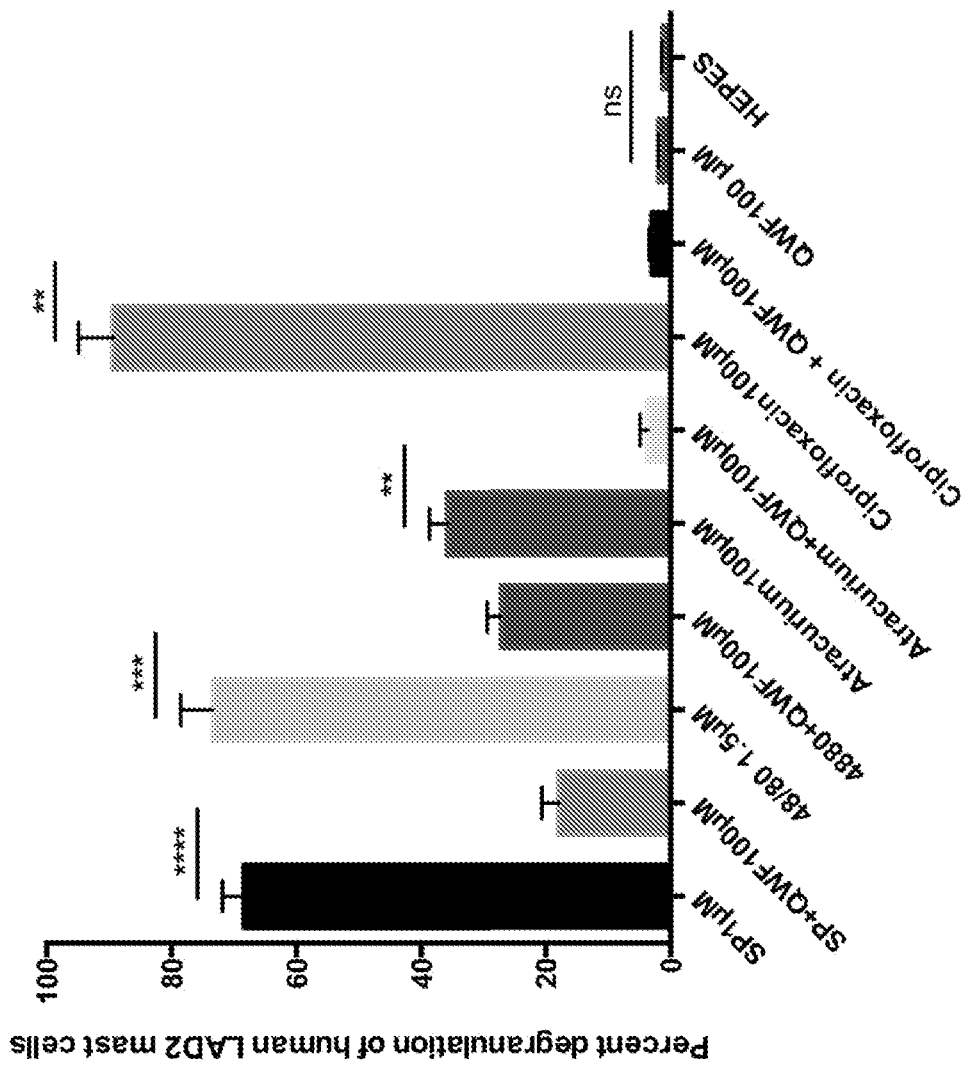

The inventors evaluated the effect of QWF on activation of human MRGPRX2 and mouse MrgprB2 by atracurium and ciprofloxacin, two medications associated with IgE-independent drug reactions. QWF antagonized the activation of Mrgprs by these drugs (FIG. 8 a). The inventors then extended these findings to human LAD2 mast cells (FIG. 8b). QWF significantly inhibits the degranulation induced by SP, compound 48/80, atracurium, and ciprofloxacin.

Mrgprs have been considered orphan receptors. MRGPRX2 can be activated by a number of peptides, including cortistatin-14, the proadrenomedullin C-terminal peptides PAMP-12 and -20, and LL-37, but physiologic consequences have not been identified (26-28). The inventors have recently reported that cathepsin S, an endogenous cysteine protease implicated in itch, activates mouse MrgprC11 and human MRGPRX2 (29). In combination with the established link between SP and itch and the activation of mouse MrgprA1 and human MRGPRX2 by this neuropeptide perhaps these receptors should no longer be considered orphans.

It has been reported that mouse MrgprB2 is the orthologue of human MRGPRX2. However, as SP is 500 times more active on the human MRGPRX2, a species-specific role for SP in humans is possible (15). The inventors demonstrate that SP not only activates MrgprB2, present on mouse mast cells, but also activates MrgprA1, on mouse DRGs. The similar number of SP-induced scratching bouts reported in wild type and mast cell deficient mice (1) can now be explained as follows. Mouse MrgprB2 is expressed on mast cells and thus absent in mast cell deficient mice. Mouse MrgprA1 is expressed, at least to an extent, on nerves in wild type and mast cell deficient mice. Previous studies have demonstrated that MrgprA1 is expressed at functional levels on nerves and that MrgprB2 is not (30). As mouse MrgprA1 is much more sensitive to SP than mouse MrgprB2, scratching in wild type and mast cell deficient mice is driven by the interaction between SP and mouse MrgprA1. The present findings with NK1 antagonists and QWF confirm these observations pharmacologically. L733060 and aprepitant, which are structurally similar, as noted earlier, are antagonists of mouse MrgprB2 but not mouse MrgprA1 while QWF is an antagonist of MrgprA1 in addition to MrgprB2. SP-induced itch is significantly decreased by antagonism of MrgprA1 by QWF but not by antagonism of MrgprB2 by L733060.

Several studies have reported the expression of MRGPRX2 on both mast cells and DRGs in humans (14, 26, 27, 31). In contrast, MRGPRX2 was not detected on human DRGs in a recent study (32). These observations can account for the inconsistent results of itch studies with SP in humans and mice. Based on our findings, SP-induced itch is primarily mediated by DRGs in mice. Activation of mouse MrgprB2 by higher concentrations of SP may explain the modulatory role suggested for mast cells in SP-provoked itch in mice (1). In humans, the expression of MRGPRX2 on mast cells has been confirmed while its expression on DRGs is fluid (15). The inventors conclude, that in contrast to mice, mast cells play an important role in SP-induced itch in humans Whether MRGPRX2 or an unidentified receptor on DRGs also contributes to SP-induced itch in humans requires further evaluation.

The interaction of SP and human MRGPRX2 underscores the role of human MRGPRX2 in neurogenic inflammation and the crosstalk between the nervous and the immune systems (10, 11, 14). These observations are consistent with the role of the nervous system in inflammatory conditions associated with SP (33). Our observations are consistent with the up-regulation of MrgprA1 on DRG neurons in a mouse model of inflammatory bowel disease (34). Whether changes in sensitivity or expression of human MRGPRX2 occur in any human disease other than urticarial (17) has not been reported.

The inventors have identified QWF as a potent antagonist of human MRGPRX2 and its homologous receptors in mice. We and others have shown that the interaction of SP with human MRGPRX2 mediates SP-induced mast cell degranulation (15, 17) and that NK1 antagonists do not inhibit SP-induced mast cell degranulation (17). The findings here with QWF confirm the importance of human MRGPRX2 in IgE-independent or pseudo-allergic reactions. Blockade of human MRGPRX2 by QWF or a derivative may prevent or ameliorate reactions to many drugs. As opposed to conventional agents, MRGPRX2 antagonists are neuro-immune modulators and may not affect overall immune responses.

In addition to blocking mast cell degranulation, QWF blocked in vitro activation of Mrgprs and in vivo scratching by pruritogens. The results reveal that interaction of SP with Mrgprs in the periphery is critical for SP-provoked itch. The inventors conclude that NK1 is not the major mediator of SP-provoked itch in the periphery although NK1 may have a modulatory role. This conclusion may not only explain the inconsistent results obtained with NK1 antagonists for the treatment of itch (18) but may also explain the disappointing results of NK1 antagonists in pulmonary and gastric disorders associated with SP (35). Thus, aprepitant may have limited effectiveness in humans because it blocks NK1 only, and not MRGPRX2. As SP activation of Mrgprs causes itch in mice and is blocked by QWF, it is possible that SP provokes itch in humans via activation of MRGPRX2. The inventors conclude that antagonists of human MRGPRX2 may be useful in the treatment of inflammatory processes, including itch, urticaria and IgE-independent allergy and drug reactions.

References for Example 4

1. Andoh, T., et al. Substance P induction of itch-associated response mediated by cutaneous NK1 tachykinin receptors in mice. The Journal of pharmacology and experimental therapeutics 286, 1140-1145 (1998).
2. Hagermark, O., et al. Flare and itch induced by substance P in human skin. The Journal of investigative dermatology 71, 233-235 (1978).
3. Steinhoff, M. S., et al. Tachykinins and their receptors: contributions to physiological control and the mechanisms of disease. Physiol Rev 94, 265-301 (2014).
4. Regoli, D., et al. Receptors and antagonists for substance P and related peptides. Pharmacological reviews 46, 551-599 (1994).
5. May, A. & Goadsby, P. J. Substance P receptor antagonists in the therapy of migraine. Expert Opin Investig Drugs 10, 673-678 (2001).
6. Butler, C. A. & Heaney, L. G. Neurogenic inflammation and asthma Inflamm Allergy Drug Targets 6, 127-132 (2007).
7. Shults, C. W., et al. A comparison of the anatomical distribution of substance P and substance P receptors in the rat central nervous system. Peptides 5, 1097-1128 (1984).
8. Dong, X., et al. A diverse family of GPCRs expressed in specific subsets of nociceptive sensory neurons. Cell 106, 619-632 (2001).
9. Lembo, P. M., et al. Proenkephalin A gene products activate a new family of sensory neuron—specific GPCRs. Nature neuroscience 5, 201-209 (2002).
10. Bader, M., et al. MAS and its related G protein-coupled receptors, Mrgprs. Pharmacological reviews 66, 1080-1105 (2014).
11. Solinski, H. J., et al. Pharmacology and signaling of MAS-related G protein-coupled receptors. Pharmacological reviews 66, 570-597 (2014).
12. Liu, Q., et al. Sensory neuron-specific GPCR Mrgprs are itch receptors mediating chloroquine-induced pruritus. Cell 139, 1353-1365 (2009).
13. Liu, Q., et al. The distinct roles of two GPCRs, MrgprC11 and PAR2, in itch and hyperalgesia. Science signaling 4, ra45 (2011).
14. Tatemoto, K., et al Immunoglobulin E-independent activation of mast cell is mediated by Mrg receptors. Biochemical and biophysical research communications 349, 1322-1328 (2006).
15. McNeil, B. D., et al. Identification of a mast-cell-specific receptor crucial for pseudo-allergic drug reactions. Nature (2014).
16. Shimada, S. G. & LaMotte, R. H. Behavioral differentiation between itch and pain in mouse. Pain 139, 681-687 (2008).
17. Fujisawa, D., et al. Expression of Mas-related gene X2 on mast cells is upregulated in the skin of patients with severe chronic urticaria. J Allergy Clin Immunol 134, 622-633 e629 (2014).
18. Wallengren, J. Topical aprepitant in clinical and experimental pruritus. Archives of dermatology 148, 957-959 (2012).
19. Santini, D., et al. Aprepitant for management of severe pruritus related to biological cancer treatments: a pilot study. The Lancet. Oncology 13, 1020-1024 (2012).
20. Hagiwara, D., et al. Studies on neurokinin antagonists. 1. The design of novel tripeptides possessing the glutaminyl-D-tryptophylphenylalanine sequence as substance P antagonists. J Med Chem 35, 2015-2025 (1992).
21. Shimada, S. G., et al. Scratching behavior in mice induced by the proteinase-activated receptor-2 agonist, SLIGRL-NH2 (SEQ ID NO: 7). Eur J Pharmacol 530, 281-283 (2006).
22. Wahlgren, C. F., et al. Patients' perception of itch induced by histamine, compound 48/80 and wool fibres in atopic dermatitis. Acta dermato-venereologica 71, 488-494 (1991).
23. Schemann, M., et al. The mast cell degranulator compound 48/80 directly activates neurons. PloS one 7, e52104 (2012).
24. Hagermark, O., et al. Flare and itch induced by substance P in human skin. The Journal of investigative dermatology 71, 233-235 (1978).
25. Kuraishi, Y., et al. Scratching behavior induced by pruritogenic but not algesiogenic agents in mice. Eur J Pharmacol 275, 229-233 (1995).
26. Kamohara, M., et al. Identification of MrgX2 as a human G-protein-coupled receptor for proadrenomedullin N-terminal peptides. Biochemical and biophysical research communications 330, 1146-1152 (2005).
27. Robas, N., et al. MrgX2 is a high potency cortistatin receptor expressed in dorsal root ganglion. The Journal of biological chemistry 278, 44400-44404 (2003).
28. Subramanian, H., et al. Mas-related gene X2 (MrgX2) is a novel G protein-coupled receptor for the antimicrobial peptide LL-37 in human mast cells: resistance to receptor phosphorylation, desensitization, and internalization. The Journal of biological chemistry 286, 44739-44749 (2011).
29. Reddy, V. B., et al. Redefining the concept of protease-activated receptors: cathepsin S evokes itch via activation of Mrgprs. Nat Commun 6, 7864 (2015).
30. Goswami, S. C., et al. Molecular signatures of mouse TRPV1-lineage neurons revealed by RNA-Seq transcriptome analysis. J Pain 15, 1338-1359 (2014).
31. Zhang, L., et al. Cloning and expression of MRG receptors in macaque, mouse, and human Brain Res Mol Brain Res 133, 187-197 (2005).
32. Flegel, C., et al. RNA-Seq Analysis of Human Trigeminal and Dorsal Root Ganglia with a Focus on Chemoreceptors. PloS one 10, e0128951 (2015).
33. Azimi, E., Lerner, E. A. & Elmariah, S. B. Altered manifestations of skin disease at sites affected by neurological deficit. The British journal of dermatology (2014).
34. Avula, L. R., et al. Expression and distribution patterns of Mas-related gene receptor subtypes A-H in the mouse intestine: inflammation-induced changes. Histochem Cell Biol 139, 639-658 (2013).
35. Rost, K., et al. Neurokinin 1 receptor antagonists—between hope and disappointment. Med Monatsschr Pharm 29, 200-205 (2006).
36. Kuehn, H. S., et al. Measuring mast cell mediator release. Curr Protoc Immunol Chapter 7, Unit 7.38 (2010).

TABLE 1

| GPCR | SP | SP + QWF | SP + L-733060 | Dynorphin B | Dynorphin B + QWF | LL-37 | LL-37 + QWF | PAMP-12 | PAM-12 + QWF | HK-1 |
|---|---|---|---|---|---|---|---|---|---|---|
| PAR2 | − | − | − | − | − | − | − | − | − | − |
| NK1R | + | − | − | − | − | − | + | − | − | + |
| MrgX1 | − | − | − | + | − | − | − | − | − | − |
| MrgX2 | + | − | + | + | − | + | + | + | + | + |
| MrgX2 E164R | − | − | + | − | − | + | + | + | + | − |
| MrgX3 | − | − | − | − | − | − | − | − | − | − |
| MrgX4 | − | − | − | − | − | − | − | − | − | − |
| MrgC11 | − | − | − | − | − | − | − | − | − | − |
| MrgA1 | + | − | + | + | − | + | + | + | + | − |
| MrgA1 N172R | − | − | − | + | | | | | | |
| MrgA2a | − | − | − | − | − | − | − | − | − | − |
| MrgA2b | − | − | − | − | − | − | − | − | − | − |
| MrgA3 | − | − | − | − | − | − | − | − | − | − |
| MrgA4 | − | − | − | − | − | − | − | − | − | − |
| MrgA9 | − | − | − | − | − | − | − | − | − | − |
| MrgA10 | − | − | − | + | − | − | − | − | − | − |
| MrgB2 | + | − | + | + | − | + | − | + | − | − |
| MrgB2 E171R | − | − | − | − | − | | | | | |
| MrgB4 | − | − | − | − | − | − | − | − | − | − |
| MrgB5 | − | − | − | − | − | − | − | − | − | − |
| dMrgXB5 | + | | | + | | | | | | |

| GPCR | HK-1 + QWF | TSLP | TSLP + QWF | 48/80 | 48/80 + QWF | SLIGRL | QWF + SLIGRL | FLRF | NPFF | Cortistatin-14 |
|---|---|---|---|---|---|---|---|---|---|---|
| PAR2 | − | − | − | + | − | + | + | − | − | − |
| NK1R | − | − | − | − | − | − | − | − | − | − |
| MrgX1 | − | − | − | + | − | − | − | − | + | − |
| MrgX2 | − | + | − | + | − | + | − | − | + | + |
| MrgX2 E164R | − | − | − | − | − | − | − | − | − | − |
| MrgX3 | − | − | − | − | − | − | − | − | − | − |
| MrgX4 | − | − | − | − | − | − | − | − | − | − |
| MrgC11 | − | − | − | − | − | + | − | + | + | − |
| MrgA1 | − | − | − | + | − | − | − | + | + | + |
| MrgA1 N172R | | | | | | − | | | | − |
| MrgA2a | − | − | − | + | − | − | − | − | − | − |
| MrgA2b | − | − | − | − | − | − | − | − | − | − |
| MrgA3 | − | − | − | − | − | − | − | − | − | − |
| MrgA4 | − | − | − | − | − | − | − | − | − | − |
| MrgA9 | − | − | − | − | − | − | − | − | − | − |
| MrgA10 | − | − | − | + | − | − | − | − | − | − |
| MrgB2 | − | − | − | + | − | | | | | + |
| MrgB2 E171R | | | | | | | | | | |
| MrgB4 | − | − | − | − | − | − | − | − | − | − |
| MrgB5 | − | − | − | − | − | − | − | − | − | − |
| dMrgXB5 | | | | | | | | | | |

TABLE 1

| | | | | |
|---|---|---|---|---|
| SP: 50 µM | L-733060: 100 µM | LL-37: 1 µM | TSLP: 1 µM | HK-1: 50 µM |
| QWF: 1 µM | Dynorphin B: 10 µM | PAMP-12: 1 µM | 48/80: 10 µg/ml | |
| SLIGRL/SLIGKV: 10 µM | | FLRF: 1 µM | Cortistatin-14: 1 µM | |

QWF does not inhibit FLRF, NPFF and cortistatin-14.
QWF does not inhibit cat S, papain or Der P1 activation of MrgX2, MrgC11, MrgX1 or PAR2.
QWF does not inhibit PAR2 activation by SLIGRL. However, it inhibits MrgX2 and MrgC11 activation by SLIGRL.
QWF inhibits PAR2 activation by 48/80.
NPFF at 50 µM activates MrgX2, MrgA1, MrgA10 and NK1R. Not inhibited by QWF (25 µM) or FK888 (10 µM).
FK888 (10 µM) does not inhibit MrgX2 or MrgA1 response to SP.
MrgX1, MrgA3 and MrgB2: Chloroquine +, QWF does not inhibit activation of MrgX1, MrgA3 and MrgB2 by CQ.
MrgX2: SLIGRL or SLIGKV +
GABA does not activate MrgX2 or MrgA1.
MrgX2 + Dyn B (10 uM) + SP (50 uM); response (after 2 min)
MrgX2 + SP (50 uM) + Dyn B (10 uM); no response (after 2 min)
MrgX2 + Cortistatin (1 uM) + SP (50 uM); response (after 2 min)
MrgX2 + SP (50 uM) + Cortistatin (1 uM); no response (after 2 min)

TABLE 1-continued

MrgX2 + PAMP12 (1 μM) + SP (50 μM); no response (after 2 min)
MrgX2 + SP (50 μM) + PAMP12 (1 μM); no response (after 2 min)
It may be that SP internalizes MrgX2, whereas dyn B and cortistatin may not internalize.
Capsaicin (3 μM) does not activate MrgC11 or MrgX2.
Histamine activation of His R is not inhibited by QWF.
The SP derivative, GR73632 (VPML-(7-11)-SP) activates MrgX2, MrgA1 and MrgB2. The activation is inhibited by QWF.
The mutants MrgX2E164R and MrgA1N172R and MrgB2E172R are inactive for GR73632.

TABLE 2

| Cysteine protease inhibitors |
|---|
| E-64 |
| U.S. Pat. No. 6,835,727 Cathepsin cysteine protease inhibitors |
| U.S. Pat. No. 7,279,478 Cathepsin cysteine protease inhibitors |
| U.S. Pat. No. 6,953,793 Substituted pyrazoles and methods of treatment with substituted pyrazoles |
| (WO/2005/066159) Cathepsin cysteine protease inhibitors |
| US 2007/0117785 Substituted pyrazoles and methods of treatment with substituted pyrazoles Stefin A, stefin B, cystatin C |
| human testican-1 |
| naphthalene endoperoxide (effective against Cathepsin B, L, S) |
| fluoromethyl ketone |
| heterocyclic oxygen-containing peptidomimetics |
| vinyl sulfones |
| pyrazole-based compounds such as 1-[3-[4-(6-Chloro-2,3-dihydro-3-methyl-2-oxo-1H-benzimidazol-1-yl)-1-piperidinyl]propyl]-4,5,6,7-tetrahydro-5-(methylsulfonyl)-3-[4-(trifluoromethyl)phenyl]-1H-pyrazolo[4,3-c]pyridine (JNJ 10329670) RWJ-445380 |
| Compounds I, II, and III, from Boehringer Ingelheim Pharmaceuticals |
| Leupeptin |
| chloroquine |

What is claimed:

1. A method of preventing or treating itch or treating a disease or disorder having itch as a symptom or sensation associated with a disease or disorder in a subject, the method comprising administering a therapeutically effective amount of an MRG receptor antagonist to the subject, wherein the MRG receptor antagonist is a tri-peptide QWF (Gln-Trp-Phe) or an analog or a derivative thereof.

2. The method of claim 1, whereby the itch sensation is reduced.

3. The method of claim 1, wherein the MRG receptor antagonist also antagonizes an NK1 receptor.

4. The method of claim 1, wherein the tri-peptide QWF is [Boc-Gln-D-Trp(Formyl)-Phe benzyl ester] or the tri-peptide QWF [Gln-D-Trp(Formyl)-Phe benzyl ester] or an analog or a derivative thereof.

5. The method of method of claim 1, wherein the disease or disorder is selected from the group consisting of anaphylaxis, pruritus ani, cough, migraine, pain, and pain of apthous ulcers, mastocytosis, and mast cell activation syndrome, cholestasis, eczema, atopic eczematous dermatitis, seborrheic dermatitis, scalp itch, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen plans, lichen planopilaris, frontal fibrosing alopecia, central centrifugal scarring alopecia, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodermatoses, skin blisters, adult acne, chicken pox, seasonal allergy, summer seasonal recurrent dermatitis, prurigo nodularis, notalgia paresthetica, cutaneous T-cell lymphoma, dermatitis herpetiformis, X-linked ichthyosis, drug reactions, chronic renal failure, and Hodgkins lymphoma.

6. The method of method of claim 1, wherein the MRG receptor antagonist is administered topically to the subject or administered systemically to the subject.

7. The method of method of claim 1, the method further comprising administering an additional agent to the subject in combination with the MRG receptor antagonist, wherein the additional agent has anti-itch properties.

8. The method of claim 7, wherein the additional agent is selected from the group consisting of a mast cell stabilizer, a TRP channel inhibitor or activator, an inhibitor of a nerve growth factor receptor, or an inhibitor of a cytokine, or interleukin-4 or its receptor or interleukin-31 or its receptor or a calcinuerin inhibitor or a corticosteroid.

\* \* \* \* \*

SEQUENCE LISTING

```
<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Ser Leu Leu Arg Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Pro Gly Lys Phe
1               5

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcgagagca tggatccaac cacc                                          24

<210> SEQ ID NO 4
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 4
aagcttctct acaccagact gcttctcg                                         28

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcgagaaca tgagtggaga tttcctaatc aag                                   33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagctttcag ctgcagctct gaacagtttc cag                                   33

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Leu Ile Gly Arg Leu
1               5
```